(12) United States Patent  (10) Patent No.: US 7,153,824 B2
Palmer et al.  (45) Date of Patent: Dec. 26, 2006

(54) INHIBITORS OF PHOSPHODIESTERASES IN INFERTILITY

(75) Inventors: Stephen S. Palmer, Plympton, MA (US); Sean D. McKenna, Duxbury, MA (US); Stephen J. Arkinstall, Belmont, MA (US); Aliza Eshkol, LaRippe (CH); Michael C. MacNamee, Bourn (GB)

(73) Assignee: Applied Research Systems ARS Holding N.V. (AN)

( * ) Notice: Subject to any disclaimer, the term of this patent is extended or adjusted under 35 U.S.C. 154(b) by 0 days.

(21) Appl. No.: 10/817,312

(22) Filed: Apr. 1, 2004

(65) Prior Publication Data

US 2004/0259792 A1    Dec. 23, 2004

Related U.S. Application Data

(60) Provisional application No. 60/458,955, filed on Apr. 1, 2003, provisional application No. 60/470,434, filed on May 15, 2003, provisional application No. 60/540,301, filed on Jan. 28, 2004, provisional application No. 60/544,003, filed on Feb. 12, 2004.

(51) Int. Cl.
*A61K 31/00*  (2006.01)
(52) U.S. Cl. .................. 514/2; 436/65; 514/253.13; 435/69.2
(58) Field of Classification Search .............. None
See application file for complete search history.

(56) References Cited

U.S. PATENT DOCUMENTS

| 5,703,098 | A |  | 12/1997 | Muller et al. |
| 5,739,144 | A |  | 4/1998 | Warrellow et al. |
| 5,767,067 | A |  | 6/1998 | Arpaia et al. |
| 6,110,471 | A | * | 8/2000 | Conti et al. ............... 424/400 |
| 6,127,363 | A |  | 10/2000 | Doherty, Jr. et al. |
| 6,624,181 | B1 |  | 9/2003 | Kilian et al. |
| 6,649,633 | B1 |  | 11/2003 | Chambers et al. |
| 2002/0065324 | A1 |  | 5/2002 | Palmer et al. |
| 2002/0103106 | A1 |  | 8/2002 | Palmer et al. |
| 2003/0018037 | A1 |  | 1/2003 | Lempriere et al. |
| 2004/0029891 | A1 |  | 2/2004 | Ghazzi et al. |

FOREIGN PATENT DOCUMENTS

| DE | 1545687 | 8/1969 |
| DE | 20208869 | 12/1970 |
| DE | 2123328 | 12/1971 |
| DE | 2315801 | 10/1973 |
| DE | 2402908 | 7/1975 |
| DE | 2413935 | 10/1975 |
| DE | 3900233 | 7/1989 |
| EP | 0848000 | 8/1983 |
| EP | 0103497 | 1/1986 |
| EP | 0158380 | 1/1989 |
| EP | 0103497 | 9/1989 |
| EP | 0163965 | 11/1989 |
| EP | 0393500 | 10/1990 |
| EP | 0490823 | 6/1992 |
| EP | 0335386 | 9/1992 |
| EP | 0510562 | 10/1992 |
| EP | 0511865 | 11/1992 |
| EP | 0527117 | 2/1993 |
| EP | 0553174 | 8/1993 |
| EP | 0557016 | 8/1993 |
| EP | 0435811 | 9/1993 |
| EP | 0470805 | 9/1994 |
| EP | 0626939 | 12/1994 |
| EP | 0664289 | 7/1995 |
| EP | 0671389 | 9/1995 |
| EP | 0506194 | 8/1996 |
| EP | 0459505 | 10/1996 |
| EP | 0428302 | 9/1997 |
| EP | 0819688 | 1/1998 |
| EP | 0819689 | 1/1998 |
| EP | 0748805 | 4/1998 |
| EP | 0685474 | 9/1998 |
| EP | 0685475 | 1/1999 |
| EP | 0685479 | 1/1999 |
| EP | 0834508 | 8/2001 |
| EP | 0816357 | 1/2002 |
| EP | 0389282 | 2/2002 |
| EP | 0736532 | 5/2002 |
| EP | 0832886 | 11/2002 |
| EP | 0738715 | 1/2003 |
| EP | 0763534 | 2/2003 |
| EP | 0139464 | 1/2004 |
| JP | 92234389 | 8/1992 |
| JP | 94329652 | 11/1994 |
| JP | 95010875 | 1/1995 |
| JP | 98072415 | 3/1998 |
| JP | 98147585 | 6/1998 |

(Continued)

OTHER PUBLICATIONS

Jin, S.-L. et al. PNAS vol. 96, No. 21, 11998-12003 (1999).*

(Continued)

*Primary Examiner*—Jon Weber
*Assistant Examiner*—Anand Desai
(74) *Attorney, Agent, or Firm*—Howrey LLP; David W. Clough

(57) ABSTRACT

The present invention is directed to methods of increasing oocyte production in a mammal. More specifically, the specification describes methods and compositions for inducing follicular maturation using a PDE inhibitor. The inhibitor may be used alone at high doses. Alternatively, the follicular maturation is achieved by combining a low dose of FSH with the PDE inhibitor treatment.

70 Claims, 16 Drawing Sheets

FOREIGN PATENT DOCUMENTS

| | | |
|---|---|---|
| WO | WO 91/17991 | 11/1991 |
| WO | WO 92/00968 | 1/1992 |
| WO | WO 92/12961 | 8/1992 |
| WO | WO 93/07124 | 4/1993 |
| WO | WO 93/07146 | 4/1993 |
| WO | WO 93/15044 | 8/1993 |
| WO | WO 93/15045 | 8/1993 |
| WO | WO 93/18024 | 9/1993 |
| WO | WO 93/19068 | 9/1993 |
| WO | WO 93/19720 | 10/1993 |
| WO | WO 93/19747 | 10/1993 |
| WO | WO 93/19749 | 10/1993 |
| WO | WO 93/19751 | 10/1993 |
| WO | WO 93/25517 | 12/1993 |
| WO | WO 94/02465 | 2/1994 |
| WO | WO 94/12461 | 6/1994 |
| WO | WO 94/20455 | 9/1994 |
| WO | WO 94/22852 | 10/1994 |
| WO | WO 94/27947 | 12/1994 |
| WO | WO 95/01338 | 1/1995 |
| WO | WO 95/01980 | 1/1995 |
| WO | WO 95/04045 | 2/1995 |
| WO | WO 95/04046 | 2/1995 |
| WO | WO 95/05113 | 2/1995 |
| WO | WO 95/05386 | 2/1995 |
| WO | WO 95/08534 | 3/1995 |
| WO | WO 95/09623 | 4/1995 |
| WO | WO 95/09624 | 4/1995 |
| WO | WO 95/09627 | 4/1995 |
| WO | WO 95/09836 | 4/1995 |
| WO | WO 95/14667 | 6/1995 |
| WO | WO 95/14680 | 6/1995 |
| WO | WO 95/14681 | 6/1995 |
| WO | WO 95/17392 | 6/1995 |
| WO | WO 95/17399 | 6/1995 |
| WO | WO 95/19362 | 7/1995 |
| WO | WO 95/19978 | 7/1995 |
| WO | WO 95/20578 | 8/1995 |
| WO | WO 95/22520 | 8/1995 |
| WO | WO 95/24381 | 9/1995 |
| WO | WO 95/27692 | 10/1995 |
| WO | WO 95/35281 | 12/1995 |
| WO | WO 95/35283 | 12/1995 |
| WO | WO 95/35284 | 12/1995 |
| WO | WO 96/00218 | 1/1996 |
| WO | WO 96/01825 | 1/1996 |
| WO | WO 96/03399 | 2/1996 |
| WO | WO 96/06843 | 3/1996 |
| WO | WO 96/11690 | 4/1996 |
| WO | WO 96/11917 | 4/1996 |
| WO | WO 96/12720 | 5/1996 |
| WO | WO 96/26940 | 9/1996 |
| WO | WO 96/31486 | 10/1996 |
| WO | WO 96/31487 | 10/1996 |
| WO | WO 96/35683 | 11/1996 |
| WO | WO 96/36595 | 11/1996 |
| WO | WO 96/36596 | 11/1996 |
| WO | WO 96/36611 | 11/1996 |
| WO | WO 96/36625 | 11/1996 |
| WO | WO 96/36626 | 11/1996 |
| WO | WO 96/36638 | 11/1996 |
| WO | WO 96/38150 | 12/1996 |
| WO | WO 96/39408 | 12/1996 |
| WO | WO 96/40636 | 12/1996 |
| WO | WO 97/03967 | 2/1997 |
| WO | WO 97/05105 | 2/1997 |
| WO | WO 9704779 | 2/1997 |
| WO | WO 97/08143 | 3/1997 |
| WO | WO 97/09345 | 3/1997 |
| WO | WO 97/12895 | 4/1997 |
| WO | WO 97/15561 | 5/1997 |
| WO | WO 97/18208 | 5/1997 |
| WO | WO 97/19078 | 5/1997 |
| WO | WO 97/20833 | 6/1997 |
| WO | WO 97/22585 | 6/1997 |
| WO | WO 97/22586 | 6/1997 |
| WO | WO 97/23457 | 7/1997 |
| WO | WO 97/23460 | 7/1997 |
| WO | WO 97/23461 | 7/1997 |
| WO | WO 97/24117 | 7/1997 |
| WO | WO 97/24355 | 7/1997 |
| WO | WO 97/25312 | 7/1997 |
| WO | WO 97/28131 | 8/1997 |
| WO | WO 97/30999 | 8/1997 |
| WO | WO 97/31000 | 8/1997 |
| WO | WO 97/32853 | 9/1997 |
| WO | WO 97/35854 | 10/1997 |
| WO | WO 97/36905 | 10/1997 |
| WO | WO 97/43288 | 11/1997 |
| WO | WO 97/44036 | 11/1997 |
| WO | WO 97/44322 | 11/1997 |
| WO | WO 97/47604 | 12/1997 |
| WO | WO 97/48697 | 12/1997 |
| WO | WO 98/05327 | 2/1998 |
| WO | WO 98/06692 | 2/1998 |
| WO | WO 98/06704 | 2/1998 |
| WO | WO 98/07715 | 2/1998 |
| WO | WO 98/08828 | 3/1998 |
| WO | WO 98/08830 | 3/1998 |
| WO | WO 98/08841 | 3/1998 |
| WO | WO 98/08844 | 3/1998 |
| WO | WO 98/09946 | 3/1998 |
| WO | WO 98/09961 | 3/1998 |
| WO | WO 98/11113 | 3/1998 |
| WO | WO 98/14448 | 4/1998 |
| WO | WO 98/04534 | 5/1998 |
| WO | WO 98/18796 | 5/1998 |
| WO | WO 98/21208 | 5/1998 |
| WO | WO 98/22453 | 5/1998 |
| WO | WO 98/31674 | 7/1998 |
| WO | WO 98/40382 | 9/1998 |
| WO | WO 98/45268 | 10/1998 |
| WO | WO 98/55481 | 12/1998 |
| WO | WO 98/56756 | 12/1998 |
| WO | WO 99/05111 | 2/1999 |
| WO | WO 99/05112 | 2/1999 |
| WO | WO 99/05113 | 2/1999 |
| WO | WO 99/06404 | 2/1999 |
| WO | WO 99/18095 | 4/1999 |
| WO | WO 99/31071 | 6/1999 |
| WO | WO 99/31090 | 6/1999 |
| WO | WO 02/083239 | 10/2002 |
| WO | WO 02/083241 | 10/2002 |
| WO | WO 03/051344 | 6/2003 |

OTHER PUBLICATIONS

Manabe, N. et al. Journal of Reproduction and Development vol. 50, No. 5, 493-514 (2004).*

Brinton, L. et al. Fertility and Sterility vol. 83, No. 2, 261-274 (2005).*

Bowman, W.C. and Rand, M.J. Textbook of Pharmacology 2nd edition, pp. 20.20-20.21 (1980).*

Barbieri, R. et al. Endocrine Reviews 20(3): 249-252 (1999).*

Sher, G. and Fisch, J. Fertility and Sterility vol. 78, No. 5, pp. 1073-1076 (2002).*

Ahn, et al., "Potent Tetracyclic Guanine Inhibitors of PDE1 and PDE5 Cyclic Guanosine Monophosphate Phosphodiesterases With Oral Antihypertensive Activity," J. Med. Chem., vol. 40, pp. 2196-2210 (1997).

Ashton, et al., "Selective Type IV Phosphodiesterase Inhibitors as Antiasthmatic Agents, etc." J. Med. Chem. vol. 37, pp. 1696-1703 (1994).

Christensen, et al., "1,4-Cyclohexanecarboxylates: Potent and Selective Inhibitors of Phosphodiesterase 4 for the Treatment of Asthma," J. Med. Chem., vol. 41, pp. 821-835 (1998).

Cleland, et al., "Emerging Protein Delivery Methods," Curr Opin Biotechnol., vol. 12, pp. 212-219 (2001).

Corbin, et al., "S.H., Pharmacology of Phosphodiesterase-5 Inhibitors," International Journal of Clinical Practice, vol. 56 No. 6, pp. 453-459 (2002).

Fares, et al., "Design a Long-Acting Follitropin Agonist by Fusing the C-Terminal Sequence of the Chorionic Gonadotropin β subunit to the Follitropin β Subunit," Proc. National Acad. Sci., vol. 89, pp. 4304-4308 (1992).

Healy, et al., "Female Infertility: Causes and Treatment," Lancet, vol. vol. 343, pp. 1539-1544 (1994).

Jiang, et al., "Furoyl and Benzofuroyl Pyrroloquinolones as Potent and Selective PDE5 Inhibitors for Treatment of Erectile Dysfunction," J. Medical Chem., vol. 46, pp. 441-444 (2003).

Karsa, et al., "Encapsulation and Controlled Release," The Royal Society of Chemistry (1993).

Klein, et al., "Development and Characterization of a Long-Acting Recombinant hFSH Agonist," Human Reproduction, vol. 18, No. 1, pp. 50-56 (2003).

Klein, et al., "Pharmacokinetics and Pharmacodynamics of Single-Chain Recombinant Human Follicle-Stimulating Hormone Containing the Human Chorionic Gonadotropin Carboxyterminal Peptide in the Rhesus Monkey," Fertility and Sterility, vol. 77, No. 6, pp. 1248-1255 (2002).

LaPolt, et al., "Enhanced Stimulation of Follicle Maturation and Ovulatory Potential by Long Acting Follicle-Stimulating Hormone Agonists with Extended Carboxyl-Terminal Peptides," Endocrinology, vol. 131, No. 6, p. 2514-2520 (1992).

Luo, et al., "Novel Biomaterials for Drug Delivery," Expert Opinion Ther. Patents, vol. 11, pp. 1395-1410 (2001).

Matzuk, et al., "The Biological Role of the Carboxyl-Terminal Extension of Human Chorionic Gonadotroin β-Subunit," Endocrinology, vol. 126, No. 1, pp. 376-383 (1990).

Rotella, et al., "N-3-Substituted Imidazoquinazolinones: Potent and Selective PDE5 Inhibitors as Potential Agents for Treatment of Erectile Dysfunction," J. Med. Chem, vol. 43, pp. 1257-1263 (2000).

Terrett, et al., "Sildenafil (Viagra™ ), A Potent and Selective Inhibitor of Type 5 CGMP Phosphodiesterase with Utility For the Treatment of Male Erectile Dysfunction," Bioorganic and Medicinal Chemistry Letters, vol. 6, No. 15, pp. 1819-1824 (1996).

Thompson, et al., "Assay of Cyclic Nucleotide Phosphodiesterase and Resolution of Multiple Molecular Forms of the Enzyme," Advances in Cyclic Nucleotide Research, vol. 10, pp. 69-92 (1979).

Wiersma, et al., "Phosphodiesterase 3 Inhibitors Suppress Oocyte Maturation and Consequent Pregnancy Without Affecting Ovulation and Cyclicity in Rodents," J. Clin. Invest., vol. 102, No. 3, pp. 532-537 (1998).

Yacobi, et al., 1998, Oral Sustained Release Formulations: Design and Evaluation, Eva Halperin-Walega (Editor), 1st Ed.; Pergamon Press (1998).

Physician's Desk Reference, PDR™, $57^{th}$ Ed. pp. 2653-2656 (2003).

Physician's Desk Reference, PDR™, $52^{nd}$ Ed. pp. 1949-1951 (1998).

Physician's Desk Reference, PDR™, $52^{nd}$ Ed. pp. 2771-2773 (1998).

Physician's Desk Reference, PDR™, $52^{nd}$ Ed. pp. 2773-2775 (1998).

Physician's Desk Reference, PDR™, $57^{th}$ Ed. pp. 2401 (2003).

Physician's Desk Reference, PDR™, $57^{th}$ Ed. pp. 2994 (2003).

Physician's Desk Reference, PDR™, $57^{th}$ Ed. pp. 695 (2003).

Physician's Desk Reference, PDR™, $57^{th}$ Ed. pp. 1324-1325 (2003).

Physician's Desk Reference, PDR™, $57^{th}$ Ed. pp. 1325-1327 (2003).

Physician's Desk Reference, PDR™, $57^{th}$ Ed. pp. 3119-3121 (2003).

Physician's Desk Reference, PDR™, $57^{th}$ Ed. pp. 3124-3128 (2003).

International Search Report from PCT/US2004/010346 dated Oct. 26, 2004.

Sher, G., et al., "Vaginal Sildenafil (Viagra): A Preliminary Report of a Novel Method to Improve Uterine Artery Blood Flow and Endometrial Development in Patients Undergoing IVF," Human Reproduction, vol. 15, No. 4, pp. 806-809 (2000).

* cited by examiner

Rat Ovarian Dispersate
cAMP Assay - 5.07.03

JC410/FSHR
cAMP Assay 10.30.03

INHIBITORS OF PHOSPHODIESTERASES IN INFERTILITY

This application claims the benefit of U.S. Provisional Application No. 60/458,955, filed Apr. 1, 2003, U.S. Provisional Application No. 60/470,434, filed May 15, 2003, U.S. Provisional Application No. 60/540,301, filed Jan. 28, 2004, and U.S. Provisional Application No. 60/544,003, filed Feb. 12, 2004, each of which is incorporated by reference herein in its entirety.

FIELD OF INVENTION

The present invention is generally directed to reproductive biology and assisted reproductive technologies (ART), such as controlled ovarian hyperstimulation (COH) for in vitro fertilization (IVF). More specifically, the present invention is directed to methods and compositions for inducing follicle maturation in vivo using one or more phosphodiesterase inhibitors either alone or in combination with one or more gonadotropins, including the stimulation of follicle maturation for purposes such as ovulation induction (OI). In addition, the invention is directed to methods and compositions for inducing oocyte maturation in vitro, using one or more phosphodiesterase inhibitors either alone or in combination with one or more gonadotropins.

BACKGROUND OF THE INVENTION

The female human reproductive cycle relies on a number of gonadotropin hormones. Principle among these are the pituitary hormones follicle stimulating hormone (FSH) and luteinizing hormone (LH). During oogenesis, the process by which the female germ cell, the ovum, is produced, occurs within a follicle. A follicle is a collection of cells in the ovary containing an oocyte (egg). Follicle maturation which ultimately leads to ovulation, is dependent on the stimulatory effects of FSH.

In each menstrual cycle, many follicles are recruited for the maturation of the oocytes. At the beginning of the approximately 28-day menstrual cycle the follicles are in the primordial form, which is simply an oocyte surrounded by a single layer of cells. As follicular growth and maturation is activated by FSH, multiple layers of granulosa cells form around the initial single layer of cells, a process that continues through to midcycle. These granulosa cells are responsible for nourishing the oocyte and for the production and release of estrogen. FSH, produced by the pituitary induces aromatase activity in the granulosa cells thereby increasing the production of estrogen. Thus, concurrent with the maturation of a follicle there is an increase in estrogen production in the early part of the 28-day menstrual cycle. The follicle also contains receptors for the second pituitary gonadotropin, LH. As the follicle continues to grow and mature by mid-cycle (approx. day 14), a space (antrum) develops inside the mass of granulosa cells. At mid-cycle a surge of LH production acts on LH receptors to cause the follicle to rupture and release the oocyte which travels down the fallopian tube and, which may subsequently be fertilized. The normal ovulating woman recruits approximately 300 immature oocytes for each menstrual cycle. During a normal cycle, all but one follicle will regress (atresia), and a single dominant follicle will emerge and go on to release an oocyte.

Ovulation induction (OI) and assisted reproductive technologies (ART) regimens are hormone regimens that comprise two main phases: a stimulatory phase and an ovulatory phase. When appropriate, a suppression phase may precede the stimulatory phase. The suppression phase involves the administration of a GnRH agonist, which is used to suppress LH or estradiol levels. The stimulatory phase starts with the administration of an agent having follicle stimulating activity (such as FSH), and is usually 6 to 10 days long. Typically, a patient is treated with about 150 IU of FSH per day starting at about three days after spontaneous or induced menstruation. FSH administration is continued until there is one follicle of mean diameter greater than or equal to about 16–18 mm (follicle development can be evaluated by ultrasound). At this point, the ovulatory phase is induced using a relatively large dose (5,000–10,000 IU) of an agent having LH activity, such as human chorionic gonadotrophin (hCG), to rupture the follicle and mimic the natural luteinizing hormone (LH) peak or surge that occurs mid-cycle, to trigger release of a single oocyte into the fallopian tubes. The patient is instructed to have intercourse 24 to 38 hours after administration of the large dose of hCG. During the stimulatory phase, administration of follicle-stimulating hormone (FSH), or an agent exerting follicle-stimulating activity, or an agent stimulating endogenous FSH release, stimulates ovarian follicular growth. Administration of FSH or an agent exerting FSH-like activity or an agent stimulating endogenous FSH release need not be continuous in the stimulatory phase, nor need it continue until the end of the stimulatory phase. Alternative agents that can act in either the stimulatory phase or the ovulatory phase are desirable, particularly orally available agents. US 2002/0103106 A1 (Palmer et al.) discloses the oral and subcutaneous use of inhibitors of type IV phosphodiesterase in the ovulatory phase, to trigger ovulation. US 2003/0018037 (Westbrook Lempriere et al.) discloses the use of PDE5 inhibitors after ovulation in a non-assisted cycle to improve embryo survival, increase birth weight, increase uterine blood flow and increase progesterone serum levels.

Ovulation induction (OI) is the treatment of anovulatory or ammenorheic women to cause the release of a single oocyte into the fallopian tubes for in vivo fertilization or intrauterine insemination (IUI). The goal of an OI regimen is to cause a single oocyte to be released, so as to avoid multiple pregnancies. In a conventional regimen for OI, the first phase of treatment is called the stimulatory phase.

In some patients undergoing OI it may be desirable to begin treatment with a suppression phase. In the suppression phase, pituitary gonadotrophins are suppressed by the administration of a gonadotrophin releasing hormone (GnRH) agonist prior to commencing therapy with FSH. Administration of a GnRH agonist is started in the luteal phase of a menstrual cycle (usually on about day 20 of a menstrual cycle). Suppression of ovarian function usually takes from 8 to 21 days with a GnRH agonist, and may be monitored by monitoring LH or estradiol ($E_2$) levels (LH <5 IU/L, $E_2$<50 pg/ml generally indicate adequate suppression). The stimulatory phase is then started by administration of FSH. The use of a GnRH agonist suppresses the natural LH peak or surge which can trigger the release of oocytes prematurely. This allows better timing of release of the oocyte, and consequently intercourse. In patients suffering from polycystic ovarian syndrome (PCOS), it is also desirable to use a GnRH agonist, because these patients often have inappropriately high endogenous LH levels, it also permits the suppression of LH throughout the stimulatory phase, permitting better response to FSH.

The stimulatory phase of OI is also often carried out using agents that provoke endogenous FSH release, such as clomiphene citrate or aromatase inhibitors. Clomiphene citrate is administered during a stimulatory phase (usually a dose of 50 to 100 mg on days 3 to 7 or 5 to 9 of the menstrual cycle), causing an increase in endogenous FSH secretion, leading to follicular growth. Aromatase inhibitors, for example Letrozole, Anastrozole, YM-511, may be given on days 3 to 7 or 5 to 9 of the menstrual cycle, and also provoke a release of endogenous FSH, as described in WO 02/083239, which is incorporated herein by reference.

In contrast to OI, where a single ovulatory follicle and a single oocyte is desired, in assisted reproductive technologies (ART) regimens, it is desired to collect as many oocytes in a single cycle as possible. Treatment of infertility by ART, such as in vitro fertilization (IVF), intracytoplasmic sperm injection (ICSI), Gamete Intrafallopian Transfer Procedure (GIFT), and Zygote Intrafallopian Transfer Procedure (ZIFT), requires controlled ovarian hyperstimulation (COH) to increase the number of female gametes. Healy, et al., *Lancet* 343:1539–1544 (1994). For example, in vitro fertilization (IVF), which is now a commonly used treatment for human female and male subfertility, is a technique of ART based on retrieval of mature human oocytes followed by fertilization of the mature oocytes with spermatozoa. Under standard IVF treatment protocols, human mature oocytes are recruited by a long hormone treatment regimen, e.g. 30 days. This protocol is initiated by suppressing the patient's own FSH and LH by gonadotropin releasing hormone GnRH or an analog of GnRH, and is followed by injections of exogenous gonadotropins, e.g. FSH and/or LH, in order to ensure development of multiple preovulatory follicles. At an appropriate stage of follicular growth, multiple oocytes are harvested by aspiration immediately before ovulation. The aspirated oocyte is subsequently fertilized in vitro and cultured, typically for three days before transferral of the resulting embryo into the uterus at the 4–8 cell stage.

More specifically, standard regimens for COH in ART include a suppression phase, also called a down-regulation phase, in which endogenous LH is suppressed by administration of a GnRH agonist starting in the luteal phase of a menstrual cycle (usually on about day 20 of a menstrual cycle). Suppression of ovarian function usually takes from 8 to 21 days with a GnRH agonist, and may be monitored by monitoring LH or estradiol levels (LH<5 IU/L, $E_2$<50 pg/ml generally indicate adequate suppression). Down regulation is followed by a stimulatory phase in which follicular development is induced by daily administration of follicle stimulating hormone (FSH), usually at about 75–600 IU/day.

Alternatively, a GnRH antagonist may be used, instead of a GnRH agonist, in which case follicular stimulation with FSH is started, usually on day 1, 2 or 3 after spontaneous or induced menstruation, and endogenous LH production is suppressed by administration of a GnRH-antagonist starting on about day 6 after menses. GnRH antagonist and FSH administration are continued until the criteria for administration of an ovulation-triggering dose of hCG are met, as described below.

During the stimulatory phase, the ovaries are examined by ultrasound, to detect and measure the developing follicles. Because multiple follicular development is the objective of COH protocols in ART, when the ovaries show at least 3 follicles with a mean diameter greater than 16 mm (preferably one of 18 mm), an injection of hCG (5,000–10,000 IU) is given to trigger ovulation. Oocyte recovery is timed for 36–38 hours after the hCG injection. Oocytes are usually recovered from pre-ovulatory follicles, by aspiration.

Despite the fact that protocols such as those described above have been used in clinical protocols for a number of years, these protocols are not without some significant disadvantages. FSH has a relatively short half life, and treatment with FSH for either OI or ART involves daily injections of relatively large doses of FSH (75–600 IU FSH daily) during the stimulatory phase. The daily injections can cause patient discomfort and inconvenience and can be relatively costly. Such large doses and daily administration has the related risk of producing ovarian hyperstimulation syndrome (OHSS), which in severe cases may be life-threatening. There are other additional side-effects from the gonadotropin preparations including weight gain, bloating, nausea, vomiting, the time involved with the monitoring process, and the unknown long-term cancer risk. These hormone treatment regimens will become even more of a problem when IVF is offered to perfectly normal women in these programs due to infertility problems associated with the males partner's poor sperm quality. Thus, there are problems associated with the current protocols used in oocyte generation for IVF. There remains a need for the production of greater quantities of oocytes that are amenable to ovulation.

Due to the risks involved with administration of gonadotropins, various alternative protocols have been suggested. One way to alleviate the risks, side effects, and economic disadvantages of controlled ovarian stimulation protocols involves the retrieval of immature oocytes followed by in vitro maturation. In this approach, the female is not stimulated, or receives only minimal stimulation, and the retrieved oocytes are subjected to hormonal treatment in vitro. This in vitro maturation (IVM) protocol involves a significant reduction/elimination in a number of the side effects mentioned above and has the secondary economic advantages of reducing the amounts of hormones used for the treatment. However, while in animals in vitro maturation (IVM) has become an efficient method for producing oocytes for IVF, the recorded success rates for clinical human IVM have been low.

As another alternative, replacement of FSH with alternative medicaments having the ability to aid follicular growth and which avoid the risks of OHSS would be highly desirable. Furthermore, the provision of a preparation which acts with FSH to cause follicular growth would also be highly desirable, as it could augment low endogenous FSH levels, causing follicular growth in those patients who are anovulatory due to low endogenous FSH levels, or it could augment exogenously administered FSH, permitting an improved response in poor responders in ART, or permitting the same response in ART with lower doses and/or less frequent injections of FSH, at the same time avoiding the risks of OHSS.

SUMMARY OF THE INVENTION

In certain aspects, the present invention provides a method of increasing follicle maturation comprising treating a mammal with a phosphodiesterase (PDE) inhibitor in an amount effective to stimulate follicular growth and maturation. In another aspect the invention provides a use of an inhibitor of a phosphodiesterase enzyme for stimulating ovarian follicular growth in a patient. In still another aspect the invention provides a method for stimulating ovarian follicular growth in a patient in need thereof, comprising administering an effective dose of a phosphodiesterase inhibitor to the patient. Also included as an aspect of the invention are methods of increasing follicle maturation comprising treating a mammal with a PDE inhibitor and a gonadotropin hormone, wherein the PDE and gonadotropin are provided in a collective amount effective to stimulate follicular growth and maturation.

In another aspect, the invention provides a use of a PDE inhibitor for the preparation of a medicament for stimulating ovarian follicular growth in a patient. Preferably, PDE inhibitor is used in the preparation of a medicament for stimulating ovarian follicular growth in a patient undergoing ovulation induction. More preferably, the PDE is used in the preparation of a medicament for stimulating ovarian follicular growth in a patient undergoing controlled ovarian hyperstimulation for assisted reproductive technologies. The PDE inhibitor is administered starting in the stimulatory phase, before ovulation, and is preferably stopped before or on the day when the ovulatory phase is started by administration of large dose of an agent having LH-activity (such as 5,000–10,000 hCG). Most preferably administration of the PDE inhibitor stops two, one or zero days before the day on which hCG is administered. Most preferably administration of the PDE inhibitor stops on the day on which hCG is administered.

The medicament may be for simultaneous, separate, or sequential administration with FSH, or an agent having FSH activity, or an agent leading to endogenous FSH release. Preferably, the medicament is for simultaneous, separate, or sequential administration with FSH. Alternatively, the medicament is for simultaneous, separate, or sequential administration with an agent having FSH activity, or an agent leading to endogenous FSH release. The medicament is preferably administered starting at or about day 2 to 3 after menses. It is administered on a daily basis until follicular growth is sufficient at which point an ovulation triggering dose of hCG, preferably 5,000–10,000 IU, is administered. When the medicament is administered with FSH, the dose of FSH is reduced with respect to the dose required in the same patient in the absence of the PDE inhibitor, in order to achieve the same result in terms of follicular growth.

In preferred embodiments according to this aspect of the invention, the PDE inhibitor is an inhibitor of at least one PDE type selected from 1, 5, and 6. The PDE inhibitor is selected from the following compounds: 5-[2-ethoxy-5-(4-methyl-1-piperazinylsulphonyl)phenyl]-1-methyl-3-n-propyl-1,6-dihydro-7H-pyrazolo[4,3-d]pyrimidin-7-one (sildenafil); Zaprinast; dipyridamole; 5-(2-ethoxy-5-morpholinoacetylphenyl)-1-methyl-3-n-propyl-1,6-dihydro-7H-20pyrazolo[4,3-d]pyrimidin-7-one; 3-ethyl-5-[5-(4-ethylpiperazin-1-ylsulphonyl)-2-n-propoxyphenyl]-2-(pyridin-2-yl)methyl-2,6-dihydro-7H-pyrazolo[4,3-d]pyrimidin-7-one; 3-ethyl-5-[5-(4-ethylpiperazin-1-ylsulphonyl)-2-(2-methoxyethoxy)pyridin-3-yl]-2-(pyridin-2-yl) methyl-2,6-dihydro-7H-pyrazolo[4,3-d]pyrimidin-7-one; (+)-3-ethyl-5-[5-(4-ethylpiperazin-1-ylsulphonyl)-2-(2-methoxy-1 (R)-methylethoxy)pyridin-3-yl]-2-methyl-2,6-dihydro-7H-pyrazolo[4,3-d]pyrimidin-7-one; 5-[2-ethoxy-5-(4-ethylpiperazin-1-ylsulphonyl)pyridin-3-yl]-3-ethyl-2-[2-methoxyethyl]-2,6-dihydro-7H-pyrazolo[4,3-d]pyrimidin-7-one; 5-[2-iso-butoxy-5-(4-ethylpiperazin-1-ylsulphonyl)pyridin-3-yl]-3-ethyl-2-(1-methylpiperidin-4-yl)-2,6-dihydro-7H-pyrazolo[4,3-d]pyrimidin-7-one; 5-[2-ethoxy-5-(4-ethylpiperazin-1-ylsulphonyl)pyridin-3-yl]-3-ethyl-2-phenyl-2,6-dihydro-7H-pyrazolo[4,3-d]pyrimidin-7-one; 5-(5-acetyl-2-propoxy-3-pyridinyl)-3-ethyl-2-(1-isopropyl-3-azetidinyl)-2,6-dihydro-7H-pyrazolo[4,3-d]pyrimidin-7-one; 5-(5-acetyl-2-butoxy-3-pyridinyl)-3-ethyl-2-(1-ethyl-3-azetidinyl)-2,6-dihydro-7H-pyrazolo[4,3-d]pyrimidin-7-one; (6R,12aR)-2,3,6,7,12,12a-hexahydro-2-methyl-6-(-3,4-methylenedioxyphenyl)pyrazino[2',1':6,1]pyrido[3,4-b]indole-1,4-dione (Tadalafil; IC-351); the compound of examples 78 and 95 of published international application WO 95/19978, as well as the compound of examples 1, 3, 7 and 8 therein; 2-[2-ethoxy-5-(4-ethyl-piperazin-1-yl-1-sulphonyl)-phenyl]-5-methyl-7-propyl-3H-imidazo[5,1-f][1,2,4]triazin-4-one (vardenafil); the compound of example 11 of published international application WO93/07124 (EISAI); compounds 3 and 14 from Rotella D P, J. Med. Chem., 2000, 43,1257; 4-bromo-5-(pyridylmethylamino)-6-[3-(4-chlorophenyl)-propoxy]-3(2H)pyridazinone; 1-[4-[(1,3-benzodioxol-5-ylmethyl)amiono]-6-chloro-2-quinozolinyl]-4-piperidine-carboxylic acid, monosodium salt; (+)-cis-5,6a,7,9,9,9a-hexahydro-2-[4-(trifluoromethyl)-phenylmethyl-5-methyl-cyclopent-[4,5]imidazo[2,1-b]purin-4(3H)one; furaziocillin; cis-2-hexyl-5-methyl-3,4,5,6a,7,8,9,9a-octahydrocyclopent[4,5]-imidazo[2-,1-b]purin-4-one; 3-acetyl-1-(2-chlorobenzyl)-2-propylindole-6-carboxylate; 3-acetyl-1-(2-chlorobenzyl)-2-propylindole-6-carboxylate; 4-bromo-5-(3-pyridylmethylamino)-6-(3-(4-chlorophenyl) propoxy)-3-(2H)pyridazinone; 1-methyl-5 (5-morpholinoacetyl-2-n-propoxyphenyl)-3-n-propyl-1,6-dihydro-7H-pyrazolo(4,3-d)pyrimidin-7-one; 1-[4-[(1,3-benzodioxol-5-yl methyl)amino]-6-chloro-2-quinazolinyl]-4-piperidinecarboxylic acid, monosodium salt; Pharmaprojects No. 4516 (Glaxo Wellcome); Pharmaprojects No. 5051 (Bayer); Pharmaprojects No. 5064 (Kyowa Hakko; see WO 96/26940); Pharmaprojects No. 5069 (Schering Plough); GF-196960 (Glaxo Wellcome); E-8010 and E-4010 (Eisai); Bay-38-3045 & Bay-38-9456 (Bayer), Vinpocetine (Richter Gideon); SCH-51866 (Schering-Plough), SCH-59498; (6aR,9aS)-2-(Biphenylylmethyl)-5,6a,7,8,9,9a-hexahydro-5-methyl-3(phenylmethyl)cyclopent[4,5]imidazo-[2,1-b]purin-4(3H)-one; 5'-Methyl-2' (biphenylylmethyl)-3'-(phenylmethyl) spiro[cyclopentane-1,7'(8'H)-[3H]imidazo[2,1-b]purin]-4(5'H)-one; (6aR,9aS)-5,6a,7,8,9,9a-Hexahydro-5-methyl-2-(phenylethynyl)-3-(phenylmethyl)cyclopent[4,5]imidazo[2,1-b]-purin-4(3H)-one; dipyridamole; AWD-12-171 and AWD-12-217 (ASTA Medica); BMS-341400 (Bristol Meyers Squibb); UK-343,664 (Pfizer); 5E-3623, 5E-3569, 5E-3657, E4021 (Eisai); KS-505a (Kyowa Hakko Kogyo); YC-1 (Yung Shin Pharmaceutical Industries); IDDB reference number 323951 (Bayer); WIN-61691 (Sanofi Winthrop); FR226807 (Fujisawa); IDDB references 461317, 462503, 461321, 461324, 466146 (Johnson & Johnson); pyridine-4-ylmethyl 3-(1,3-benzodioxol-5-yl)-9-oxo-1,3,4,9 tetrahydro-2H-pyrrolo[3,4-b]quinoline-2-carboxylate:

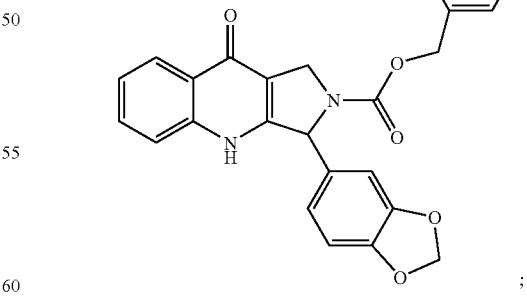

compounds listed in Table 1 of Jiang, et al., J. Med. Chem., 46:441–444 (2003), particularly compounds 20b, 20e, 20f, 20l, 20o, 20p, (−)-20q, 20t, 20u, 20v, 20w and 26a.

The PDE inhibitor may be a selective inhibitor of PDE 1 or PDE 5, or PDE 1 and PDE 5. The PDE inhibitor may be selected from Sildenafil and Zaprinast, Dipyridamole, and (6aR,9aS)-2-(Biphenylylmethyl)-5,6a,7,8,9,9a-hexahydro-5-methyl-3(phenylmethyl)cyclopent[4,5]imidazo-[2,1-b]purin-4(3H)-one and 5'-Methyl-2'(biphenylylmethyl)-3'-(phenylmethyl)spiro[cyclopentane-1,7'(8'H)-[3H]imidazo[2,1-b]purin]-4(5'H)-one ("compound no. 31" and "compound no. 33," respectively, described in Ahn, et al., *J. Med. Chem.*, 40:2196–2210 (1997)).

In another aspect, the invention provides a method of in vitro oocyte maturation comprising treating an oocyte in vitro with a PDE inhibitor, or with a PDE inhibitor and a gonadotropin hormone, wherein the PDE and gonadotropin are provided in a collective amount sufficient to cause oocyte maturation. Preferably, the increase in the number of mature oocytes is in the order of zero to one oocytes in the absence of said treatment, being increased to four or more oocytes by the use of the methods described herein.

A particular aspect of the present invention provides a method of increasing the follicle maturation in an animal comprising administering to the animal a composition comprising at least one PDE inhibitor and a gonadotropin hormone, wherein the PDE and gonadotropin are administered in a collective amount effective to increase the number of human chorionic gonadotropin responsive oocytes. In particularly preferred embodiments, the PDE inhibitor is a PDE 4 inhibitor. Exemplary PDE 4 inhibitors that may be used include but are not limited to select from the group consisting of Piclamilast, Roflumilast, ARIFLO (Cilomilast), Filaminast, Mesopram, D44 18, Arofylline, and CL1044, additional PDE 4 inhibitors may be used. Many are exemplified herein below, however it should be understood that analogs and derivatives of these compounds that have PDE 4 inhibitory activity also may be used. It is contemplated that the methods of the invention may be performed using only one PDE inhibitor. Alternatively, a cocktail of multiple PDE inhibitors may be employed. Such a cocktail may include one or more PDE 4 inhibitors in addition to one or more other PDE inhibitors. It is particularly contemplated that the composition may comprise at least one PDE 4 inhibitor and at least one other PDE inhibitor selected from the group consisting of a PDE 1 inhibitor, a PDE 5 inhibitor, a PDE 6 inhibitor, PDE 7 inhibitor, PDE 9 inhibitor, PDE 10 inhibitor, and PDE 11 inhibitor. In specific embodiments, the methods of the invention employ compositions which comprise two or more PDE 4 inhibitors.

In the methods of the present invention, the gonadotropin used for stimulating or increasing follicle maturation is selected from the group consisting of follicle stimulating hormone (FSH), luteinizing hormone (LH), and chorionic gonadotropin (CG) and combinations thereof. Preferably, the gonadotropin is FSH. In other embodiments, the method comprises administering FSH and further administering a non-FSH gonadotropin hormone, such as e.g., LH. Alternatively, the method comprises administering FSH in combination with a stimulator, agonist or adjuvant of FSH. Alternatively, the method may comprise administering a stimulator, agonist or adjuvant of FSH alone in combination with a PDE 4 inhibitor. Exemplary stimulators of FSH activity include aromatase inhibitors such as Letrozole, Anastrozole and Vorozole (see PCT/EP01/14730 and U.S. Patent Publication No. 20020103106, incorporated herein by reference).

In specific embodiments, the PDE inhibitor and the gonadotropin hormone treatment are administered concurrently. By "gonadotropin hormone treatment" the present invention contemplates FSH treatment alone, FSH treatment in combination with a non-FSH gonadotropin, or treatment with a stimulant or other agonist of FSH activity either alone or in combination with FSH and/or other non-FSH gonadotropin. In some embodiments, the PDE inhibitor is administered prior to the administration of the gonadotropin hormone. In other embodiments, the PDE inhibitor is administered after the administration of the gonadotropin hormone. The dosage of the FSH may be any dosage routinely used in a clinical setting. For example, the FSH may be administered at a dosage range of from about 5 to 450 IU/day. More preferably, the FSH is administered at a dosage range of from about 5 to 75 IU/day. In specific embodiments, it is contemplated that the administration of the PDE 4 or other PDE inhibitor will allow a reduction in the amount of FSH normally administered to an individual. For purposes of this application, a "suboptimal" dose of FSH is any such reduced dosage of FSH, that is, a dosage of FSH lower than would result in optimal stimulation of follicle maturation. The FSH may be recombinant FSH (r-FSH), preferably, human recombinant FSH (hFSH). In other embodiments, the FSH is purified from urine.

The invention also provides a method of increasing the in vivo development of preovulatory follicles in a mammal, the method comprising administering to the mammal a composition comprising at least one PDE 4 inhibitor and an exogenous FSH hormone. Such a method may further comprise suppression of endogenous FSH and LH production in the mammal prior to administration of the PDE 4 inhibitor and the FSH hormone. Preferably, the exogenous FSH hormone is a recombinant FSH hormone. In other embodiments, the exogenous FSH hormone is urinary FSH hormone.

In specific embodiments the PDE 4 inhibitor is administered in a dose of from about 0.05 mg/day to about 5 mg/day. It is contemplated that the dosage of the inhibitor will vary according to the specific inhibitor as well as the characteristics of the patient being treated. It is contemplated that the dosage may be 0.05 mg/day, 0.075 mg/day, 0.10 mg/day; 0.125 mg/day; 0.150 mg/day; 0.175 mg/day; 0.20 mg/day; 0.225 mg/day; 0.250 mg/day; 0.275 mg/day; 0.30 mg/day; 0.325 mg/day; 0.350 mg/day; 0.375 mg/day; 0.40 mg/day; 0.425 mg/day; 0.450 mg/day; 0.475 mg/day; 0.50 mg/day; 0.525 mg/day; 0.550 mg/day; 0.575 mg/day; 0.60 mg/day; 0.625 mg/day; 0.650 mg/day; 0.675 mg/day; 0.70 mg/day; 0.725 mg/day; 0.750 mg/day; 0.775 mg/day; 0.80 mg/day; 0.825 mg/day; 0.850 mg/day; 0.875 mg/day; 0.90 mg/day; 0.925 mg/day; 0.950 mg/day; 0.975 mg/day; 1.0 mg/day; 1.25 mg/day; 1.5 mg/day; 1.75 mg/day; 2.0 mg/day; 2.25 mg/day; 2.5 mg/day; 2.75 mg/day; 3.0 mg/day; 3.25 mg/day; 3.5 mg/day; 3.75 mg/day; 4.0 mg/day; 4.25 mg/day; 4.5 mg/day; 4.75 mg/day; 5.0 mg/day or more per day. In preferred embodiments, it is contemplated that the PDE 4 inhibitor is administered as in a dosage of from about 10 mg/day to about 200 mg/day. Those of skill in the art would understand that these are merely exemplary dosage amounts and ranges. It should be understood that any individual numerical amount between the dosages expressly recited herein is particularly contemplated and each of the individual values between these doses is specifically intended to be within the scope of the invention. The individual values between the specific doses recited herein have been omitted simply for ease of legibility and not because it was intended to be excluded from the scope of the application. The same is true of the other, non-PDE inhibitor compositions administered herein.

In other embodiments, it is contemplated that the FSH is administered in a dosage range of 5 IU FSH/day to 75 IU FSH per day. However, the FSH may be administered as a dosage of 150 IU FSH per day. The FSH is preferably administered in a single dose. Other embodiments contemplate administering the FSH in multiple doses. The FSH may be administered intramuscularly, subcutaneously or via any other convenient method of administration. Preferably, the FSH is administered between day 2 and day 14 of the menstrual cycle of the mammal. In specific embodiments, the FSH is administered for between 7 to 12 consecutive days.

In particular embodiments, the suppression of endogenous FSH and LH comprises administering gonadotropin releasing hormone (GnRH) or an analog thereof to the mammal. More particularly, the GnRH is administered to the mammal for 30 days prior to administration of the PDE 4 inhibitor and the FSH hormone. The dosage amounts of the GnRH may be any dosage routinely employed for suppression of endogenous gonadotropins. Such embodiments may typically employ GnRH or an antagonist thereof administered in a dosage range of from about 0.25 mg to about 3 mg GnRH on a daily basis.

In the methods of the present invention, the administration of PDE 4 inhibitor and FSH produces more hCG ovulatable oocytes in the mammal as compared to the production of hCG ovulatable oocytes in the absence of the administration of the PDE 4 inhibitor and FSH. For example, in the absence of such treatment the subject may produce zero or one hCG ovulatable oocytes, however the treatment increases that number to four or more hCG ovulatable oocytes. Thus, there may be produced 4, 5, 6, 7, 8, 9, 10, or more oocytes that are harvestable as a result of the methods of the present invention. The methods of the invention contemplate harvesting the oocytes 12 days after the initial administration of the PDE 4 inhibitor and the FSH hormone. The methods may further involve fertilizing the harvested oocytes in vitro, and culturing the harvested, fertilized oocytes to the 4–8 cell stage. Such 4–8 cell stage fertilized oocytes may further be transferred to the uterus of a mammal. The mammal may be the same mammal from which the oocytes were harvested or it may be a different mammal from which the oocytes were harvested.

The invention further provides a kit for the treatment of infertility, the kit comprising a first composition comprising at least one PDE 4 inhibitor in a pharmaceutically acceptable formulation, and a second composition comprising FSH in a pharmaceutically acceptable formulation. The kit may comprise urinary FSH or recombinant FSH. In either case the FSH is preferably human FSH. The FSH of the kit is preferably provided in a unit dose of between about 5 IU FSH and about 75 IU FSH. The kit may further comprise a third composition comprising LH in a pharmaceutically acceptable formulation. Exemplary amounts of LH employed in the unit doses in the kits are doses of between about 75 IU LH and about 150 IU LH.

Other features and advantages of the invention will become apparent from the following detailed description. It should be understood, however, that the detailed description and the specific examples, while indicating preferred embodiments of the invention, are given by way of illustration only, because various changes and modifications within the spirit and scope of the invention will become apparent to those skilled in the art from this detailed description.

BRIEF DESCRIPTION OF THE DRAWINGS

The following drawings form part of the present specification and are included to further illustrate aspects of the present invention. The invention may be better understood by reference to the drawings in combination with the detailed description of the specific embodiments presented herein.

DETAILED DESCRIPTION OF THE PREFERRED EMBODIMENTS

Ovarian stimulation using gonadotropin hormones is now recognized as a significant treatment regimen for couples having suboptimal levels of fertility. IVF procedures rely on the use of significant quantities of FSH and other gonadotropin hormones in order to stimulate the production of oocytes for fertilization. However, such ovarian stimulation often leads to significant deleterious side effects. Therefore, there is a need for additional methods of increasing the production of ovulatable oocytes that do not depend solely on ovarian stimulation with gonadotropins.

The present invention is directed to inducing follicle maturation using phosphodiesterase (PDE) inhibition. It has been discovered that inhibitors of PDE, when administered to immature rats, lead to an increase in the number of hCG-ovulatable oocytes. More particularly, PDE 4 inhibitors when administered in combination with suboptimal doses of FSH produce substantial increases in the number of such oocytes. The inventors have also surprisingly found that molecules that are inhibitors of phosphodiesterase (PDE) enzymes preferably PDE types selected from 1, 5, 6, 7, 9, 10, 11, more preferably PDE types 1 and 5, all within the scope of the present invention, are capable of aiding follicular growth in the presence of suboptimal amounts of FSH.

Figure 11:
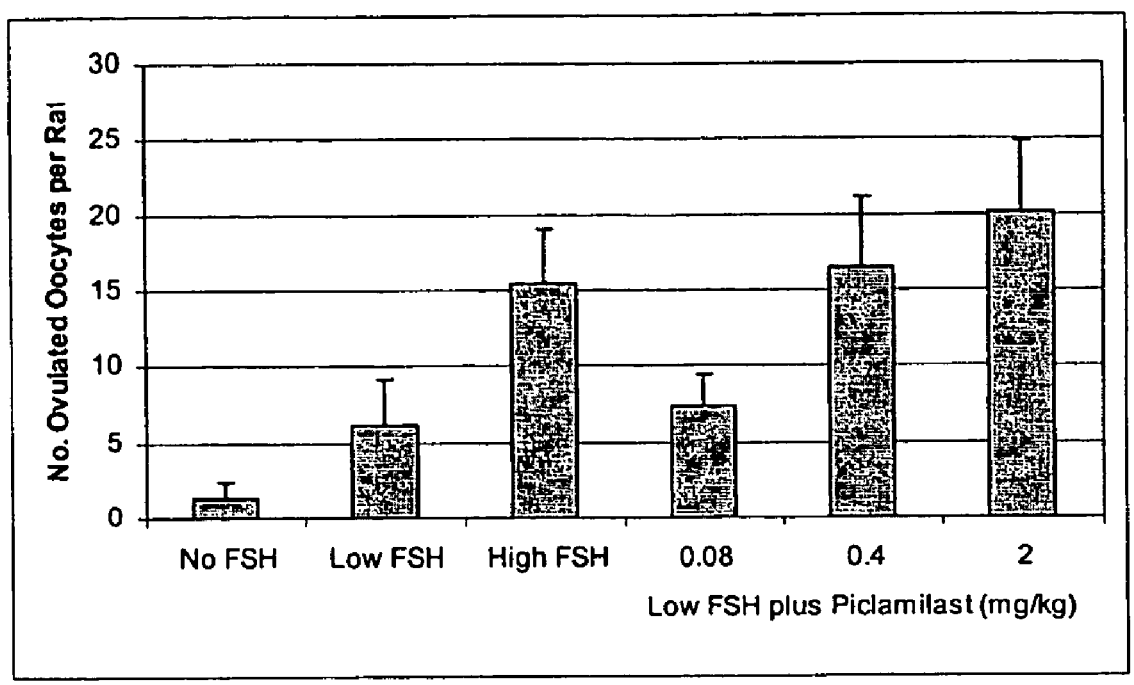
FIG. 11. In vivo demonstration of induction of follicle maturation by administration of a combination of a low dose of FSH with varying concentrations (0.08 mg/kg; 0.4 mg/kg; 2 mg/kg) of Piclamilast.
Figure 12:
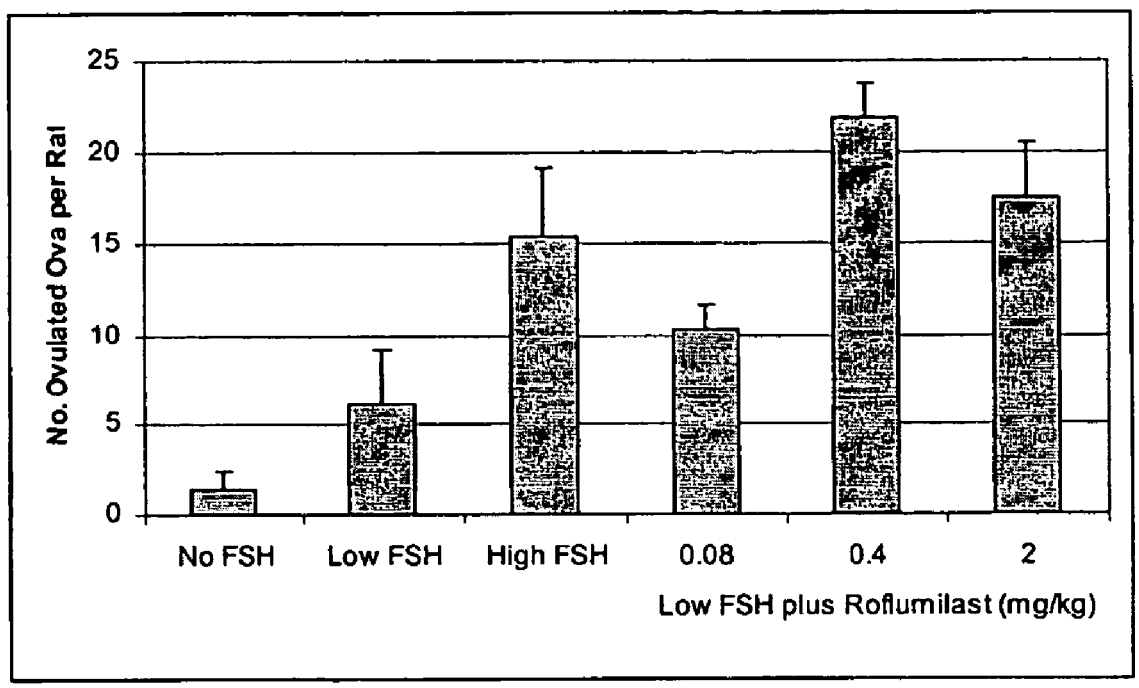
FIG. 12. In vivo demonstration of induction of follicle maturation by administration of a combination of a low dose of FSH with varying concentrations (0.08 mg/kg; 0.4 mg/kg; 2 mg/kg) of Roflumilast.

In specific exemplary embodiments, it was discovered that administration of PDE 4 inhibitors, Piclamilast and Roflumilast, increased FSH-induced follicle maturation. The most dramatic effects are seen when a low dose of FSH is administered in combination with a PDE 4 inhibitor. As can be seen from the data in FIGS. 12–14, administration of a low dose of FSH alone (see FIG. 11 and FIG. 12) will produce fewer ovulated ova per rat than ovarian stimulation with a high dose of FSH, which will typically yield in the order of 15–18 ovulated ova per rat. The problems of using high doses of FSH have been discussed above. The present invention demonstrates that the number of ovulatable oocytes can be markedly increased from the basal numbers seen with low FSH when the rats are treated with PDE 4 inhibitors. Indeed, as can be seen from FIG. 11 and FIG. 12, the combined administration of low dose of FSH with 0.4 mg/kg of either Piclamilast or Roflumilast produces more ovulatable oocytes than even the high dose of FSH alone (FIG. 11 and FIG. 12). In addition, as can be seen from FIG. 14 it also was noted that higher doses of Piclamilast (e.g., 2 mg/kg) alone, without co-administration of FSH, increased the hCG ovulatable oocytes.

Given the above exemplary data, it is contemplated that PDE inhibitors, and particularly PDE 4 inhibitors, may be used in producing ovulatable oocytes in vivo. This will be particularly useful in the context of the treatment of female infertility, but even a normal female will benefit from such treatment, particularly if there is a desire to increase the likelihood of pregnancy. In more specific embodiments, PDE 4 inhibitors are contemplated to be particularly useful in enhancing or increasing follicle maturation by producing an increase in the number of ovulatable oocytes in mammals in vivo as compared to the number of ovulatable oocytes that are produced in the absence of administration of the PDE 4 inhibitors.

Figure 13:
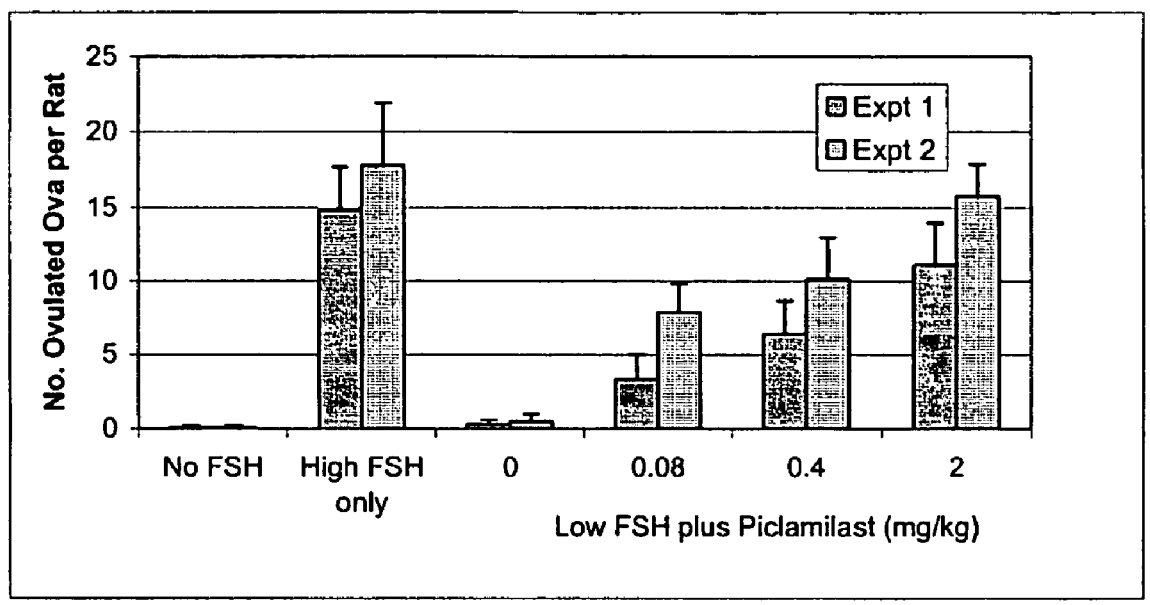
FIG. 13. In vivo demonstration of induction of follicle maturation. Comparison of oocyte production upon stimulation using low and high doses of FSH alone; varying concentrations (0.08 mg/kg; 0.4 mg/kg; 2 mg/kg) of Piclamilast and using a combination of a low dose of FSH with varying concentrations (0.08 mg/kg; 0.4 mg/kg; 2 mg/kg) of Piclamilast. Results from two independent studies are shown.
Figure 14:
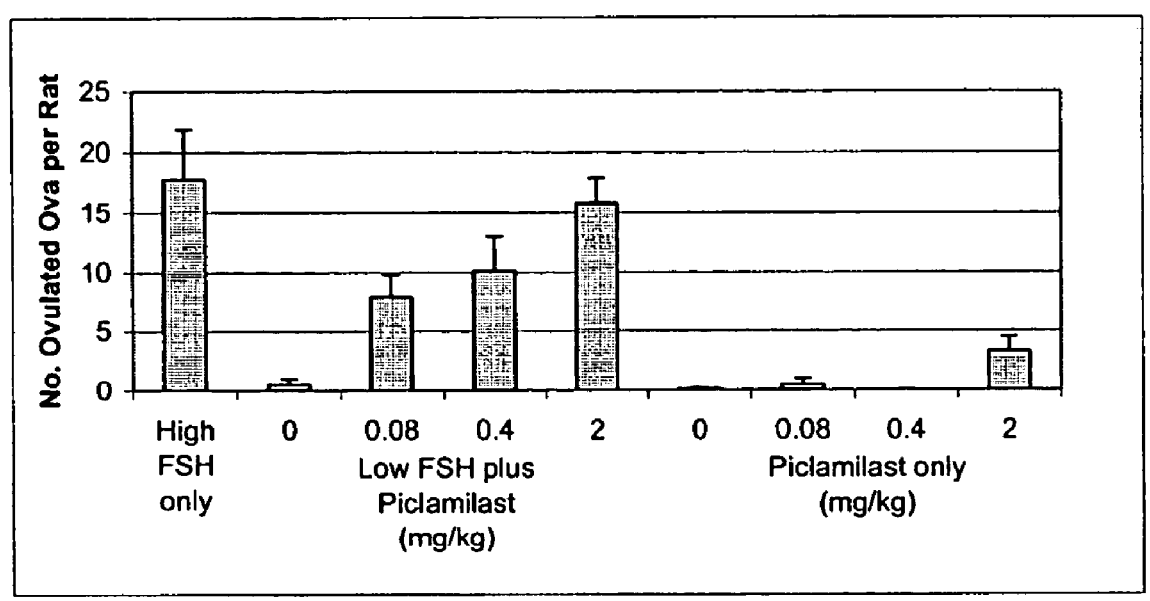
FIG. 14. In vivo demonstration of induction of follicle maturation. Cumulative data demonstrating increased oocyte production upon stimulation using a combination of a low dose of FSH with varying concentrations (0.08 mg/kg; 0.4 mg/kg; 2 mg/kg) of Piclamilast.

Given the findings in FIG. 14, it is contemplated that administration of PDE 4 inhibitors alone, without concomitant stimulation with low doses of FSH will be sufficient to increase the ovulatable oocytes in a female. As such, certain methods of the invention entirely circumvent the need for ovarian stimulation with exogenous FSH. Alternatively, the findings shown in FIGS. 11–14, the methods of the invention also comprise administering low levels of FSH in combination with PDE 4 inhibitors is sufficient to produce a marked increase in ovulatable oocytes. Regardless of whether the PDE 4 inhibitors are administered alone or as part of a combination treatment with low levels of FSH, the methods of the present invention provide a significant advance in the art by markedly reducing the amount of FSH stimulation required to yield a therapeutically beneficial increase in the ovulatable oocytes. Such a marked reduction in the amount of FSH needed is of great benefit because it reduces or eliminates many of the problems associated with administration of gonadotropins in fertility treatments. Specifically, a reduction in FSH dosage will decrease the likelihood of inducing OHSS in a female undergoing fertility treatment.

While much of the discussion presented herein is in terms of the use of PDE 4 inhibitors, the findings of the present invention support the use of other PDE inhibitors either alone, in combination with PDE 4 inhibitors, in combination with low doses of FSH, or in combination with PDE 4 inhibitors and low doses of FSH. For example, it is contemplated that other PDE inhibitors e.g., a PDE 5 inhibitor may be used in a method to increase the number of ovulatable oocytes in a mammal. Such a method may use the PDE 5 inhibitor alone or alternatively, the method may use the PDE 5 inhibitor in combination with either a PDE 4 inhibitor or a low dose of FSH, or the method may use the PDE 5 inhibitor in combination with a PDE 4 inhibitor and a low dose of FSH. In a preferred embodiment, the inhibitor is selective for phosphodiesterase types 1 and/or 5. (a "selective" inhibitor of PDE types 1 and/or 5, for example, means a molecule exhibiting an $IC_{50}$ for PDE types 1 and/or 5 that is at or about 10-fold, preferably 100-fold, more preferably 1000-fold, lower than the $IC_{50}$ of the molecule for other PDE types. The $IC_{50}$ of a molecule for a PDE enzyme can be measured by an in vitro assay, as reported, for example in Thompson, et al., *Adv. Cyclic Nucleotide Res.* 10:69–92 (1979). Also preferably the PDE inhibitor has a molecular weight under 500 Da. In a further preferred embodiment, the PDE inhibitor is an inhibitor of PDE type 1, most preferably a selective inhibitor of PDE type 1. Preferably the PDE inhibitor is a non-peptide PDE inhibitor. Yet another preferred alternative is a method in which a PDE 4 inhibitor is administered in combination with the PDE 5 inhibitor and a low dose of FSH. It is contemplated that the in such methods, the dose of FSH used when a PDE inhibitor is administered may be less than or equal to 75% of the dose of FSH that would be required in the same patient in the absence of the use of the PDE inhibitor in order to achieve the same level of follicular maturation. More preferably, the amount of FSH will be less than or equal to about 50% of the dose of FSH that would be required in the same patient, even more preferably, the dose will be less than or equal to at least 30% of the dose of FSH that would be required in the same patient without the PDE inhibitor. The combinations and methods of using the PDE inhibitors and FSH compoisitions are discussed in further detail herein below.

FSH and Other Gonadotropin Compositions

FSH is a pituitary glycoprotein hormone that is composed of two subunits. The α-subunit is common to FSH as well as the other glycoproteins, LH, hCG and TSH, the β-subunit confers FSH specificity. The field of infertility treatment is advanced and there are presently numerous FSH preparations that are commercially available and may be used in the methods of the invention. Such commercial preparations include urinary-derived FSH compositions and recombinant FSH compositions. These compositions include, e.g., Pergonal™, Fertinex™, Repronex™, Bravelle™, Humegon™, Gonal-F, Follistim™. These are merely exemplary commercial FSH preparations and those of skill in the art will understand that it may be possible to produce other such FSH preparations for use in the methods and compositions of the present invention. To the extent that the preceding compositions provide exemplary guidance as to formulations and dosages of FSH that may be used, they are discussed in further detail below. However, it should be understood that such doses and formulations may readily be modified and still be useful in the context of the present invention as long as the FSH dosages and formulations when administered in combination with one or more PDE inhibitors produce an increase in the number of ovulatable oocytes in vivo as compared to the number of oocytes produced in the absence of such administration.

Humegon™ (Organon, West Orange, N.J.) is a purified preparation of gonadotropins having FSH and LH activity. The properties, indications and protocols for the use of this preparation of gonadotropins is discussed in detail in the Physician's Desk Reference. (PDR™, 52$^{nd}$ Ed. 1998, pages 1949–1951, incorporated herein by reference). Briefly, each vial contains 75 IU or 150 IU FSH, 75 IU or 150 IU LH. Humegon™ and hCG may be administered in a sequential manner for ovulation and pregnancy in anovulatory infertile women in whom the cause of anovulation is functional and is not due to ovarian failure. Similarly Humegon™ and hCG are indicated for stimulating the development of multiple follicles (i.e., stimulation of follicle development) for ovulatory patients participating in an in vitro fertilization program. Typically, the dose of Humegon™ used to produce follicle maturation needs to be adjusted and individualized for each patient. However, typically the initial recommended dose would be 75 IU FSH/LH/day administered intramuscularly for 7 to 12 days followed by a dose of hCG (5,000 U to 10,000 U), administered one day after the last dose of Humegon™. Typically, the Humegon™ therapy should not continue for more than 12 consecutive days in a single course of therapy. For administration, the vial of Humegon™ (containing either 75 IU FSH/LH or 150 FSH/LH) is dissolved in 2 ml sterile saline and immediately administered intramuscularly.

Pergonal™ (Serono Laboratories Inc., Randolph, Mass.), described in the Physician's Desk Reference (PDR™, 52$^{nd}$ Ed. 1998, pages 2773–2775) is another commercially described purified preparation of gonadotropins prepared from the urine of postmenopausal women that may be used to supply the FSH compositions of the methods of the present invention. This composition is formulated for intramuscular administration. Again, this is a pharmaceutical composition that comprises unit doses of 75 IU FSH/LH or 150 IU FSH/LH. This pharmaceutical agent is well-recognized as a composition for administration to women for the production of follicular growth in women who do not have ovarian failure. To effect ovulation, rather than just follicle maturation, the 7–12 day course of Pergonal™ administration is followed by administration of a bolus of hCG.

Repronex™ (Ferring Pharmaceutical Inc., Tarrytown, N.J.), described in the Physician's Desk Reference (PDR™, 57$^{th}$ Ed. 2003, pages 1325–1327) is another exemplary purified preparation of gonadotropins isolated from the urine of post-menopausal women. This composition, available in unit doses of 75 IU or 150 IU FSH/LH activity, is administered for 7 to 12 days to produce ovarian follicular growth. Once sufficient follicular maturation has occurred, hCG is administered to induce ovulation. Repronex™ may be administered subcutaneously or intramuscularly to infertile patients with oligoanovulation or for patients undergoing assisted reproductive therapy. In the former indication, for patients that have received therapeutic intervention for the suppression of endogenous gonadotropin, Repronex™ is administered in an initial dose of 150 IU daily for the first five days of treatment. Based on clinical monitoring of e.g., serum estradiol levels and vaginal ultrasound monitoring, subsequent dosing may be adjusted up or down according to the patient's individualized response. Preferably, the dosage adjustment should not be made more than one every other day and should not exceed a change of more than 75 to 150 IU per adjustment. Preferably the maximum daily dose should not exceed 450 IU and the maximum number of days in consecutive course of Repronex™ therapy should not exceed 12 days. Such dosage adjustment guidelines are applicable to other FSH preparations discussed herein. If the patient appears to show the signs of follicle maturation, hCG is administered 1 day after the cessation of the Repronex™-based therapy.

In patients that are being treated with Repronex™ for assisted reproductive therapy, where the patient has received an initial gonadotropin suppressive therapy (e.g., GnRH or antagonist pituitary suppression) the typical initial dose may be 225 IU Repronex™, which may subsequently be adjusted according to the patient's individual response. Once a sufficient follicular development is evident, hCG (5,000–10,000 USP units) is administered to induce final follicular maturation in preparation for oocyte retrieval. In the event that the ovaries are abnormally enlarged as a result of Repronex™ administration hCG is withheld in order to decrease the possibility of developing OHSS. As indicated above, this composition is administrable subcutaneously. For subcutaneous administration, the Repronex™ is mixed 2 ml with saline and the subcutaneous injection is delivered to the lower abdomen.

Fertinex™ (Serono Laboratories Inc., Randolph, Mass.), described in the Pbysician's Desk Reference (PDR™, 52$^{nd}$ Ed. 1998, pages 2771–2773) is a highly purified FSH preparation purified from the urine of postmenopausal women. The purification of FSH composition is achieved through immunoaffinity chromatography using a murine monoclonal antibody to FSH, and produces an FSH with a specific activity profile of from about 8,500–13500 IU FSH/mg protein, very low amounts of LH, and a greater than 95% purity with respect to other urinary proteins. Such purification methods can readily be used to obtain FSH from non-commercial sources, e.g., urine of post-menopausal women. Fertinex™ is subcutaneously administrable and is supplied in containers containing 75 IU FSH or 150 IU FSH. This FSH has been administered in exemplary dosage ranges varying from 75 IU to 300 IU/day.

Bravelle™ (Ferring Pharmaceutical Inc., Tarrytown, N.J.), described in the Physician's Desk Reference (PDR™, 57th Ed. 2003, pages 1325–1327) is another exemplary highly purified FSH preparation that may be used in the present methods. Bravelle™ may be administered subcutaneously or intramuscularly and is available in unit doses 75 IU and 150 IU FSH.

Gonal F™ is a recombinant FSH preparation suitable for subcutaneous administration. The properties and characteristics of Gonal F™ are described in detail in the Physician's Desk Reference (PDR™, 57th Ed. 2003, pages 3124–3128).

In addition to these commercially available compositions, those of skill in the art may chose to purify FSH from natural source, e.g., urine of post-menopausal women, using techniques well known to those of skill in the art (See, e.g., U.S. Pat. No. 5,767,067).

Alternatively, those of skill in the art may choose to produce recombinant FSH using techniques well known to those of skill in the art. It is particularly contemplated that long-lasting FSH agonists would be useful in the methods of the invention. For example, it is known that hCG has a longer half life than FSH. Both of these gonadotropins share a common α-subunit, with the specific activity being conferred by the β-subunit. It has previously been demonstrated that the α-subunit of one gonadotropin may be used with the β-subunit of another and still yield a physiologically active chimeric gonadotropin. Further it has been demonstrated that the increased biopotency of hCG as compared to LH was due to the carboxy-terminal peptide of the β-subunit of hCG (Matzuk et al., Endocrinology 126:376–383, 1990). Long lasting agonists of FSH may be generated which contain a carboxy-terminal peptide extension of hCG β-subunit at the carboxy terminus of the FSH β-subunit. (LaPolt et al., Endocrinology, 131:6, 2514–2520, 1992). Such chimeric molecules have been shown to possess a markedly increased circulating half-life and potency as compared to wild-type FSH (Fares et al., Proc. Nat'l Acad. Sci., 89:4304–4308, 1992).

Regardless of the source of FSH, it has been demonstrated herein that significant induction of follicle maturation can be achieved using suboptimal doses of FSH. As discussed above, the typical dosage of FSH administered in fertility treatment protocols ranges from about 75 IU FSH/day to about 450 IU FSH/day for a course of from about 7 days to about 12 days. In the methods of the present invention, it is contemplated that the dose of FSH used for stimulating follicular maturation in combination with the PDE 4 or other PDE inhibitors may be the same as the doses presently being used for treatment of oligoanovulation and/or in assisted reproductive technologies (i.e., vary between 75 IU FSH to about 450 IU FSH per day). However, given that the present invention teaches that it is possible to obtain follicular maturation even with suboptimal doses of FSH, when such doses are administered in combination with a PDE 4 inhibitor, it is preferred that the dose be lower than these typical doses.

It is contemplated that the methods of the present invention may use as little as 5 IU FSH/day. Thus it is contemplated that any given treatment regimen may employ 5 IU FSH/day, 10 IU FSH/day, 15 IU FSH/day, 20 IU FSH/day, 25 IU FSH/day, 30 IU FSH/day, 35 IU FSH/day, 40 IU FSH/day, 45 IU FSH/day, 50 IU FSH/day, 55 IU FSH/day, 60 IU FSH/day, 65 IU FSH/day, 70 IU FSH/day, 75 IU FSH/day, 150 IU FSH/day, or more units of FSH per day. Of course, it should be understood that these are merely exemplary daily dosages and other doses of integers between any of the specifically recited doses also may be used in the treatment methods of the invention. Further, it should be understood that the dosage may be adjusted up or down during any given course of FSH administration. The FSH may be administered through any route normally employed for the administration of gonadotropin hormones. Most preferably the administration is either via intramuscular or subcutaneous injection. Throughout the treatment protocols, the patient is monitored for signs of adverse reaction including for signs of OHSS.

In addition to FSH, other gonadotropin hormones will be used in the methods of the present invention and packaged in the kits described herein. Such hormones include hCG. This is commercially available as Novarel™ (Ferring Pharmaceutical Inc., Tarrytown, N.J.), described in the Physician's Desk Reference (PDR™, 57th Ed. 2003, pages 1324–1325) and is a gonadotropin produced by the human placenta and obtained from the urine of pregnant women. Another commercial preparation of hCG is Pregnyl™ (Organon, West Orange, N.J.). The properties, indications and protocols for the use of this hormone are discussed in detail in the Physician's Desk Reference. (PDR™, 57th Ed. 2003, pages 2401). Both of these preparations are for intramuscular administration. Typically, this hormone is administered in a dosage of between about 5,000 Units and 10,000 Units to induce ovulation.

Yet another hormone that may be used and packaged herein is GNRH. There are numerous commercial sources of this hormone. GnRH and analogs thereof are commercially available as Cetrotide™ (Serono, PDR™, 57th Ed. 2003, pages 3119–3121); Eligard™ (Sanofi-Synthelabo, PDR™, 57th Ed. 2003, page 2994); Lupron™ (PDR™, 57th Ed. 2003, page 3185); and Zoladex™ (AstraZeneca PDR™, 57th Ed. 2003, page 695). These agents are used to suppress LH/FSH production in women and are therefore used to delay ovulation. Typical doses of these agents vary from about 0.25 mg to about 3 mg. Ovarian stimulation therapy with FSH is typically initiated on the 2nd or 3rd day of the menstrual cycle. The GnRH or analogs thereof are administered either once daily (lower dose, e.g., 0.25 mg), or as a single dose (e.g., 3 mg) during the early to mid-follicular phase (the "stimulatory phase"). GnRH is administered up until the day of hCG administration. When ultrasound analyses reveal that the follicles are of an adequate size, hCG is administered to induce ovulation and final maturation of the oocyte.

Phosphodiesterase Inhibitors

Phospohdiesterases (PDE) are a family of enzymes responsible for the metabolism of the intracellular second messengers cyclic AMP (cAMP) and cyclic GMP (cGMP). PDE 4 is a cAMP specific PDE that is the major, if not sole, cAIVIP metabolizing enzyme found in inflammatory and immune cells, and contributes significantly to cyclic AMP metabolism in smooth muscles. PDE 4 is inhibited by the antidepressant Rolipram (4-[3-(Cyclopentyloxy)-4-methoxy-phenyl]-2-pyrrolidinone; A.G. Scientific, Inc., San Diego, Calif.). Rolipram was the first generation of PDE 4 inhibitors developed (see Conti, Biology of Reproduction 67:1653–1661, 2002). Subsequently, other such inhibitors have been identified, including but not limited to Piclamilast, Roflumilast, ARIFLO (Cilomilast), Filaminast, Mesopram, D4418, Arofylline, and CL1044. In addition, other PDE inhibitors such as Sildenafil, A5701948/1 and A5701947/1 also will be useful in the present invention. Thus, particularly preferred PDE 4 inhibitors for use in the present invention include lirimilast. (Bayer AG); CDP-840 (Ceiltech Group PLC), NCS-613 (Centre National de la Recherche Scientifique (CNRS) E-4021(Eisai Co Ltd), GRC-3785 (Glenmark Pharmaceuticals Ltd), IC-485 (ICOS Corp); IPL-455903 (Inflazyme Pharmaceuticals Ltd), ONO-6 126 (Ono Pharmaceutical Co Ltd), Tofimilast (Pfizer Inc.), Piclamilast (Rhone-Poulenc SA (Aventis SA)), Cilomilast. (SmithKline Beecham PLC), Filaminast. (Wyeth-Ayerst Pharmaceuticals Inc), WAY-126120 (Wyeth-Ayerst Pharmaceuticals IncO), Mesopram (Schering), and Roflumilast (Altana).

The above and other PDE 4 inhibitors are well known to those of skill in the art and have been described in e.g., U.S. Pat. No. 6,649,633; U.S. Pat. No. 6,624,181; U.S. Pat. No. 6,127,363; DE 1545687, DE 2028869, DE 2123328, DE 2315801, DE 2402908, DE 2413935, DE 3900233, EP 0103497, EP 0139464, EP 0158380, EP 0163965, EP 0335386, EP 0389282, EP 0428302, EP 0435811, EP 0459505, EP 0470805, EP 0490823, EP 0506194, EP 0511865, EP 0527117, EP 0393500, EP 0510562, EP 0553174, EP 0557016, EP 0626939, EP 0664289, EP 0671389, EP 0685474, EP 0685475, EP 0685479, EP 0736532, EP 0738715, EP 0748805, EP 0763534, EP 0816357, EP 0819688, EP 0819689, EP 0832886, EP 0834508, EP 0848000, JP 92234389, JP 94329652, JP 95010875, JP 98072415, JP 98147585, U.S. Pat. Nos. 5,703, 098, 5,739,144, WO 9117991, WO 9200968, WO 9212961, WO 9307146, WO 9315044, WO 9315045, WO 9318024, WO 9319068, WO 9319720, WO 9319747, WO 9319749, WO 9319751, WO 9325517, WO 9402465, WO 9412461, WO 9420455, WO 9422852, WO 9427947, WO 9501338, WO 9501980, WO 9503794, WO 9504045, WO 9504046, WO 9505386, WO 9508534, WO 9509623, WO 9509624, WO 9509627, WO 9509836, WO 9514667, WO 9514680, WO 9514681, WO 9517392, WO 9517399, WO 9519362, WO 9520578, WO 9522520, WO 9524381, WO 9527692, WO 9535281, WO 9535283, WO 9535284, WO 9600218, WO 9601825, WO 9606843, WO 9611690, WO 9611917, WO 9612720, WO 9631486, WO 9631487, WO 9635683, WO 9636595, WO 9636596, WO 9636611, WO 9636625, WO 9636638, WO 9638150, WO 9639408, WO 9640636, WO 9703967, WO 9704779, WO 9705105, WO 9708143, WO 9709345, WO 9712895, WO 9718208, WO 9719078, WO 9720833, WO 9722585, WO 9722586, WO 9723457, WO 9723460, WO 9723461, WO 9724117, WO 9724355, WO 9725312, WO 9728131, WO 9730999, WO 9731000, WO 9732853, WO 9735854, WO 9736905, WO 9743288, WO 9744036, WO 9744322, WO 9747604, WO 9748697, WO 9804534, WO 9805327, WO 9806692, WO 9806704, WO 9807715, WO 9808828, WO 9808830, WO 9808841, WO 9808844, WO 9809946, WO 9809961, WO 9811113, WO 9814448, WO 9818796, WO 9821208, WO 9822453, WO 9845268, WO 9855481, WO 9856756, WO 9905111, WO 9905112, WO 9505113, WO 9906404, WO 9918095, WO 9501338, WO 9603399, WO 9636625, WO 9636626, WO 9735854, WO 9821208, WO 9831674, WO9840382, WO9855481, WO 9905111,WO 9905112,WO 9905113, WO 9931071 and WO 9931090. Any of these substances may be used as the PDE 4 inhibitor composition in the context of the present invention. Substances that have good oral availability are particularly preferred.

These inhibitors of PDE 4 may be administered through any route commonly employed for the administration of a PDE inhibitor. Typically these chemical agents are formulated for oral administration. The tablets may be formulated to comprise 50 μg; 100 μg; 200 μg; 250 μg; 300 μg; 400 μg; 450 μg; 500 μg. Currently, roflumilast is being developed for pulmonary indications with doses as of about 400 μg/day, for oral administration. It is contemplated that such doses may also be useful in the context of the present invention. The PDE 4 inhibitors are administered to the subject in a daily dose of 200 μg/day; 300 μg/day; 400 μg/day; 500 μg/day or even as much as 1 to 5 mg/day. Typically, the patient may receive as little as 100 μg/day for the course of treatment. Of course it should be understood the subject may receive more or less of the PDE 4 inhibitor according to individualized requirement. Typically, doses greater than 100 mg/day should be avoided. The PDE 4 inhibitor may be delivered in a single dose or alternatively may be subdivided and administered in multiple doses over a given period of time. Administration of ordinary tablets containing the inhibitors may be once, twice, three or more times a day. Also it should be understood that while oral administration is preferred, similar doses may be administered through other routine routes of administration.

Sildenafil is a pharmaceutically approved PDE 5 inhibitor that may provide additional guidance as to the formulations and routes of administration of PDE 4 inhibitors (see PDR™ 57$^{th}$ Ed. Pages 2653–2656). For treatment protocols, those of ordinary skill in the art may use the guidelines used for this pharmaceutical PDE inhibitor. Other PDE 5, as well as PDE 1 inhibitors may be useful in the present invention. Such inhibitors have been described in U.S. Patent Application No. 60/470,434 titled "Inhibitors of PDE Enzymes in Infertility," and U.S. patent application Ser. No. 10/014,812 (U.S. Patent Publication No. 20020103106, incorporated herein by reference in its entirety) titled "Methods of Inducing Ovulation" which describes a variety of PDE3/4 inhibitors for triggering ovulation that may be used in the follicle maturation methods of the present invention. It should be noted that the methods of the present invention are directed to methods of increasing follicle maturation and are distinct from methods of inducing ovulation. Additional compositions and are described in PCT/EP01/14730.

Exemplary inhibitors that may be useful in the combined therapies discussed herein include, but are not limited to, 5-[2-ethoxy-5-(4-methyl-1-piperazinylsulphonyl)phenyl]-1-methyl-3-7-propyl-1,6-dihydro-7H-pyrazolo[4,3-d]pyrimidin-7-one (sildenafil); Zaprinast; dypyrimadole; 5-(2-ethoxy-5-morpholinoacetylphenyl)-1-methyl-3-n-propyl-1, 6-dihydro-7H-20pyrazolo[4,3-d]pyrimidin-7-one; 3-ethyl-5-[5-(4-ethylpiperazin-1-ylsulphonyl)-2-n-propoxyphenyl]-2-(pyridin-2-yl)methyl-2,6-dihydro-7H-pyrazolo[4,3-d] pyrimidin-7-one; 3-ethyl-5-[5-(4-ethylpiperazin-1-ylsulphonyl)-2-(2-methoxyethoxy)pyridin-3-yl]-2-(pyridin-2-yl)methyl-2,6-dihydro-7H-pyrazolo[4,3-d]pyrimidin-7-one; (+)-3-ethyl-5-[5-(4-ethylpiperazin-1-ylsulphonyl)-2-(2-methoxy-1 (R)-methylethoxy)pyridin-3-yl]-2-methyl-2, 6-dihydro-7H-pyrazolo[4,3-d]pyrimidin-7-one; 5-[2-ethoxy-5-(4-ethylpiperazin-1-ylsulphonyl)pyridin-3-yl]-3-ethyl-2-[2-methoxyethyl]-2,6-dihydro-7H-pyrazolo[4,3-d] pyrimidin-7-one; 5-[2-iso-butoxy-5-(4-ethylpiperazin-1-ylsulphonyl)pyridin-3-yl]-3-ethyl-2-(1-methylpiperidin-4- yl)-2,6-dihydro-7H-pyrazolo[4,3-d]pyrimidin-7-one; 5-[2-ethoxy-5-(4-ethylpiperazin-1-ylsulphonyl)pyridin-3-yl]-3-ethyl-2-phenyl-2,6-dihydro-7H-pyrazolo[4,3-d]pyrimidin-7-one; 5-(5-acetyl-2-propoxy-3-pyridinyl)-3-ethyl-2-(1-isopropyl-3-azetidinyl)-2,6-dihydro-7H-pyrazolo[4,3-d]pyrimidin-7-one; 5-[2-iso-butoxy-5-(4-ethylpiperazin-1-ylsulphonyl)pyridin-3-yl]-3-ethyl-2-(1-methylpiperidin-4-yl)-2,6-dihydro-7H-pyrazolo[4,3-d]pyrimidin-7-one; 5-[2-ethoxy-5-(4-ethylpiperazin-1-ylsulphonyl)pyridin-3-yl]-3-ethyl-2-phenyl-2,6-dihydro-7H-pyrazolo[4,3-d]pyrimidin-7-one; 5-(5-acetyl-2-butoxy-3-pyridinyl)-3-ethyl-2-(1-ethyl-3-azetidinyl)-2,6-dihydro-7H-pyrazolo[4,3-d]pyrimidin-7-one; (6R,12aR)-2,3,6,7,12,12a-hexahydro-2-methyl-6-(−3,4-methylenedioxyphenyl)pyrazino[2',1':6,1]pyrido[3,4-b]indole-1,4-dione (Tadalafil; IC-351), i.e. the compound of examples 78 and 95 of published international application WO 95/19978, as well as the compound of examples 1, 3, 7 and 8 therein; 2-[2-ethoxy-5-(4-ethyl-piperazin-1-yl-1-sulphonyl)-phenyl]-5-methyl-7-propyl-3H-imidazo[5,1-f][1,2,4]triazin-4-one (vardenafil); the compound of example 11 of published international application WO93/07124 (EISAI); compounds 3 and 14 from Rotella D P, J. Med. Chem., 2000, 43,1257; 4-bromo-5-(pyridylmethy-lamino)-6-[3-(4-chlorophenyl)-propoxy]-3(2H)pyridazi-none; 1-[4-[(1,3-benzodioxol-5-ylmethyl)amiono]-6-chloro-2-quinozolinyl]-4-piperidine-carboxylic acid, monosodium salt; (+)-cis-5,6a,7,9,9,9a-hexahydro-2-[4-(tri-fluoromethyl)-phenylmethyl-5-methyl-cyclopent-[4,5]imi-dazo[2,1-b]purin-4(3H)one; furaziocillin; cis-2-hexyl-5-methyl-3,4,5,6a,7,8,9,9a-octahydrocyclopent[4,5]-imidazo[2-,1-b]purin-4-one; 3-acetyl-1-(2-chlorobenzyl)-2-propylindole-6-carboxylate; 3-acetyl-1-(2-chlorobenzyl)-2-propylindole-6-carboxylate; 4-bromo-5-(3-pyridylmethylamino)-6-(3-(4-chlorophenyl)propoxy)-3-(2H)pyridazinone; 1-methyl-5 (5-morpholinoacetyl-2-n-propoxyphenyl)-3-n-propyl-1,6-dihydro-7H-pyrazolo(4,3-d)pyrimidin-7-one; 1-[4-[(1,3-benzodioxol-5-yl methyl)amino]-6-chloro-2-quinazolinyl]-4-piperidinecarboxylic acid, monosodium salt; Pharmaprojects No. 4516 (Glaxo Wellcome); Pharmaprojects No. 5051 (Bayer); Pharmaprojects No. 5064 (Kyowa Hakko; see WO 96/26940); Pharmaprojects No. 5069 (Schering Plough); GF-196960 (Glaxo Wellcome); E-8010 and E-4010 (Eisai); Bay-38-3045 & Bay-38-9456 (Bayer), Vinpocetine (Richter Gideon); SCH-51866 (Schering-Plough), SCH-59498, (6aR, 9aS)-2-(Biphenylylmethyl)-5,6a,7,8,9,9a-hexahydro-5-methyl-3(phenylmethyl)cyclopent[4,5]imidazo-[2,1-b]purin-4 (3H)-one; 5'-Methyl-2'(biphenylylmethyl)-3'-(phenylmethyl)spiro[cyclopentane-1,7'(8'H)-[3H]imidazo [2,1-b]purin]-4(5'H)-one; (6aR,9aS)-5,6a,7,8,9,9a-Hexahydro-5-methyl-2-(phenylethynyl)-3-(phenylmethyl) cyclopent[4,5]imidazo[2,1-b]-purin-4(3H)-one; dipyridamole; AWD-12-171 and AWD-12-217 (ASTA Medica), BMS-341400 (Bristol Meyers Squibb), UK-343, 664 (Pfizer), 5E-3623, 5E-3569, 5E-3657, E4021 (Eisai), KS 505a (Kyowa Hakko Kogyo), YC-1 (Yung Shin Pharmaceutical Industries), IDDB reference number 323951 (Bayer), WIN-61691 (Sanofi Winthrop), FR226807 (Fujisawa), IDDB references 461317, 462503, 461321, 461324, 466146 (Johnson & Johnson); pyridine-4-ylm-ethyl3-(1,3-benzodioxol-5-yl)-9-oxo-1,3,4,9tetrahydro-2H-pyrrolo[3,4-b]quinoline-2-carboxylate:

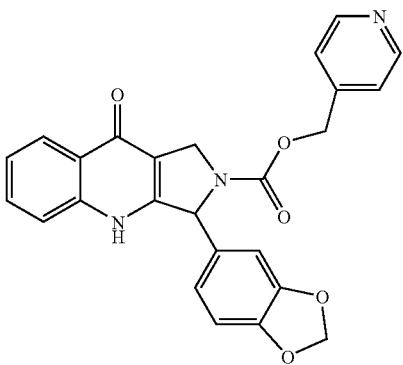

compounds listed in Table 1 of Jiang, et al., J. Med. Chem., 46:441–444 (2003), particularly compounds 20b, 20e, 20f, 20l, 20o, 20p, (−)-20q, 20t, 20u, 20v, 20w and 26a.

Particularly preferred PDE inhibitors are Sildenafil and Zaprinast, Dipyridamole, and compounds no. 31 and 33 (6aR,9aS)-2-(Biphenylylmethyl)-5,6a,7,8,9,9a-hexahydro-5-methyl-3(phenylmethyl)cyclopent[4,5]imidazo-[2,1-b] purin-4(3H)-one; and 5'-Methyl-2'(biphenylylmethyl)-3'-(phenylmethyl)spiro[cyclopentane-1,7'(8'H)-[3H]imidazo [2,1-b]purin]-4(5'H)-one).

Pharmaceutical compositions comprising PDE inhibitors which may be used in the method of the invention include all compositions wherein the PDE inhibitors are contained in an amount effective to achieve the intended purpose. In addition, the pharmaceutical compositions may contain suitable pharmaceutically acceptable carriers comprising excipients and auxiliaries which facilitate processing of the active compounds into preparations which can be used pharmaceutically. Suitable pharmaceutically acceptable vehicles are well known in the art and are described for example in Gennaro, et al., a standard reference text in this field. Gennaro, et al., of *Remington 's Pharmaceutical Sciences*, Part 8, 20th Ed., Merck Publishing Company, Easton, Pa. (2000). Pharmaceutically acceptable vehicles can be routinely selected in accordance with the mode of administration and the solubility and stability of the PDE inhibitors. For example, formulations for intravenous administration may include sterile aqueous solutions which may also contain buffers, diluents and other suitable additives. The use of biomaterials and other polymers for drug delivery, as well the different techniques and models to validate a specific mode of administration, are disclosed in the literature (Luo, et al., *Exp. Opin. Ther. Patents,* 11: 1395–1410 (2001); Cleland, et al., *Curr. Opin. Biotechnol.,* 12: 212–9 (2001)).

The PDE inhibitors may be administered by any means that achieves the intended purpose. For example, administration may be by a number of different routes including, but not limited to subcutaneous, intravenous, intradermal, intramuscular, intraperitoneal, intra-cerebral, intrathecal, intranasal, oral, rectal, transdermal, intranasal or buccal. Preferably the PDE inhibitors are administered orally.

Parenteral administration can be by bolus injection or by gradual perfusion over time. It is understood that the dosage administered will be dependent upon the age, health, and weight of the recipient, concurrent treatment, if any, frequency of treatment, and the nature of the effect desired. The total dose required for each treatment may be administered by multiple doses or in a single dose.

Preparations for parenteral administration include sterile aqueous or non-aqueous solutions, suspensions, and emulsions, which may contain auxiliary agents or excipients which are known in the art. Suitable formulations for parenteral administration include aqueous solutions of the active compounds in water-soluble form, for example, water-soluble salts. In addition, a suspension of the active compound as an oily injectable formulation may be administered.

Depending on the intended route of delivery, the PDE inhibitors may be formulated as injectable or oral compositions. The compositions for oral administration can take the form of bulk liquid solutions or suspensions, or bulk powders. More commonly, however, the compositions are presented in unit dosage forms to facilitate accurate dosing. The term "unit dosage forms" refers to physically discrete units suitable as unitary dosages for human subjects and other mammals, each unit containing a pre-determined quantity of active material calculated to produce the desired therapeutic effect, in association with a suitable pharmaceutical excipient. Typical unit dosage forms include pre-filled, pre-measured ampoules or syringes of the liquid compositions or pills, tablets, capsules or the like in the case of solid compositions. In such compositions, the PDE inhibitor is usually a minor component (from about 0.1 to about 50% by weight or preferably from about 1 to about 40% by weight) with the remainder being various vehicles or carriers and processing aids helpful for forming the desired dosing form.

Liquid forms suitable for oral administration may include a suitable aqueous or non-aqueous vehicle with buffers, suspending and dispensing agents, colorants, flavors and the like. Solid forms may include, for example, any of the following ingredients, or compounds of a similar nature: a binder such as microcrystalline cellulose, gum tragacanth or gelatine; an excipient such as starch or lactose; a disintegrating agent such as alginic acid, Primogel, or corn starch; a lubricant such as magnesium stearate; a glidant such as colloidal silicon dioxide; a sweetening agent such as sucrose or saccharin; or a flavoring agent such as peppermint, methyl salicylate, or orange flavoring.

Injectable compositions are typically based upon injectable sterile saline or phosphate-buffered saline or other injectable carriers known in the art.

The above-described components for orally administered or injectable compositions are merely representative. Further materials as well as processing techniques and the like are known to the skilled practitioner (Gennaro et al., 2000).

PDE inhibitors can also be administered in sustained release forms or from sustained release drug delivery systems. A description of representative sustained release materials is also known to the skilled practitioner (Karsa, et al. (ed.), *Encapsulation and Controlled Release*, Springer Verlag (1993); Yacobi, et al., *Oral Sustained Release Formulations: Design and Evaluation*, Pergamon Press (1998)).

By "effective amount", is meant an mount sufficient to achieve a concentration of PDE inhibitor which is capable of promoting follicular growth, with or without exogenous FSH or FSH replacements. Such concentrations can be routinely determined by those of skill in the art. The amount of the compound actually administered will typically be determined by a physician, in the light of the relevant circumstances, including the condition to be treated, the chosen route of administration, the actual compound administered, the age, weight, and response of the individual patient, the patient's endogenous FSH levels, and the like.

The expression "Pharmaceutically acceptable" is meant to encompass any carrier which does not substantially interfere with the effectiveness of the biological activity of the active ingredient and that is not toxic to the host to which is administered. For example, for parenteral administration, the above active ingredients may be formulated in unit dosage form for injection in vehicles such as saline, dextrose solution, serum albumin and Ringer's solution.

Besides the pharmaceutically acceptable carrier, compositions comprising PDE inhibitors can also comprise minor amounts of additives, such as stabilizers, excipients, buffers and preservatives.

Those of skill in the art are referred to U.S. Provisional Application Ser. No. 60/470,434 titled "Inhibitors of PDE Enzymes in Infertility." In said specification are described methods and composition of using PDE1 and/or PDE5 inhibitors for inducing ovulation and controlled ovarian hyperstimulation for in vitro fertilization. The entire document is incorporated herein by reference in its entirety for its teaching of inhibitors and protocols for administering such inhibitors. Any of the inhibitors disclosed therein may be used in the protocols of the present invention.

Particularly preferred PDE4 inhibitors that may be used herein include but are not limited to Roflumilast (methods and compositions for making this compound may be found in WO9501338), Piclamilast (methods of making the same are described in *J. Med. Chem.* 37:1696–1703 (1994)), ARIFLO (Cilomilast) (methods of making the same are described in *J. Med. Chem.* 41:821–835 (1998)), Mesopram (methods of making the same are WO97/15561), Filaminast (methods of making the same as described in EP0470 805 B1).

Delivery of a Combination of FSH and Phosphodiesterase Inhibitors to Induce Follicle Maturation In certain aspects, the methods of the invention contemplate the combined use of PDE 4 inhibitors with an FSH containing composition to increase follicle maturation. However, in addition to therapies based solely on the delivery of FSH/PDE 4 combination therapy, the methods of the present invention also contemplate combination therapy with a third composition that will enhance the follicle maturation effects of the treatment methods of the invention. Such a third composition may be a second PDE 4 inhibitor, or a second inhibitor of PDEs that is not specifically a PDE 4 inhibitor. For example, it is contemplated that the methods of the present invention may further involve administering a PDE 1 and/or a PDE 5 inhibitor. In addition, LH and/or hCG will also be provided in the methods of the present invention. It should be understood that a beneficial treatment may be achieved by administration of a PDE4 inhibitor alone.

To achieve the appropriate therapeutic outcome in the combination therapies contemplated herein, i.e., to achieve an increase in the number of ovulatable oocytes in the mammal that is being treated, one would generally administer to the subject the FSH and the PDE 4 inhibitor composition. These compositions would be provided in a combined amount effective to produce the desired therapeutic outcome. Typically, as indicated above, the FSH treatment is a course of daily administrations lasting between 7 to 12 days. The administration of the PDE 4 inhibitor may be administered concurrently with the FSH therapy. In such cases, the PDE 4 inhibitor and FSH may be contained in the same vial as a mixture. Alternatively, the PDE 4 inhibitor compositions may be taken prior to, or after, the FSH therapy. Furthermore, while the FSH therapy should preferably only be administered for any given period of 7 to 12 days during any given menstrual cycle, it is contemplated that the PDE 4 inhibitor may be administered continuously throughout the cycle as long as said administration does not cause deleterious side effects. Alternatively, the PDE 4 inhibitor may be administered less frequently than the FSH therapy.

In the other embodiments in which a third therapeutic agent is administered, the third agent may again be administered concurrently with one, other or both of the FSH and PDE 4 inhibitor therapeutic compositions or it may be administered prior to or after the FSH/PDE 4 therapies.

In embodiments all embodiments where two or more of the therapeutic compositions are administered separately, one would generally ensure that a significant period of time did not expire between the time of each delivery, such that the PDE 4-based agent and FSH administration and/or the third agent would still be able to exert an advantageously combined effect on the cell. In such instances, it is contemplated that one would administer all three compositions within about 12–24 hours of each other and, more preferably, within about 6–12 hours of each other, with a delay time of only about 12 hours being most preferred. In some situations, it may be desirable to extend the time period for treatment significantly, however, where several days (2, 3, 4, 5, 6 or 7) lapse between the respective administrations. Likewise, where the entire protocol is repeated, it may be desirable to either repeat the protocol through consecutive cycles or alternatively, the physician may determine that it is desirable to allow 1, 2 3, 4 or more cycles lapse between two treatment protocols of the present invention.

Patient Selection and Monitoring

The patients that receive the treatments of the invention are female patients, preferably between the ages of 20 and 45. Patient selection for the methods of the present invention may employ the same parameters as described in the PDR™ entries for use of FSH based therapies described above. For example, prior to treatment the patient is subjected to a thorough gynecologic examination and endocrinologic evaluation, including an assessment of pelvic anatomy. Primary ovarian failure should be excluded by determining the basal serum gonadotropin levels and it should be ensured that the patient is not pregnant.

Throughout the treatment regimens of the present invention, the patient should be assessed prior to, during, and after, the therapy to monitor for the signs of OHSS. The symptoms of OHSS include but are not limited to abdominal pain, abdominal distention, gastrointestinal symptoms including nausea, diarrhea, severe ovarian enlargement, weight gain, dyspnea amd oliguria. Clinically, the symptom manifests in hypovolemia, hemoconcentration, electrolytic imbalance, ascites, hemoperitoneum, pleural effusions, hydrothorax acute pulmonary distress and thromboembolism. In the event that symptoms of OHSS occur during the administration of the FSH-based therapy or any other agent being administered for stimulation of follicular maturation, the administration should cease and the subject should be placed under medical supervision to determine whether hospitalization or other intervention is necessary. Other symptoms that may be used to monitor the FSH-based therapy include changes in vaginal cytology, appearance and volume of vaginal mucous, Spinnbarkeit and feming of cervical mucus. These latter symptoms are indicative of the estrogenic effect of the therapy, and should be monitored because administration FSH will stimulate estrogen production. Preferably these estrogenic effects should be monitored in conjunction with more direct determinations of follicle development such as, e.g., determination of serum estradiol and ultrasonigraphy.

The clinical manifestations of ovulation, other than pregnancy, may be obtained either through a direct or an indirect measure of progesterone production. Such indicia include: a rise in basal body temperature, increase in serum progesterone, menstruation following a shift in body temperature. In conjunction with the above indicators of progesterone production, sonographic visualization of the ovaries may be used to assist in determining if ovulation has occurred. Such monographic monitoring may include evaluating fluid in the cul-de sac, ovarian stigmata and the presence of collapsed follicles. Sonographic determinations also will assist in determining whether the ovaries are enlarged in OHSS.

Use of Inhibitors of PDE to Induce Ovulation

The PDE inhibitor is preferably administered to the patient during a stimulatory phase of from at or about two to at or about ten days, more preferably at or about three to at or about eight days, preferably starting on at or about day 2 or day 3 of the menstrual cycle. For OI, administration is preferably continued until there is one follicle of mean diameter greater than or equal to about 16–18 mm (and preferably not more than two follicles of mean diameter greater than 14 mm). Administration of the PDE inhibitor preferably stops on the day that hCG is administered to begin the ovulatory phase.

For ovulation induction, the PDE inhibitor may be administered alone (acting with endogenous FSH), or it may be administered in conjunction with FSH or an agent having FSH activity, or stimulating endogenous FSH release. The administration of the PDE inhibitor in conjunction with another follicle stimulating agent may be simultaneous, separate or sequential. Agents having FSH activity include recombinant and urinary FSH, and also FSH mixed with varying amounts of LH, such as hMG. Agents having FSH activity also include analogues of FSH, for example, CTP-FSH [a long-acting modified recombinant FSH, consisting of the wild type α-subunit and a hybrid α-subunit in which the carboxy terminal peptide of hCG has been fused to the C-terminal of the β-subunit of FSH, see LaPolt, et al., *Endocrinology*, 131:2514–2520 (1992); or Klein, et al., *Human Reprod.* 18:50–56 (2003)]. Also included is single-chain FSH-CTP, a single chain molecule, consisting of the following sequences (from N-terminal to C-terminal):

| βFSH | βhCG-CTP(113–145) | αFSH |
| --- | --- | --- | wherein βFSH signifies the β-subunit of FSH, βhCG CTP (113–145) signifies the carboxy terminal peptide of hCG and αFSH signifies the α-subunit of FSH, as described by Klein et al., *Fertility & Sterility;* 77:1248–1255 (2002). Agents which stimulate or lead to endogenous FSH production or release include clomiphene citrate and aromatase inhibitors, such as, for example, Letrozole, YM-511, Anastrozole or Fadrozole. The use of these molecules in OI is disclosed, for example, in WO 02/083241 and WO 02/083239.

In a preferred regimen for OI, the patient is administered a PDE inhibitor, preferably a PDE 1 and/or 5 inhibitor, more preferably a selective PDE 1 and/or 5 inhibitor, most preferably a PDE 1 inhibitor, and most particularly preferably a selective PDE 1 inhibitor, preferably starting at or about day three after menstruation. This marks the beginning of the stimulatory phase. Administration of PDE inhibitor is continued, preferably on a daily basis, but may also be twice daily or on alternate days, or even in a single dose. The progress of developing follicles may be monitored by ultrasound. Follicular growth is judged to be sufficient when there is one follicle of mean diameter greater than or equal to at or about 16–18 mm, and preferably not more than two follicles with mean diameter greater than 16 mm, an ovulation trigger is given (marking the end of the stimulatory phase and the beginning of the ovulatory phase), using an agent having LH-activity, for example hCG (usually 5,000 to 10,000 IU), LH (25,000 to 70,000 µl) or a PDE IV inhibitor (as described in published US patent application no. 2002/0103106 A1). The patient is then instructed to have intercourse 24 to 36 hours after administration of the ovulation trigger. Alternatively fertilization may be by intrauterine insemination (IUI).

In patients having non-stimulated and non-down-regulated (natural cycle) serum FSH levels below at or about 2 IU/liter (measured at or about day 2 after menstruation), ovulation induction should preferably be carried out using a PDE inhibitor in conjunction with FSH or agents having FSH activity, or agents stimulating an endogenous release of FSH. The dose of FSH required will be less than that required in patients who do not receive a PDE inhibitor to achieve the same or better response, in terms of number of follicles having a mean diameter of at or about 16 mm or greater on day 8 of stimulation.

When FSH or an agent having follicle-stimulating activity, or agents stimulating an endogenous release of FSH are used in OI, administration of FSH may be started before or after administration of the PDE inhibitor, or the two agents may be administered starting simultaneously. Preferably administration of FSH starts simultaneously with administration of the PDE inhibitor, or at or about one day before administration of the PDE inhibitor. The stimulatory phase begins with the first administration of FSH or PDE inhibitor, whichever is first, or if only a PDE inhibitor is used, on the day that administration begins.

Use of PDE Inhibitors for Controlled Ovarian Hyperstimulation

For controlled ovarian hyperstimulation (COH) for ART, a PDE inhibitor can be used without exogenous FSH (or an agent having follicle-stimulating activity), according to the invention, to enhance endogenous FSH levels, resulting in controlled ovarian hyperstimulation, and the development of multiple ovulatory follicles. If the patient has non-stimulated and non-down-regulated (natural cycle) serum FSH levels below at or about 5 IU/liter (measured at or about day 2 after menstruation), COH should preferably be carried out using a PDE inhibitor in conjunction with FSH or an agent having follicle-stimulating activity, or agents stimulating an endogenous release of FSH, such as those mentioned above. When FSH or an agent having follicle-stimulating activity, or agents stimulating an endogenous release of FSH are used in COH, administration of FSH may be started before or after administration of the PDE inhibitor, or the two agents may be administered starting simultaneously. Preferably administration of FSH starts simultaneously with administration of the PDE inhibitor, or at or about one day before administration of the PDE inhibitor. The stimulatory phase begins with the first administration of FSH or PDE inhibitor, whichever is first, or if only a PDE inhibitor is used, on the day that administration begins.

In a preferred regimen for COH, the patient is first down-regulated to suppress endogenous luteinizing hormone (LH), by administration of a gonadotrophin releasing hormone (GnRH) agonist starting in the luteal phase of a menstrual cycle (usually on about day 20 of a menstrual cycle). Suppression of ovarian function usually takes from 8 to 21 days with a GnRH agonist, and may be monitored by monitoring LH or estradiol levels (LH<5 IU/L, $E_2$<50 pg/ml generally indicate adequate suppression). GNRH agonists include, for example, Buserelin, Goserelin, Leuprorelin, Triptorelin and Nafarelin. Down-regulation is followed by a stimulatory phase in which follicular development is stimulated using a PDE inhibitor, preferably a PDE 1 and/or 5 inhibitor, more preferably a selective PDE 1 and/or 5 inhibitor, more preferably a PDE 1 inhibitor, most preferably a selective PDE 1 inhibitor. The PDE inhibitor may be used alone or in conjunction with administration of follicle stimulating hormone (FSH) or an agent having FSH activity or an agent stimulating endogenous FSH release. The day on which stimulation is started with a PDE inhibitor or FSH, whichever is started first, is defined as the start of the stimulatory phase. The use of a PDE inhibitor permits the use of lower doses of FSH (or equivalents) than would be used in the same patient if FSH alone were used for COH, while achieving the same or better follicular response, in terms of number of follicles having a mean diameter of at or about 16 mm or greater on day 8 of stimulation. Preferably the dose of FSH used when a PDE inhibitor is administered will be less than or equal to at or about 75% of the dose of FSH that would be required in the same patient without the PDE inhibitor, in order to achieve the same follicular response, more preferably the dose of FSH will be less than or equal to at or about 50% of the dose of FSH that would be required in the same patient without the PDE inhibitor, most preferably the dose of FSH will be less than or equal to at or about 30% of the dose of FSH that would be required in the same patient without the PDE inhibitor.

When a PDE inhibitor is administered, the dose of FSH will preferably be at or about 25–600 IU FSH daily, more preferably at or about 50–450 IU daily, most preferably 50–300 IU daily. Stimulation with PDE inhibitor in the absence or presence of exogenous FSH (or equivalents) is preferably continued until follicular growth is judged to be sufficient, i.e. when there are at least 3 follicles with a mean diameter greater than at or about 16 mm (preferably one of 18 mm), while continuing to administer the GNRH antagonist. An ovulation-triggering dose of an agent having LH-activity (e.g. 5,000–10,000 IU of hCG) is then administered, as described for 01. Oocyte recovery is timed for 36–38 hours after the ovulation trigger. Oocytes are usually recovered from pre-ovulatory follicles, by aspiration. Oocytes are graded, fertilized in vitro, and embryos are selected for transfer to the uterus approximately 72–96 hours after collection.

In another preferred regimen for COH, a GnRH antagonist is used. Without the administration of a GnRH agonist, follicular stimulation is started, usually on day 1, 2 or 3 after spontaneous or induced menstruation, with a PDE inhibitor, preferably a PDE 1 and/or 5 inhibitor, more preferably a selective PDE 1 and/or 5 inhibitor, more preferably a PDE 1 inhibitor, most preferably a selective PDE 1 inhibitor, in conjunction with administration of follicle stimulating hormone (FSH) or an agent having FSH activity or an agent stimulating endogenous FSH release. Then a GnRH-antagonist is administered starting on about day 6 after menses. GnRH antagonists include, for example, Cetrorelix, NaI-Glu, Antide, Ganirelix, Azaline B and Antarelix. Stimulation with PDE inhibitor and FSH (or equivalents) is continued until there are at least 3 follicles with a mean diameter greater than 16 mm (preferably one of 18 mm). An ovulation triggering dose of an agent having LH-activity is then administered, as described for 01. The GNRH antagonist is administered up until the day of ovulation triggering.

In an alternate preferred regimen for COH, follicular stimulation is started by administration of an aromatase inhibitor, preferably on days 3 to 6 after menstruation, in conjunction with a PDE inhibitor, preferably a PDE 1 and/or 5 inhibitor, more preferably a selective PDE 1 and/or 5 inhibitor, more preferably a PDE 1 inhibitor, most preferably a selective PDE 1 inhibitor. On or about day 6, a GnRH antagonist is given, the aromatase inhibitor is stopped and injections of FSH are started. PDE inhibitor, FSH and GnRH antagonist administration are continued until the ovulation-triggering dose of hCG is administered.

Use of the Oocytes for In Vitro Fertilization

The methods of the present invention are used to produce hCG ovulatable oocytes. The combined PDE 4 inhibitor/FSH hormonal treatment can be a short or long treatment, with or without pituitary down regulation, or with and without the use of GnRH antagonist; and with or without the use of hCG. The combined PDE 4 inhibitor/FSH therapy is administered until the follicles have matured sufficiently to be medium to full size follicles (size 10 to 25 mm, preferential 16 to 20 mm follicles). The oocytes from such follicles may be allowed to ovulate in vivo, either through the hCG surge from the patient's own menstrual cycle if the endogenous gonadotropin hormone production has not be suppressed, or by supplying to the patient an exogenous injection of hCG (e.g., 5,000 to 10,000 Units).

Alternatively, medium to full size follicles (size 10 to 25 mm, preferential 16 to 20 mm follicles) are harvested by aspiration under ultrasound guidance in order to be fertilized in vitro. The aspirated fluid is searched for cumulus oocytes complexes (COC) and once identified under the stereomicroscope (with or without the use of embryo filters), the COC is placed in culture. A wide variety of oocyte culture media or media components known to those of skill in the art. Such media may but does not necessarily have to contain human serum albumin (HSA).

Following or during in vitro culture, the oocytes may be fertilized by conventional IVF or by intracytoplasmatic sperm injection (ICSI) or by any other conventional fertilization methods leading to fertilized zygotes. The developing embryo may be transferred on day 1 to day 6 after fertilization, preferentially on day 2 to 3, either as single egg transfer or multiple egg transfer.

The patient can receive progesterone and/or estrogen therapy before and after the egg transfer in individually designed protocols to prime and sustain appropriate receptive endometrial lineage.

The methods of the present invention produce an increased number of ovulatable oocytes for use in IVF procedures such as those described above. However, it may be that the methods of the present invention will also be useful in vitro maturation of immature oocytes. In such embodiments, the oocytes are retrieved from antral follicles of the ovaries before being exposed to the mid-cycle surge of gonadotropins and are therefore characterized as immature or not fully matured oocytes. Human oocytes as well as oocytes from other species will be recognized as having little or no cumulus expansion, a germinal vesicle and no polar bodies, and will readily be recognized as such by persons skilled in IVF-treatments. One potential use of the therapies of the present invention would be to replace CC or FSH in non-IVF protocols where such treatment may increase the maturation of a single or dominant follicle for natural fertilization rather than for harvesting for assisted reproductive technologies.

While much of the discussion herein has described the maturation of human follicles, it is contemplated that the methods of the present invention may be employed for producing oocytes for IVF of other mammals, such as a pet (e.g. a cat, a dog, or a guinea pig); or a zoo animal (e.g. a primate). In further preferred embodiments, the mammal is part of the industry, preferably a farm animal such as cattle, a horse, a pig, a mink, a goat, or a sheep. In the most preferred embodiments, the mammal is a human being. For in vitro maturation, the immature oocytes are treated in vitro with a PDE inhibitor or a PDE inhibitor and a gonadotropin hormone, in order to produce mature oocytes that can be fertilized.

Pharmaceutical Compositions and Kits

Pharmaceutical compositions for administration according to the present invention can comprise at least one gonadotropin hormone, preferably FSH according to the present invention in a pharmaceutically acceptable form optionally combined with a pharmaceutically acceptable carrier. These compositions can be administered by any means that achieve their intended purposes. Individualized amounts and regimens for the administration of FSH compositions for the stimulation of follicle maturation using the methods of the present invention can be determined readily by those with ordinary skill in the art using the guidance provided by the Physician's Desk Reference for the use of such compositions in treating anovulatory disorders and for their use in assisted reproduction technologies. As discussed above, those of skill in the art could initially employ amounts and regimens of FSH currently being used in such medical contexts. To this effect, those skilled in the art are specifically referred to each of the entries in the Physician's Desk Reference discussed above and those entries are incorporated herein by reference in their entireties for teaching methods and compositions for the administration of agents such as Fertinex™, Gonal F™, Bravelle™ and the like discussed herein above. Each of those entries in the Physician's Desk Reference provide exemplary guidance as to types of formulations, routes of administration and treatment regimens that may be used in administering FSH. Any of the protocols, formulations, routes of administration and the like described therein can readily be modified for use in the present invention.

Compositions within the scope of this invention include all compositions comprising at least one PDE 4 inhibitor according to the present invention in an amount effective to achieve its intended purpose of stimulating, inducing or otherwise increasing the number of ovulatable oocytes in an animal, either when administered alone or more preferably, when administered in combination with a low dose of FSH. The PDE 4 inhibitors and/or the other active agents used in the methods of the present invention may be administered by any means normally employed for such administration. Those of skill are particularly referred to U.S. Patent Application No. 60/470,434 titled "Inhibitors of PDE Enzymes in Infertility," U.S. Patent Publication No. 20020103106 and PCT/EP01/14730, each of which describe amounts and routes of administration of PDE inhibitors in fertility related applications. Most preferably, the compositions used in the present invention are administered orally.

While individual needs vary, determination of optimal ranges of effective amounts of each component is within the skill of the art. Typical dosages of the FSH comprise about 5 IU FSH/day to about 75 IU FSH/day, for a 7 to 12 day period. Typical doses of he PDE 4 inhibitor may vary from about 5 mg/day to about 100 mg/day or more. While continuous, daily administration of the PDE 4 is contemplated, it may be desirable to cease the PDE 4 administration at the same time as the FSH administration is ceased. Of course, while FSH therapy is traditionally given for a period of 7 to 12 days, it may be that in the context of the present invention only a single or a few low doses of FSH are needed to effect the therapeutically beneficial outcome of increased follicle maturation. Therapy should be halted in the event that symptoms of OHSS are observed.

It is understood that the suitable dose of a composition according to the present invention will depend upon the age, health and weight of the recipient, kind of concurrent treatment, if any, frequency of treatment, and the nature of the effect desired. However, the most preferred dosage can be tailored to the individual subject, as is understood and determinable by one of skill in the art, without undue experimentation. This typically involves adjustment of a standard dose, e.g., reduction of the dose if the patient has a low body weight.

As discussed above, the total dose required for each treatment may be administered in multiple doses or in a single dose. The compositions may be administered alone or in conjunction with other therapeutics directed to the disease or directed to other symptoms thereof.

As is apparent from the disclosure presented herein, in a broad aspect the present application contemplates clinical application of a combination therapy comprising a first composition that contains a PDE inhibitor, and a second composition that contains FSH. Therefore, the compositions should be formulated into suitable pharmaceutical compositions, i.e., in a form appropriate for in vivo applications in such combination therapies. Generally, this will entail preparing compositions that are essentially free of pyrogens, as well as other impurities that could be harmful to humans or animals. The FSH formulations may be formulated akin to the currently available FSH preparations discussed herein throughout. The PDE 4 inhibitor formulations may be formulated similarly to e.g., formulations of Viagra™, which is a well-known PDE 5 inhibitor.

One will generally desire to employ appropriate salts and buffers to render the compositions stable and allow for uptake of the compositions at the target site. Generally the hormone compositions of the invention are provided in lyophilized form to be reconstituted prior to administration and the PDE 4 inhibitor compositions are likely formulated into tablet form. Buffers and solutions for the reconstitution of the hormones may be provided along with the pharmaceutical formulation to produce aqueous compositions of the present invention for administration. Such aqueous compositions will comprise an effective amount of each of the therapeutic agents being used, dissolved or dispersed in a pharmaceutically acceptable carrier or aqueous medium. Such compositions also are referred to as inocula. The phrase "pharmaceutically or pharmacologically acceptable" refers to molecular entities and compositions that do not produce adverse, allergic, or other untoward reactions when administered to an animal or a human. As used herein, "pharmaceutically acceptable carrier" includes any and all solvents, dispersion media, coatings, antibacterial and antifungal agents, isotonic and absorption delaying agents and the like. The use of such media and agents for pharmaceutically active substances is well known in the art. Except insofar as any conventional media or agent is incompatible with the therapeutic compositions, its use in therapeutic compositions is contemplated. Supplementary active ingredients also can be incorporated into the compositions.

The active compositions of the present invention include classic pharmaceutical preparations of FSH, which have been discussed herein as well as those known to those of skill in the art. PDE 4 inhibitors also are known to those of skill in the art. Administration of these compositions according to the present invention will be via any common route so long as the target tissue is available via that route. Most commonly, these compositions are formulated for oral administration. However, other conventional routes of administration, e.g., by subcutaneous, intravenous, intradermal, intramusclar, intramammary, intraperitoneal, intrathecal, intraocular, retrobulbar, intrapulmonary (e.g., term release), aerosol, sublingual, nasal, anal, vaginal, or transdermal delivery, or by surgical implantation at a particular site also may be used particularly when oral administration is problematic. The treatment may consist of a single dose or a plurality of doses over a period of time.

The active compounds may be prepared for administration as solutions of free base or pharmacologically acceptable salts in water suitably mixed with a surfactant, such as hydroxypropylcellulose. Dispersions also can be prepared in glycerol, liquid polyethylene glycols, and mixtures thereof and in oils. Under ordinary conditions of storage and use, these preparations contain a preservative to prevent the growth of microorganisms.

The pharmaceutical forms suitable for injectable use include sterile aqueous solutions or dispersions and sterile powders for the extemporaneous preparation of sterile injectable solutions or dispersions. In all cases the form must be sterile and must be fluid to the extent that easy syringability exists. It must be stable under the conditions of manufacture and storage and must be preserved against the contaminating action of microorganisms, such as bacteria and fungi. The carrier can be a solvent or dispersion medium containing, for example, water, ethanol, polyol (for example, glycerol, propylene glycol, and liquid polyethylene glycol, and the like), suitable mixtures thereof, and vegetable oils. The proper fluidity can be maintained, for example, by the use of a coating, such as lecithin, by the maintenance of the required particle size in the case of dispersion and by the use of surfactants. The prevention of the action of microorganisms can be brought about by various antibacterial and antifungal agents, for example, parabens, chlorobutanol, phenol, sorbic acid, thimerosal, and the like. In many cases, it will be preferable to include isotonic agents, for example, sugars or sodium chloride. Prolonged absorption of the injectable compositions can be brought about by the use in the compositions of agents delaying absorption, for example, aluminum monostearate and gelatin.

Sterile injectable solutions are prepared by incorporating the active compounds in the required amount in the appropriate solvent with various of the other ingredients enumerated above, as required, followed by filtered sterilization. Generally, dispersions are prepared by incorporating the various sterilized active ingredients into a sterile vehicle which contains the basic dispersion medium and the required other ingredients from those enumerated above. In the case of sterile powders for the preparation of sterile injectable solutions, the preferred methods of preparation are vacuum-drying and freeze-drying techniques which yield a powder of the active ingredient plus any additional desired ingredient from a previously sterile-filtered solution thereof.

As used herein, "pharmaceutically acceptable carrier" includes any and all solvents, dispersion media, coatings, antibacterial and antifungal agents, isotonic and absorption delaying agents and the like. The use of such media and agents for pharmaceutical active substances is well known in the art. Except insofar as any conventional media or agent is incompatible with the active ingredient, its use in the therapeutic compositions is contemplated. Supplementary active ingredients also can be incorporated into the compositions.

The compositions of the present invention may be formulated in a neutral or salt form. Pharmaceutically-acceptable salts include the acid addition salts (formed with the free amino groups of the protein) and which are formed with inorganic acids such as, for example, hydrochloric or phosphoric acids, or such organic acids as acetic, oxalic, tartaric, mandelic, and the like. Salts formed with the free carboxyl groups also can be derived from inorganic bases such as, for example, sodium, potassium, ammonium, calcium, or ferric hydroxides, and such organic bases as isopropylamine, trimethylamine, histidine, procaine and the like.

Upon formulation, solutions will be administered in a manner compatible with the dosage formulation and in such amount as is therapeutically effective. The formulations are easily administered in a variety of dosage forms such as injectable solutions, drug release capsules and the like. For parenteral administration in an aqueous solution, for example, the solution should be suitably buffered if necessary and the liquid diluent first rendered isotonic with sufficient saline or glucose. These particular aqueous solutions are especially suitable for intravenous, intramuscular, subcutaneous and intraperitoneal administration.

"Unit dose" is defined as a discrete amount of a therapeutic composition dispersed in a suitable carrier. Examples of preferred doses of the FSH and the PDE inhibitors have been discussed above. Parenteral administration of one or both of the therapeutic compounds may be carried out with an initial bolus followed by continuous infusion to maintain therapeutic circulating levels of drug product. Those of ordinary skill in the art will readily optimize effective dosages and administration regimens as determined by good medical practice and the clinical condition of the individual patient.

The frequency of dosing will depend on the pharmacokinetic parameters of the agents and the routes of administration. The optimal pharmaceutical formulation will be determined by one of skill in the art depending on the route of administration and the desired dosage. See, for example, *Remington's Pharmaceutical Sciences,* 18th Ed., Mack, Easton, Pa. (1990), incorporated herein by reference. Such formulations may influence the physical state, stability, rate of in vivo release and rate of in vivo clearance of the administered agents. Depending on the route of administration, a suitable dose may be calculated according to body weight, body surface areas or organ size. Further refinement of the calculations necessary to determine the appropriate treatment dose is routinely made by those of ordinary skill in the art without undue experimentation, especially in light of the dosage information and assays disclosed herein as well as the pharmacokinetic data observed in animals or human clinical trials.

Appropriate dosages may be ascertained through the use of established assays for determining blood levels in conjunction with relevant dose response data. The final dosage regimen will be determined by the attending physician, considering factors which modify the action of drugs, e.g., the drug's specific activity, severity of the damage and the responsiveness of the patient, the age, condition, body weight, sex and diet of the patient, the severity of any infection, time of administration and other clinical factors. As studies are conducted, further information will emerge regarding appropriate dosage levels and duration of treatment for specific diseases and conditions.

It will be appreciated that the pharmaceutical compositions and treatment methods of the invention may be useful in fields of human medicine and veterinary medicine. Thus the subject to be treated may be a mammal, preferably human or other animal. For veterinary purposes, subjects include for example, farm animals including cows, sheep, pigs, horses and goats, companion animals such as dogs and cats, exotic and/or zoo animals, laboratory animals including mice, rats, rabbits, guinea pigs, and hamsters; and poultry such as chickens, turkeys, ducks, and geese.

The present invention also contemplated kits for use in the treatment of fertility disorders. Such kits include at least a first composition comprising an FSH in a pharmaceutically acceptable carrier, and a second composition comprising at least one PDE 4 inhibitor in a pharmaceutically acceptable carrier. The kits may additionally comprise solutions or buffers for effecting the delivery of the first and second compositions. The kits may further comprise additional compositions which contain further PDE inhibitors e.g., additional PDE 4 inhibitors or additional PDE 1 or PDE 5 inhibitors and/or further hormones such as e.g., hCG, LH and the like. The kits may further comprise catheters, syringes or other delivering devices for the delivery of one or more of the compositions used in the methods of the invention. The kits may further comprise instructions containing administration protocols for the therapeutic regimens.

EXAMPLES

The following examples are included to demonstrate preferred embodiments of the invention. It should be appreciated by those of skill in the art that the techniques disclosed in the examples that follow represent techniques discovered by the inventor to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

Materials & Methods

Animals: Immature Sprague Dawley CD (SD) BR female rats, weighing 36–39 g on receipt were used. The animals were housed in a room under the following constant environmental conditions: temperature 22° C. ±2, relative humidity 55%±10, 15–20 air changes per hour (filtered on HEPA 99.99%) and artificial light with a 12-hour circadian cycle (7h00–19h00).

For the entire duration of the study the rats were kept in wire cages (cm. 40.5×38.5×18 h) with stainless steel feeders and fed on a standard pelleted diet (4RF21 produced by Charles River Italia's licensee Mucedola s.r.l.) and water "ad libitum".

Chemicals: Human recombinant follicle stimulating hormone (r-hFSH) and human recombinant chorionic gonadotrophin (r-hCG) were supplied by Laboratoires Serono Aubonne (LSA, Aubonne, Switzerland). Test compounds were either synthesized based on published compound synthetic methods or purchased from commercial sources. In particular, those of skill are referred to WO9501338 which teaches methods of making Roflumilast, J. Med. Chem. 1994, 37,1696–1703 for a detailed description of methods of making Piclamilast, J. Med. Chem. 1998, 41,821–835 for a description of methods for making ARIFLO (Cilomilas), WO97/15561 for methods of making Mesopram, and EP0470 805 B1 for methods of making Filaminast. Such methods may be modified for producing other PDE inhibitors. Other test compounds (Dipyridamole, Zaprinast, Sildenafil) were either synthesized based on published compound synthesis methods or purchased from commercial sources. In addition, U.S. Patent Application No. 60/470,434 titled "Inhibitors of PDE Enzymes in Infertility," U.S. Patent Publication No. 20020103106, and PCT/EP01/14730 are incorporated herein by reference as teaching other related such compounds that may be used herein.

In vivo Rat Follicle Maturation Assay: Immature female rats arrived on Friday of the week prior to the experimentation at 18–19 days of age along with a lactating female (ten pups per lactating female). All rats were weaned from the mother on the following Monday (21–22 days old) and were randomly sorted into the experimental groups (6–8 animals/group).

The rats were subcutaneously injected (in the scruff of the neck) twice a day for two days (first injection: 8.30–9.00 and second injection 15.30–16.00) with r-hFSH or vehicle (PBS) at a volume of 250 μL/injection. The doses of FSH injected were either suboptimal (606 ng/rat total dose split over four injections; indicated as 'Low FSH' in Figures) or high (2424.8 ng/rat total dose split over 4 injections; indicated as 'High FSH' in Figures) as a positive control.

In addition to the above injections, rats were also injected subcutaneously with the test compounds or vehicle twice a day for 2 days at indicated doses (mg/kg/injection), concomitantly with the FSH injections. These compounds were diluted in either NP3S (n-methyl-2-pyrrolidone 5%, polyethylene glycol 400 30%, polyethylene glycol 200 25%, propylene glycol 20%, saline 20%) or aqueous vehicles. Therefore, the total number of injections received by each rat to promote follicle growth was eight, including four injections of r-hFSH or r-hFSH vehicle plus four injections of test compound or test compound vehicle.

On day 2 of the experiment and along with the final r-hFSH injection, the rats were also treated with a single subcutaneous injection of r-hCG (1430 ng/rat) to induce ovulation of all or most of the matured follicles.

At 10:00 of the morning following r-hCG administration, rats were euthanized by $CO_2$ asphyxia. The animals were laid on their backs and undersides were sprayed with ethanol to both sterilize and keep the hair from falling out in the dissection of the animals. With the aid of scissors and forceps the skin and muscle were cut starting from the pubic symphisis with aboral-oral direction up to the sternum. The internal organs were exposed and the intestine was moved to one side. The ovaries, the uterine horns and the uterus body were removed clipping away the fat and the connective tissue. The entire reproductive tract was then placed into a well in a 24 well plate containing PBS (1 animal/well).

After all the animals were sacrificed and the ovaries were harvested, the oviducts were gently removed from the ovaries, dipped in PBS and placed on a microscope slide. The ovary was then taken out, cleaned and placed into PBS for weighing (the uterus was discarded).

Pairs of oviducts were placed on one slide and then a slide was placed on top of the first slide using a piece of tape to secure the frosted ends of the slides together. After the oviducts were placed on the bottom slide, the top slide was folded over and the non-frosted end was then taped, compressing the oviducts between the two slides. The oviducts were then examined by a light microscope under contrast phase conditions (at a minimum of 40× magnification) and the ova, if any, present in the two ampullae for each rat were counted. The results were graphed as the average number of oocytes ovulated per rat. Error bars reflect the standard error of the mean for each group.

Example 1

Ovulation Induction Using Various Pde Inhibitors in Combination with Low-dose FSH Experiments were conducted according to the In Vivo Rat Follicle Maturation Assay, described above. In one experiment, ovaries were harvested from rats at midday of the second day of treatment for histological analysis, prior to the last set of injections. These rats received only the first three doses of FSH and test compound prior to euthanasia and organ harvest. The secondary follicles were evaluated by counting the total number of secondary follicles: including both small follicles (those at any intermediate stage of maturation, having a multilayered granulosa with the first, scattered vacuoles, but without an antrum) and antral follicles (those having antral dilation, with an external diameter of around 500 microns, or higher, with or without thinning of the granulosa cell layer). The antral follicles ($\geq 500$ mcm) were also counted separately.

Data Analysis

The proportion of ovulating animals, the average number ova present in the ampulla per rat, and the average ovary weight were calculated from the single values in each experimental group and the relevant graphs were plotted. All Figures demonstrate mean plus/minus standard error of the mean. In the Figures, the number above the standard error bars indicates the number of rats in the group that had one or more ovulated ova compared to the total number of rats in the group, for example X/Y means that X rats out of a total of Y had one or more ovulated ova.

Compounds Tested

The following compounds were tested in the above protocols:

(i) Zaprinast (inhibitor of PDE's 1, 5, 6, 7, 9, 10, 11);
(ii) Sildenafil (inhibitor of PDE's 1, 5 and 6);
(iii) Dipyridamole (Inhibitor of PDE's 5, 6, 7, 8, 10, 11);
(iv) Tadalafil (an inhibitor of PDE's 5 and 6)
(v) Compound no. 31 ((6aR,9aS)-2-(Biphenylylmethyl)-5,6a,7,8,9,9a-hexahydro-5-methyl-3(phenylmethyl)cyclopent[4,5]imidazo-[2,1-b]purin-4(3H)-one) (an inhibitor of PDE1)
(vi) Compound no. 33 (5'-Methyl-2'(biphenylylmethyl)-3'-(phenylmethyl)spiro[cyclopentane-1,7'(8'H)-[3H]imidazo[2,1-b]purin]-4(5'H)-one) (an inhibitor of PDE1)

These molecules have been shown to exhibit the following selectivity for various PDE enzymes:

| Molecule | IC$_{50}$ PDE1 | IC$_{50}$ PDE5 | IC$_{50}$ PDE6 [**] | | IC$_{50}$ PDE3 [*] |
|---|---|---|---|---|---|
| Zaprinast | 9400 nM[ref 1] | 2000 nM[ref 1] | | | >100,000 nM[ref 1] |
| Sildenafil | 260 nM[ref 1] | 3.0–3.6 nM[ref 1] | Selectivity for PDE5 10-fold > PDE6[ref 2] | | 65,000 nM[ref 1] |
| Tadalafil | >30,000 nM[ref 3] | 6.7 nM[ref 3] | Selectivity for PDE5 187-193- fold > PDE6[ref 3] | | >100,000 |
| Compound no. 31 | 0.07 nM[ref 4] | 305 nM[ref 4] | | | 3500 |
| Compound no. 33 | 0.6 nM[ref 4] | 200 nM[ref 4] | | | 7000 | ref [1]Terrett, et al., Biooganic and Medicinal Chemistry Letters, 6(15): 1819–1824 (1996).
ref [2]Physicians Desk Reference, 57th Ed., 2003
ref [3]Corbin, et al., International Journal of Clinical Practice, 56(6): 453–459 (2002).
ref [4]Ahn, et al., J. Med. Chem., 40: 2196–2210 (1997).
* PDE3 is expressed in oocytes, preferred PDE inhibitors are selective against PDE3, because inhibition of PDE3 may lead to non-optimal oocyte growth. Wiersma, et al., J. Clin. Invest., 102(3): 532–537 (1998).
** PDE6 is expressed in the rods and cones of the retina; PDE6 inhibition may cause mild visual disturbances; preferred PDE inhibitors are selective against PDE6 (i.e. preferably having at least at or about a 100 fold greater ability to inhibit PDE1 or PDE5 as compared to PDE6);

Results

Figure 1:
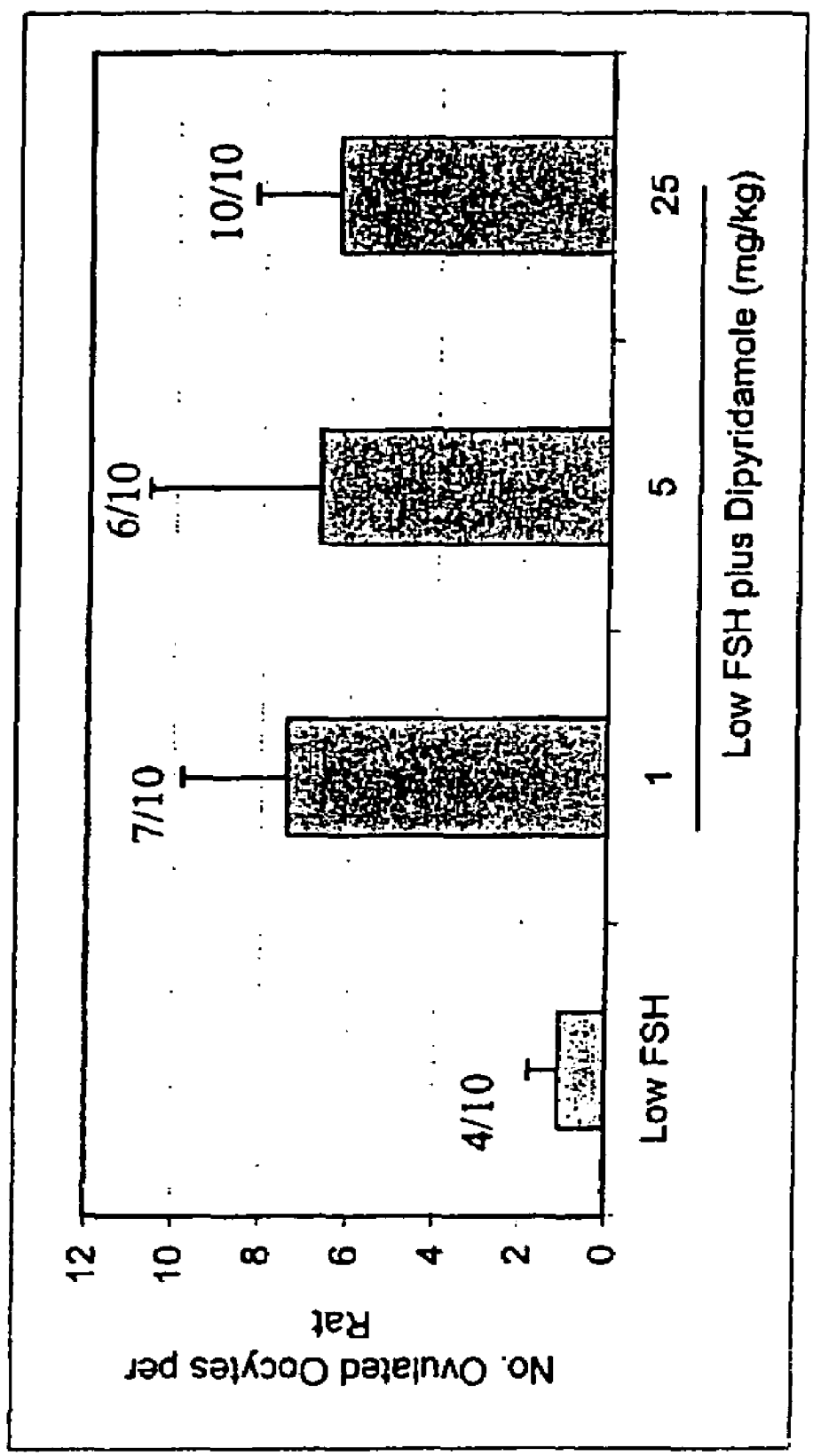
FIG. 1 shows the number of oocytes ovulated per rat in immature female rats treated with a suboptimal dose of FSH ("Low FSH": 151.5 ng×4 per rat) and rats treated with the suboptimal dose of FSH ("Low FSH") plus Dipyridamole (1, 5, 25 mg/kg×4 per rat).

Dipyridamole (an inhibitor of PDE's 5, 6, 7, 8, 10, 11) was administered at doses of 1, 5 and 25 mg/kg×4 injections per rat (subcutaneously) in NP3S with the Low Dose of FSH, resulting in an increase in the number of ovulated oocytes per rat as compared to the Low Dose of FSH plus NP3S vehicle control. With the FSH low dose alone, an average of one oocyte per rat was collected, and only 4 out of ten rats ovulated. In contrast, when the FSH low dose was in conjunction with Dipyridamole (1, 5 or 25 mg/kg) the average number of oocytes per rat was 7.5, 6.8 and 6.2, respectively, and 7 out of 10, 6 out of 10 or 10 out of 10 rats ovulated, respectively. These results are shown in FIG. 1.

Figure 2:
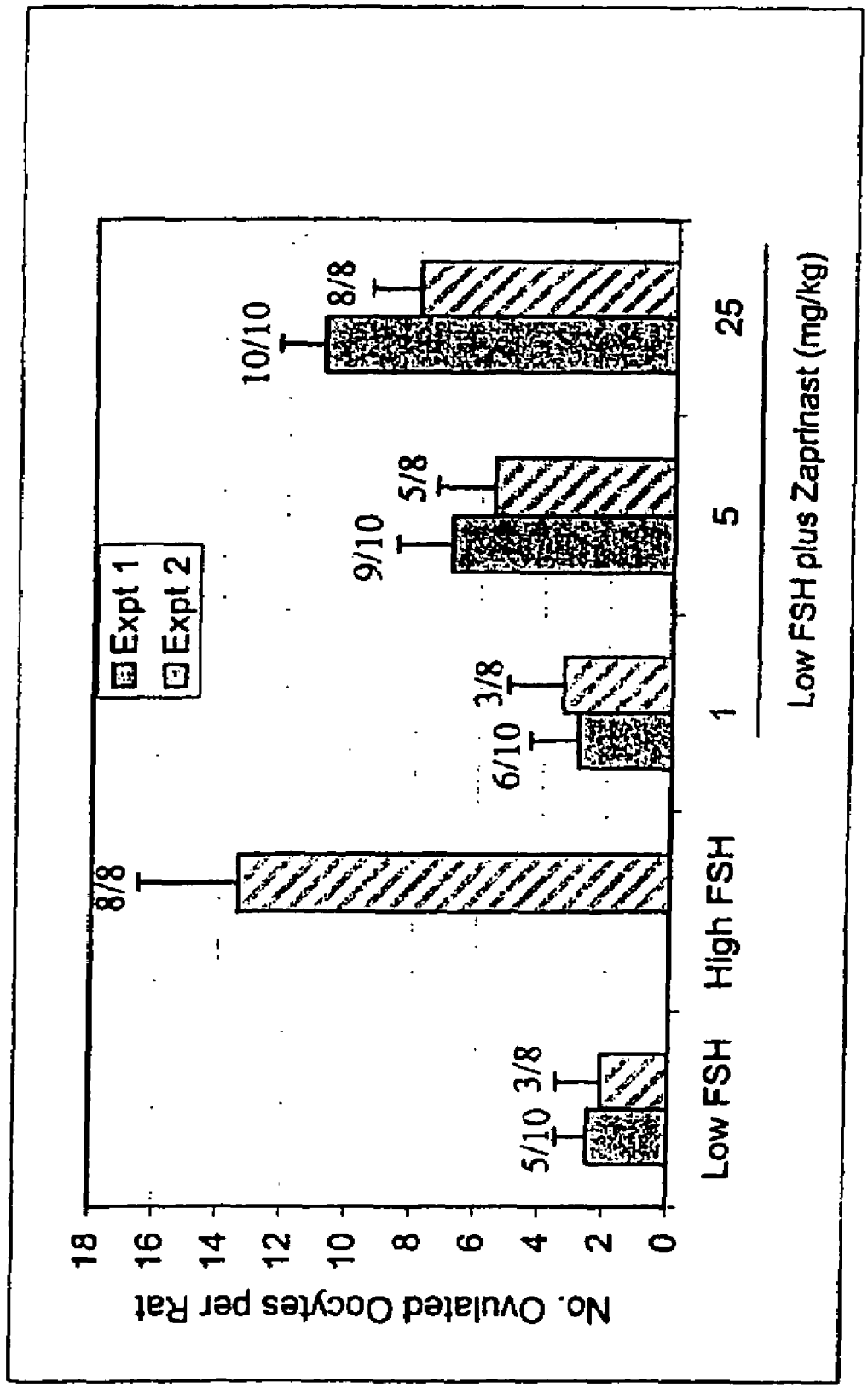
FIG. 2 shows the number of oocytes ovulated per rat in immature female rats treated with a suboptimal dose of FSH ("Low FSH"; 151.5 ng×4 per rat) and rats treated with the suboptimal dose of FSH ("Low FSH") plus Zaprinast (1, 5, 25 mg/kg×4 per rat).

Zaprinast (an inhibitor of PDE's 1, 5, 6, 7, 9, 10, 11) was administered at doses of 1, 5 and 25 mg/kg×4 injections per rat (subcutaneously) in NP3S with the Low Dose FSH, resulting in a dose-related increase in the number of ovulated oocytes per rat as compared to the Low Dose FSH plus NP3S vehicle control. With the FSH low dose alone, an average of 2.4 oocytes per rat was collected, and only 5 out of ten rats ovulated (Experiment 1). In contrast, when the FSH low dose was in conjunction with Zaprinast (1, 5 or 25 mg/kg) the average number of oocytes per rat was 3.25, 6.4, 9.5, respectively, and 6 out of 10, 9 out of 10 or 10 out of 10 rats ovulated (Experiment 1), respectively. These results are shown in FIG. 2.

Figure 3:
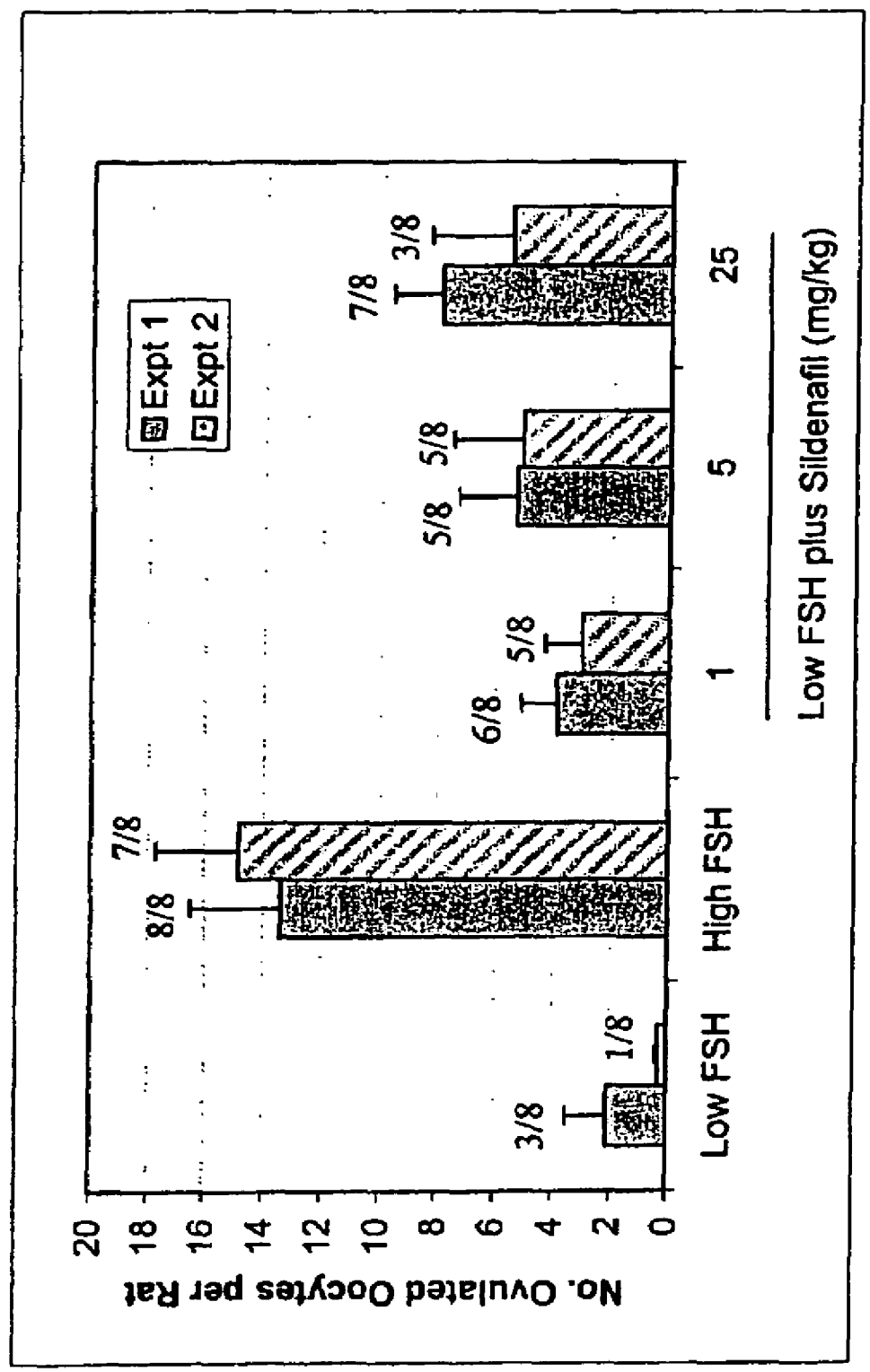
FIG. 3 shows the number of oocytes ovulated per rat in immature female rats treated with a suboptimal dose of FSH ("Low FSH"; 151.5 ng×4 per rat) and rats treated with the suboptimal dose of FSH ("Low FSH") plus Sildenafil (1, 5, 25 mg/kg×4 per rat).

Sildenafil (an inhibitor of PDE's 1, 5 and 6) was administered at doses of 1, 5 and 25 mg/kg×4 injections per rat (subcutaneously) in NP3S with the Low Dose FSH, resulting in a dose-related increase in the number of ovulated oocytes per rat as compared to the Low Dose FSH plus NP3S vehicle control. With the FSH low dose alone, an average of 1 oocyte per rat was collected, and only 3 out of ten rats ovulated (Experiment 1). In contrast, when the FSH low dose was in conjunction with Sildenafil (1, 5 or 25 mg/kg) the average number of oocytes per rat was 3.5, 5.5, 6.9, respectively, and 6 out of 8, 5 out of 8 or 7 out of 8 rats ovulated (Experiment 1), respectively. These results are shown in FIG. 3.

Figure 4:
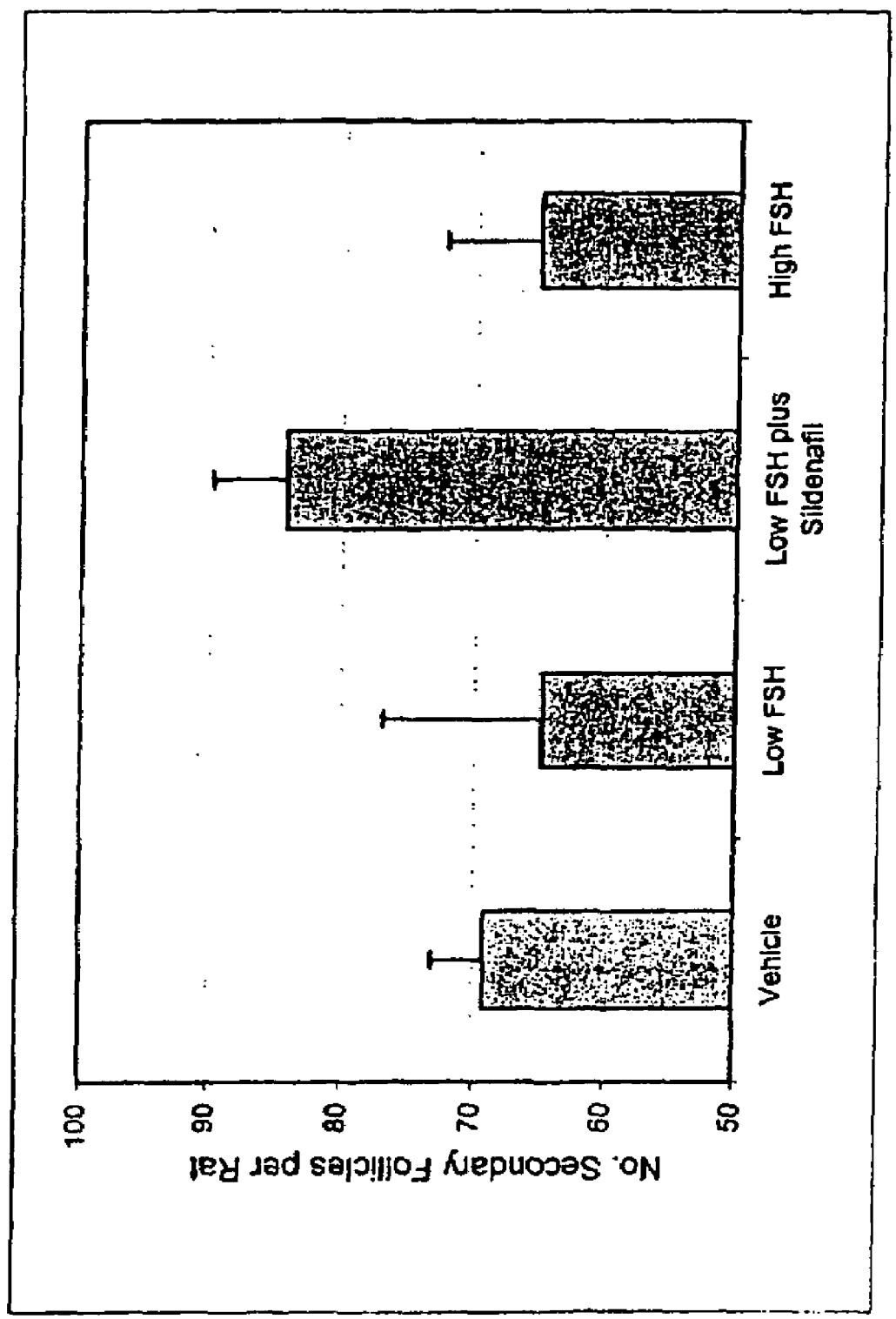
FIG. 4 shows the number of secondary follicles in rats treated with low dose FSH ("Low FSH"; 151.5 ng×3 per rat), high dose FSH ("High FSH"; 606.2 ng×3 per rat), and low dose FSH plus Sildenafil (25 mg/kg×3 per rat).

The total number of secondary follicles per rat (2 ovaries) in rats treated with vehicle, Low FSH, High FSH, or Low FSH+75 mg/kg Sildenafil is shown in FIG. 4. The total number of secondary follicles is higher in the Sildenafil+FSH group than in any of the other groups [Vehicle=69; Low FSH=64; Low FSH plus Sildenafil=84; High FSH=64].

Figure 5:
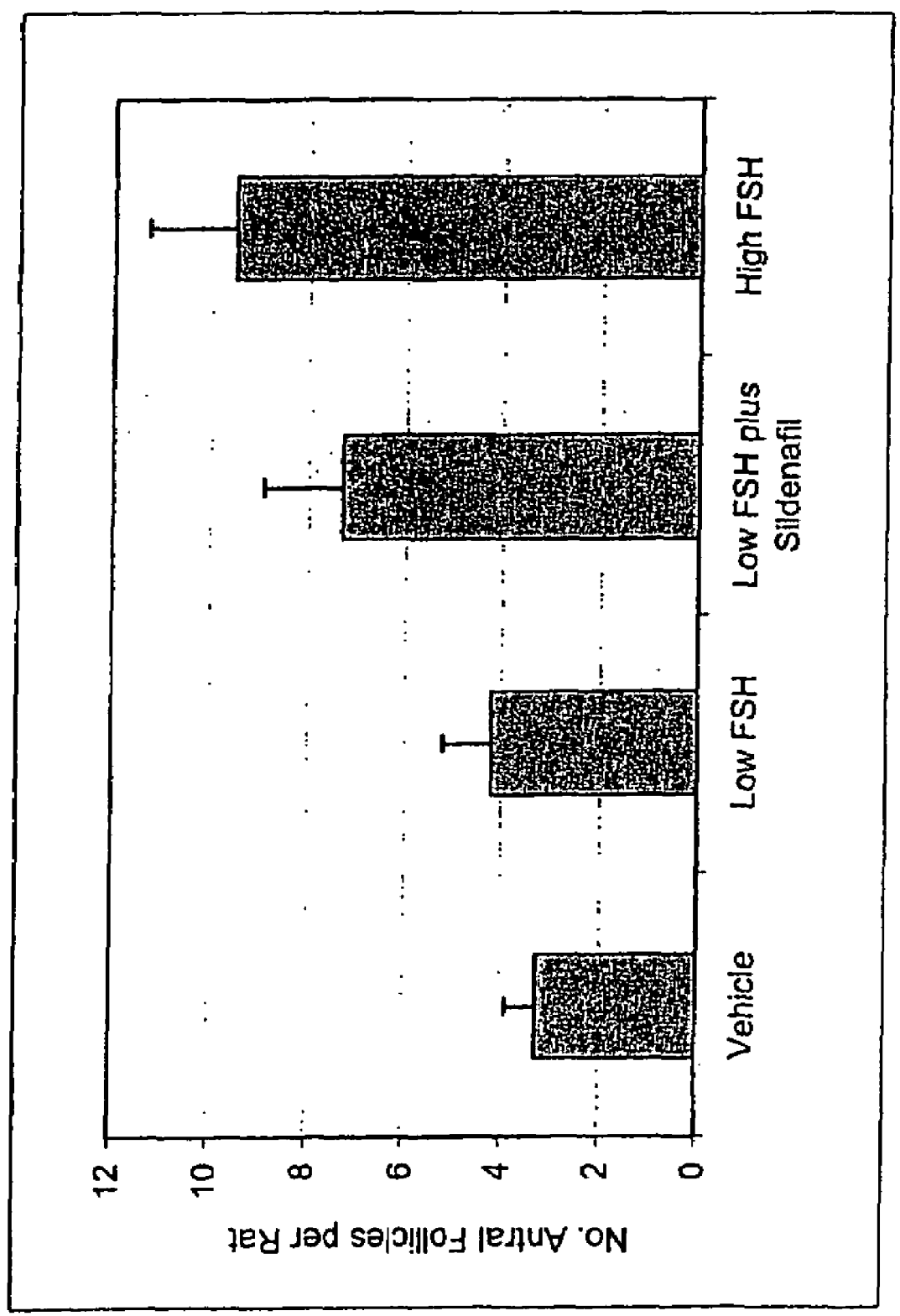
FIG. 5 shows the number of antral follicles in rats treated with low dose FSH ("Low FSH"; 151.5 ng×3 per rat), high dose FSH ("High FSH"; 606.2 ng×3 per rat), and low dose FSH plus 75 mg/kg Sildenafil.

The total number of antral follicles per rat (2 ovaries) in rats treated with vehicle, Low FSH, High FSH, or Low FSH+75 mg/kg Sildenafil, is shown in FIG. 5. The total number of antral follicles in rats treated with Sildenafil+FSH is higher than the number of antral follicles in rats treated with Low FSH [Vehicle=3.2; Low FSH=4.1; Low FSH plus Sildenafil=7.4; high FSH=9.5].

Figure 6:
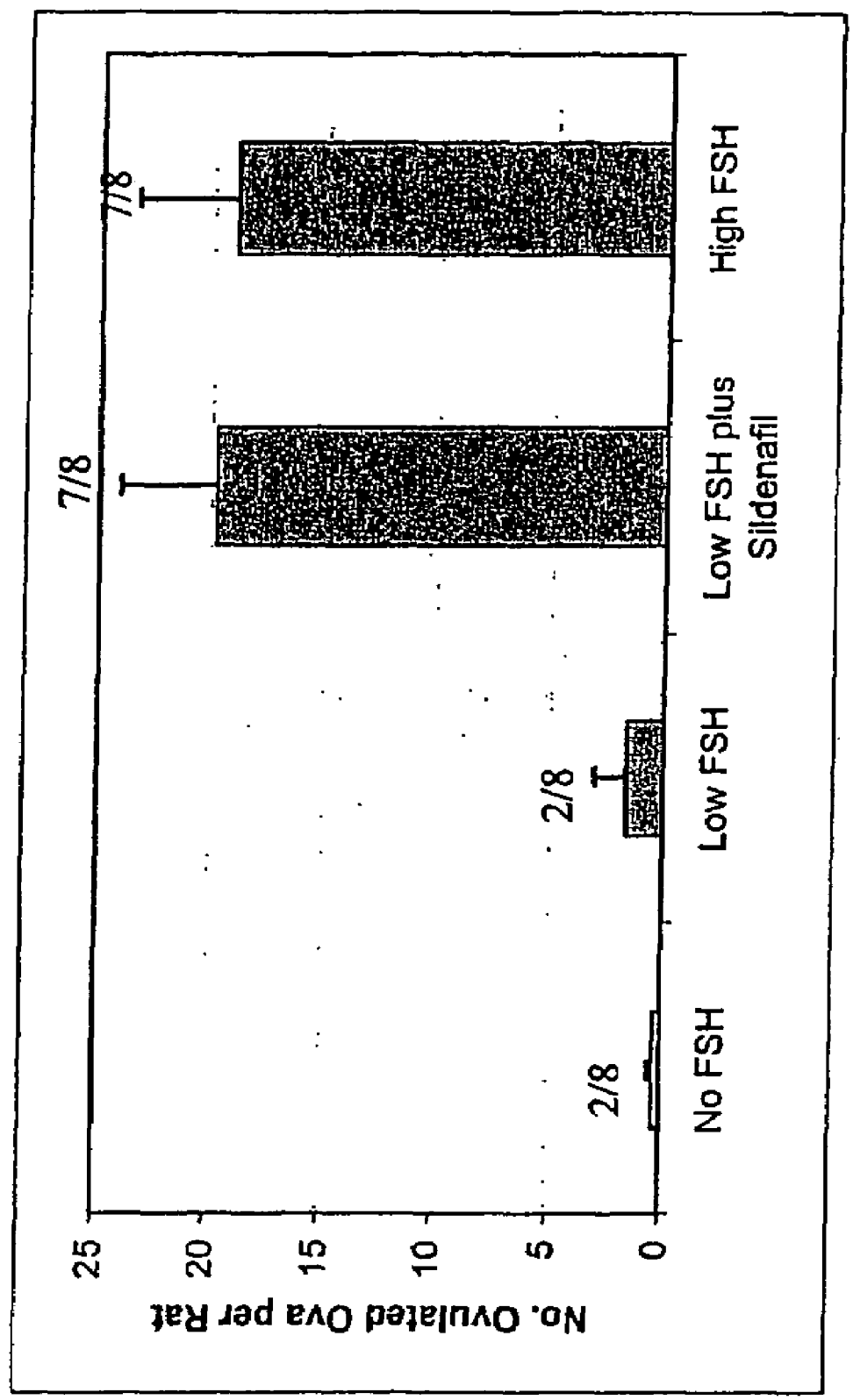
FIG. 6 shows the number of oocytes ovulated per rat in immature female rats treated with low dose FSH ("low FSH"; 151.5 ng×3 per rat), high dose FSH ("High FSH"; 606.2 ng×3 per rat), and low dose of FSH (151.5 ng×4 per rat) plus Sildenafil (1, 5, 25 mg/kg×4 per rat) administered in an aqueous buffer.

Sildenafil was administered at doses of 1, 5 and 25 mg/kg×4 injections per rat (subcutaneously) in aqueous vehicle with the Low Dose FSH, resulting in a dose-related increase in the number of ovulated oocytes per rat as compared to the Low Dose FSH alone plus aqueous vehicle control. With the FSH low dose alone, an average of 1 oocyte per rat was collected, and only 2 out of 8 rats ovulated. In contrast, when the FSH low dose was in conjunction with Sildenafil (5 mg/kg) the average number of oocytes per rat was 20, and 7 out of 8 rats ovulated. These results are shown in FIG. 6. [Note: FIG. 6 differs from FIG. 3 in that the vehicle is aqueous rather than organic NP3S-SM]

Figure 7:
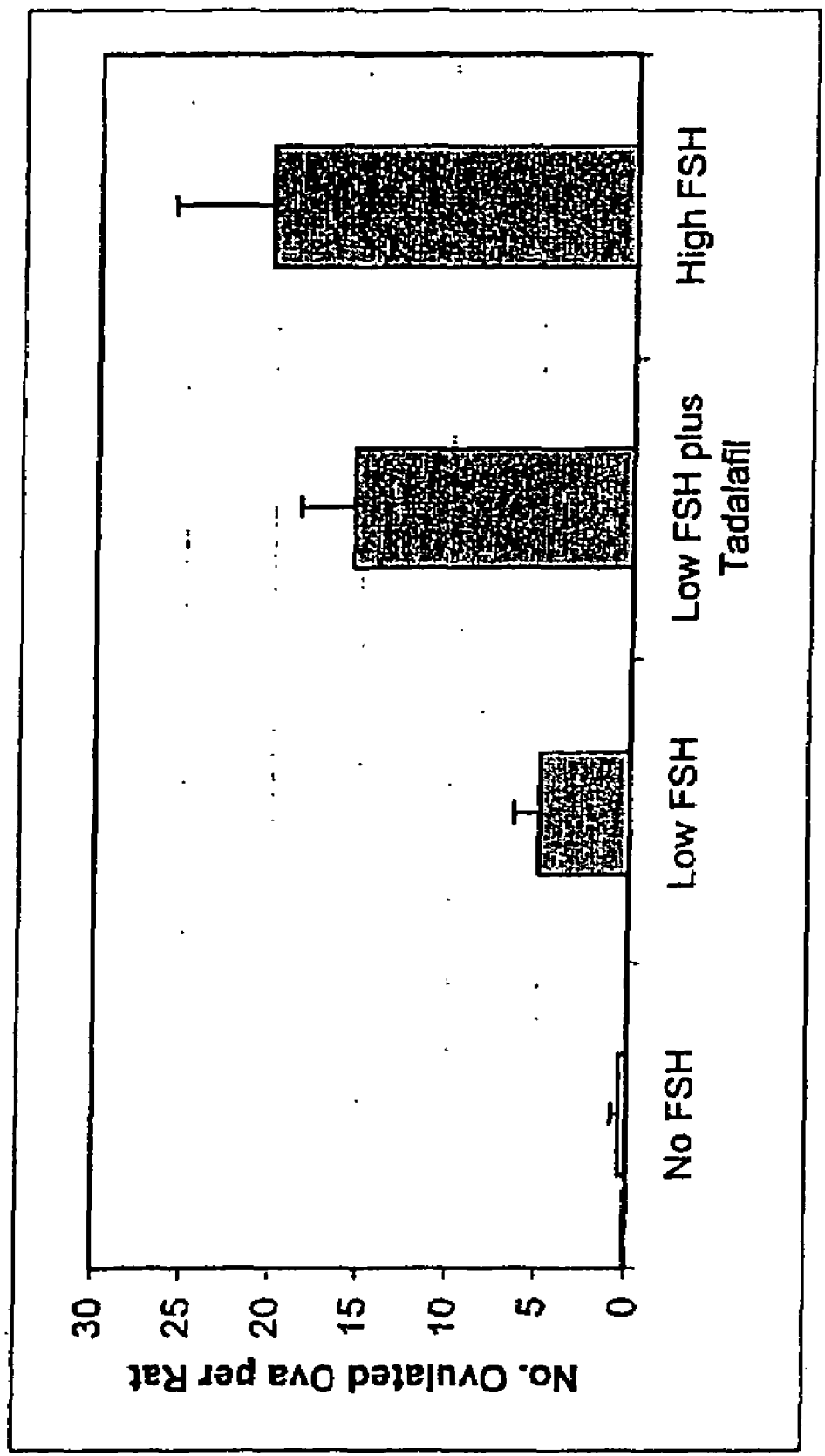
FIG. 7 shows the number of oocytes ovulated per rat in immature female rats treated with no FSH ("no FSH"), a suboptimal dose of FSH ("low FSH": 151.5 ng×3 per rat), the suboptimal dose of FSH ("low FSH": 151.5 ng×4 per rat) plus Tadalafil (25 mg/kg×4 per rat), and a high dose of FSH ("high FSH": 606.2 ng×3 per rat), administered in an aqueous buffer.

Tadalafil (an inhibitor of PDE's 5 and 6) was administered at a dose of 25 mg/kg×4 injections per rat (subcutaneously) in water with the Low Dose FSH, resulting in a dose-related increase in the number of ovulated oocytes per rat as compared to the Low Dose FSH plus NP3S vehicle control. When no FSH was used, less than one oocyte per rat was collected. These results are shown in FIG. 7. When no FSH was administered an average of one oocyte per rat was collected. With the suboptimal dose of FSH ("low FSH": 151.5 ng×4 per rat) an average of 5 oocytes per rat were collected. When the suboptimal dose was combined with Tadalafil (25 mg/kg×4 per rat; "low FSH plus Tadalafil") an average of 16 oocytes were collected per rat. With a high dose of FSH ("high FSH": 606.2 ng×3 per rat) an average of 21 oocytes per rat were collected.

Compound no. 31 from Ahn, et al., *J. Med. Chem.*, 40:2196–2210 (1997) ((6aR,9aS)-2-(Biphenylylmethyl)-5, 6a,7,8,9,9a-hexahydro-5-methyl-3(phenylmethyl)cyclopent [4,5]imidazo-[2,1-b]purin-4(3H)-one) (an inhibitor of PDE 1) is shown below:

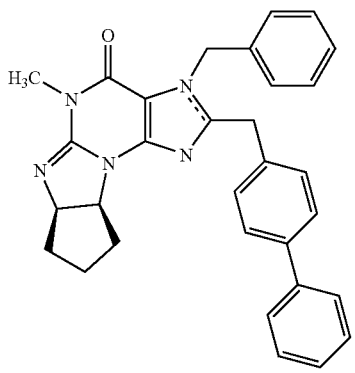

Figure 8:
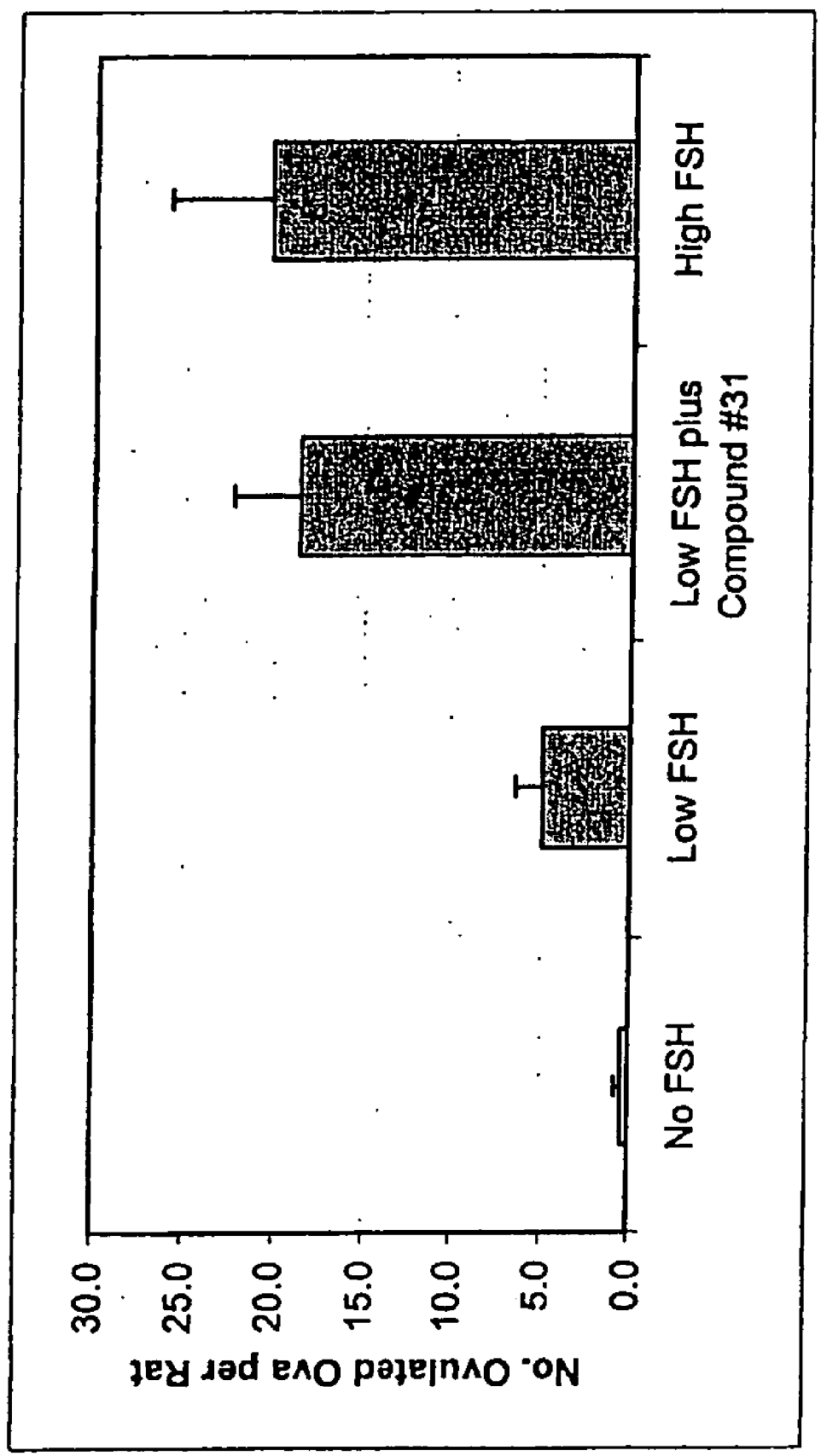
FIG. 8 shows the number of oocytes ovulated per rat in immature female rats treated with no FSH ("no FSH"), a suboptimal dose of FSH ("low FSH": 151.5 ng×3 per rat), the suboptimal dose of FSH ("low FSH": 151.5 ng×4 per rat) plus Compound no. 31 ((6aR,9aS')-2-(Biphenylylmethyl)-5,6a,7,8,9,9a-hexahydro-5-methyl-3(phenylmethyl)cyclopent[4,5]imidazo-[2,1-b]purin-4(3H)-one) (25 mg/kg×4 per rat), and High FSH (606.2 ng×3 per rat), administered in an aqueous buffer.

Compound no. 31 was administered at a dose of 25 mg/kg×4 injections per rat (subcutaneously) in NP3S with the Low Dose FSH, resulting in a dose-related increase in the number of ovulated oocytes per rat as compared to the Low Dose FSH plus NP3S vehicle control. These results are shown in FIG. 8. When no FSH was administered an average of one oocyte per rat was collected. When a suboptimal dose of FSH was administered ("low FSH": 151.5 ng×4 per rat) an average of 5 oocytes per rat were collected. When the suboptimal dose of FSH was combined with compound no. 31 (25 mg/kg×4 per rat), an average of 18 oocytes per rat were collected. With high dose FSH ("high FSH": 606.2 ng×3 per rat), an average of 21 oocytes per rat were collected.

Compound no. 33 (5'-Methyl-2'(biphenylylmethyl)-3'-(phenylmethyl)spiro[cyclopentane-1,7'(8'h)-[3H]imidazo[2,1-b]purin]-4(5'h)-one) (an inhibitor of PDE 1) from Ahn, et al., *J. Med. Chem.*, 40:2196–2210 (1997) is shown below:

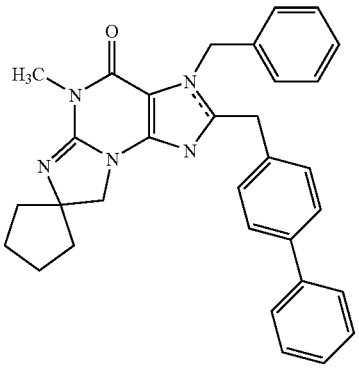

Figure 9:
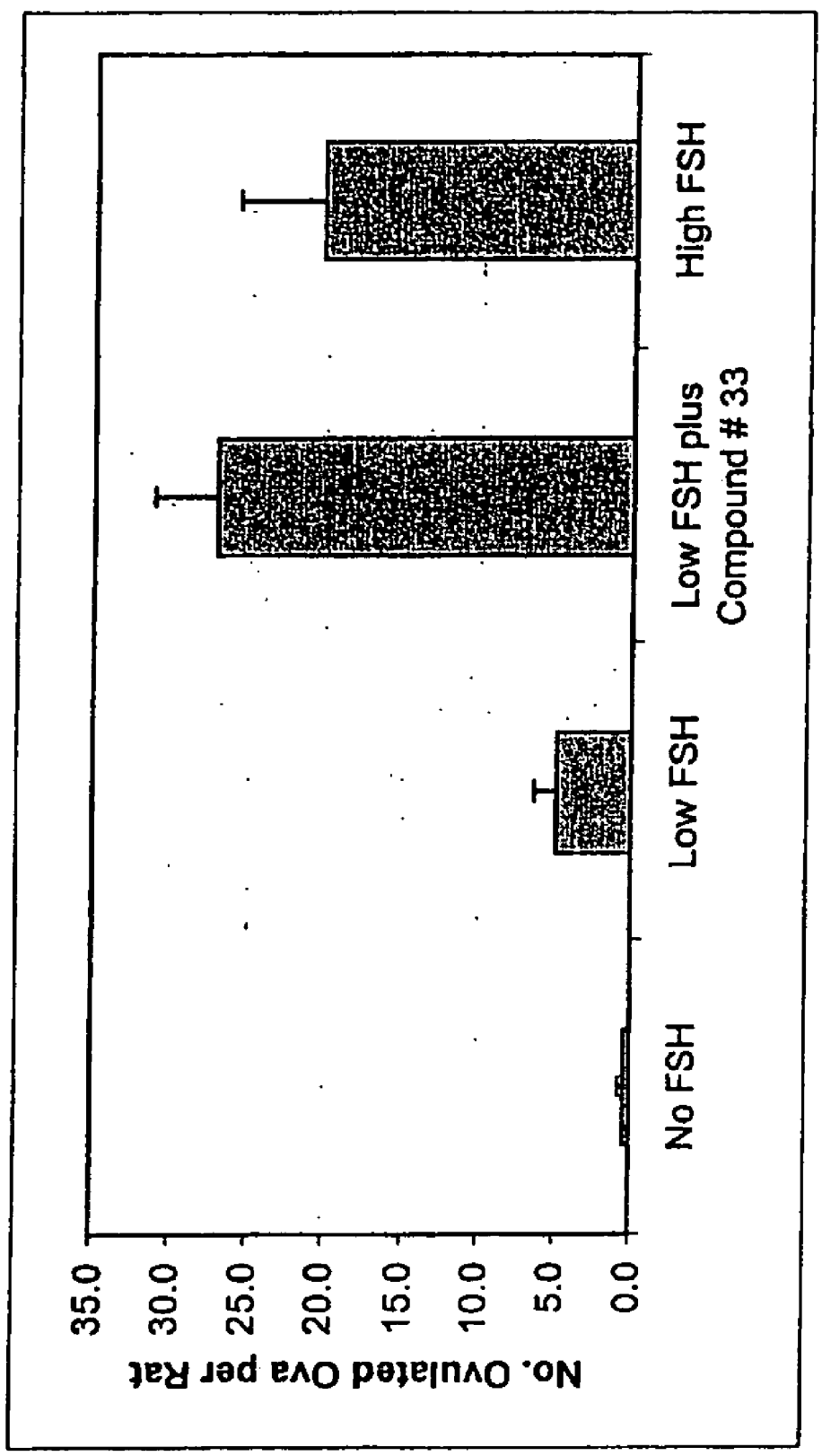
FIG. 9 shows the number of oocytes ovulated per rat in immature female rats treated with no FSH ("no FSH"), a suboptimal dose of FSH ("low FSH": 151.5 ng×3 per rat), the suboptimal dose of FSH ("low FSH": 151.5 ng×4 per rat) plus Compound no. 33 (5'-Methyl-2'(biphenylylmethyl)-3'-(phenylmethyl)spiro[cyclopentane-1,7'(8'H)-[3H]imidazo [2,1-b]purin]-4(5'H)-one) (25 mg/kg×4 per rat), and High FSH (606.2 ng×3 per rat), administered in an aqueous buffer.

Compound no. 33 was administered at a dose of 25 mg/kg×4 injections per rat (subcutaneously) in NP3S with the Low Dose FSH, resulting in a dose-related increase in the number of ovulated oocytes per rat as compared to the Low Dose FSH plus NP3S vehicle control. These results are shown in FIG. 9. When no FSH was administered an average of 1 oocyte per rat was collected. When a suboptimal dose of FSH was administered ("low FSH": 151.5 ng×4 per rat) an average of 5 oocytes per rat were collected. When the suboptimal dose of FSH was combined with compound no. 33 (25 mg/kg×4 per rat) an average of 27 oocytes per rat were collected. With high dose FSH ("high FSH": 606.2 ng×3 per rat) an average of 20 oocytes per rate were collected.

Figure 15:
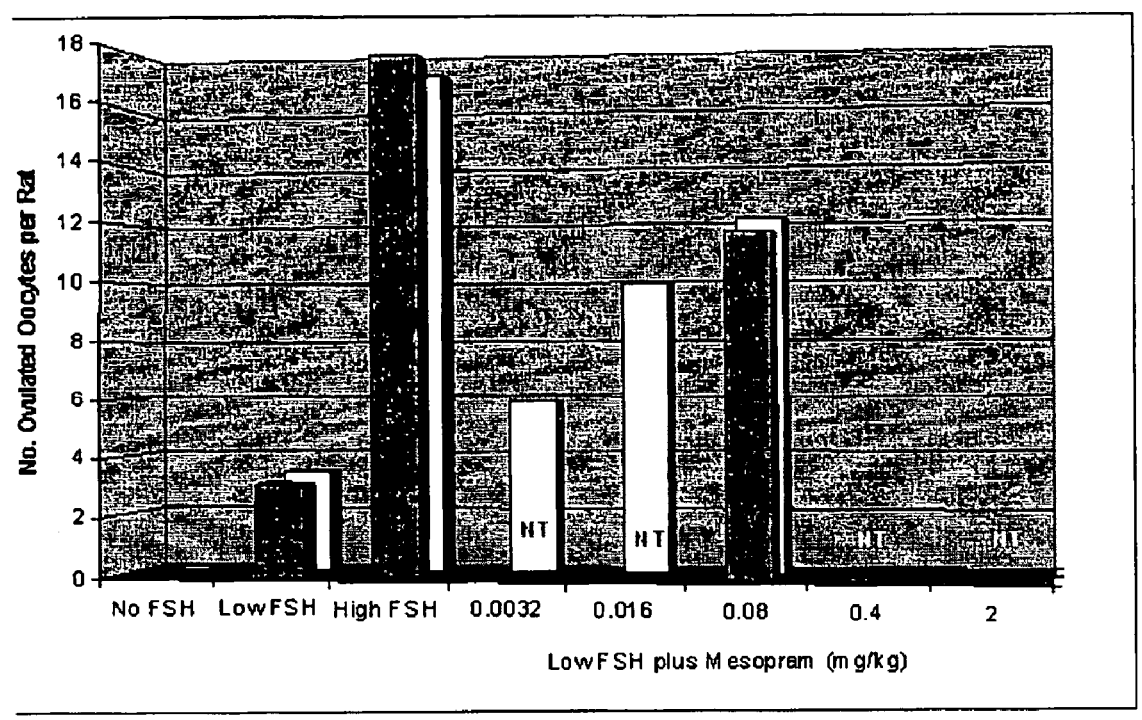
FIG. 15 In vivo demonstration of induction of follicle maturation. Cumulative data demonstrating increased oocyte production upon stimulation using a combination of a low dose of FSH with varying concentrations (0.0032, 0.016, 0.08 mg/kg; 0.4 mg/kg; 2 mg/kg) of Mesopram. Results from two independent studies are shown.

Mesopram was administered at 0.08, 0.4, and 2 mg/kg/day together with a low dose of FSH. A significant enhancement of follicular maturation was seen over the group receiving low FSH alone. At higher doses, there appeared to be a decrease in follicular maturation. Mesopram was then administered at lower doses: 0.032, 0.016, 0.08 mg/kg together with a low dose of FSH, which demonstrated a dose dependent increase in follicular maturation, reaching significance at 0.08 mg/kg. These results are shown in 1625 FIG. 15.

Other PDE inhibitors were tested in the above model, and the results are listed in Table 1.

TABLE 1

Follicular growth activity of various PDE inhibitors

| Compound | PDE selectivity | Follicular growth activity with Low FSH? |
| --- | --- | --- |
| Papavarine | Non-selective | NO |
| Sildenafil | PDE1, 5, 6 | YES |
| ARIFLO (Cilomilast) | PDE4 | Inhibits follicular growth |
| Dipyridamole | PDE5, 6, 7, 8, 10, 11 | YES |
| Zaprinast | PDE1, 5, 6, 7, 9, 10, 11 | YES |
| CDP840 | PDE4 | Inhibits follicular growth |
| Tadalafil | PDE5 and 6 | YES |
| Compound no. 31 | PDE1 | YES |
| Compound no. 33 | PDE1 | YES |

Example 2

Induction of cAMP Using Various PDE Inhibitors in Combination with Low-dose FSH

In addition to the evaluation of rat granulosa cells, produced as described above, in order to measure cAMP in cell lines, JC-410 porcine granulosa cells were used. These cells were obtained from Dr. Jorge Chedrese (University of Saskatchewan). The cells were maintained in DMEM/F12 supplemented with 5% newborn calf serum (Gibco) and 5 μg/ml of insulin (Gibco). Stable cell lines were established by transfecting the cDNAs 1635 for the human LH and FSH receptors into the cells using standard transfection techniques and selection with 300 μg/ml of Geneticin (Gibco). Following selection, the cells were maintained in the same concentration of Geneticin. For cAMP determinations, the cells were plated at a density of 25,000 cells per well, in 96 well plates, one day prior to the assay. The following day, the cells were stimulated for 1 hour with increasing doses of the inhibitor molecules in the presence, or absence, of 1 nM FSH, as indicated. All compounds were diluted in assay buffer (DMEM/F12, 0.1% BSA—Sigma) containing 4% DMSO (0.5% final concentration in the assay). After a 1 hour stimulation, the cells were lysed and cAMP was assayed using the Tropix cAMP-Screen assay (Applied Biosystems), according to the manufacturers protocol.

Measurements of cAMP in primary ovarian dispersate cultures were monitored as follows. Ovaries were harvested from Sprague-Dawley rats (22 days old) and decapsulated under a dissecting microscope in 3–5 ml of digestion media. The digestion media consisted of assay media (McCoy's 5A media supplemented with 1 mg/ml BSA (Sigma), 5 μg/ml of gentamycin and 3 μg/ml of amphotericin B (Gibco)), containing 8 mg/ml of collagenase (Sigma) and 0.05% DNase (Invitrogen). After decapsulating, the ovaries were dissected into small pieces using 27 gauge needles, transferred to a 15 ml tube and digested for 45 min at 37° C., while shaking.

The digested tissue was filtered through a 70 μm Nalgene Filter and the filtrate was centrifuged at 1000 rpm for 5 min. The pellet was washed with assay media and centrifuged a second time. The resulting pellet was suspended in 2 ml of growth media (McCoy's 5A media supplemented with 5% FBS, 5 μg/ml gentamycin, 3 μg/ml amphotericin B (Gibco)) and the cells were counted. The cells were diluted in growth media, plated at 25–30,000 cells/well and cultured for 48 hours prior to stimulation. The cells were stimulated and cAMP was assayed as described above for the cell line measurements.

Results

Figure 10A:
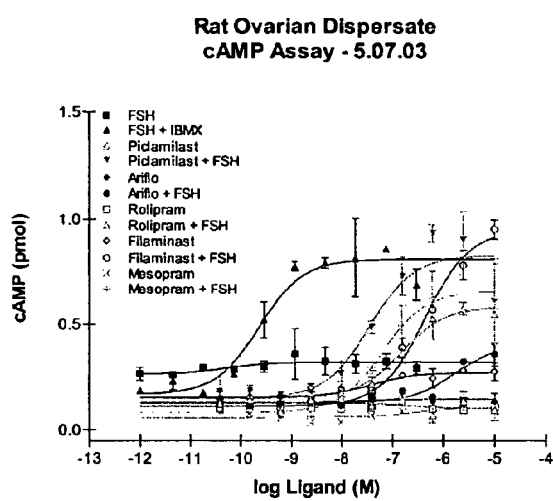
FIGS. 10A–10C. In vitro studies to determine the ability of PDE 4 inhibitors to induce or increase cAMP in rat granulosa cells (rat ovarian dispersate, 10A) and/or human FSH receptor-expressing porcine granulosa cells (JC410/FSHR, 10B, 10C).
Figure 10B:
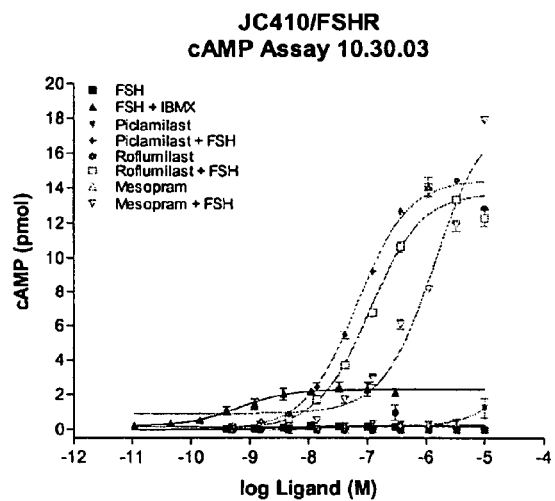
Figure 10C:
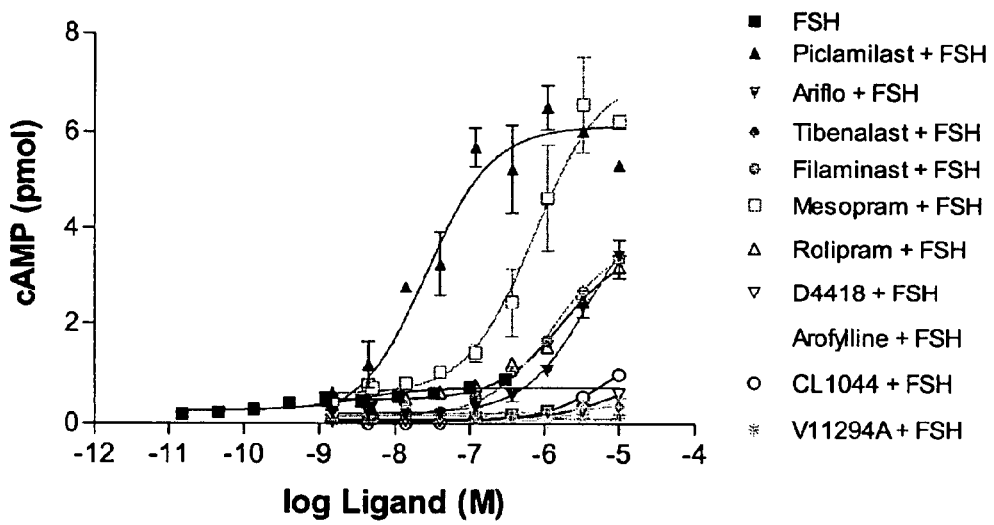

A panel of PDE 4 inhibitors were tested for their ability to induce cAMP in FSH treated, or untreated, rat granulosa cells and/or human FSH receptor-expressing porcine granulosa cell line JC410 (JC41 OFSHR) in vitro. Of the PDE 4 inhibitors, some were highly active in inducing cAMP, some were of intermediate activity and some had little or no activity in this model. Notably, in the absence of FSH, the PDE 4 inhibitors had little or no capacity to induce cAMP (see FIGS. 10A–10C). The potency of the inhibitors was the same regardless of the source of the granulosa cells, i.e., it was relatively similar in both the cell line and the primary granulosa cells.

In vivo, two exemplary PDE 4 inhibitors, Piclamilast and Roflumilast, increased FSH-induced follicle maturation. Low concentrations of Piclamilast (0.08 and 0.4 mg/kg) were not sufficient to induce follicle maturation in the absence of a low level of exogenous FSH (FIG. 13). However, at the higher concentration of 2 mg/kg Piclamilast did induce follicle maturation (see FIG. 13). When Piclamilast is administered in the presence of low doses of FSH there was a very marked induction in follicle maturation as evidenced by the increase in number of ovulatable oocytes (FIG. 14).

The above results show that PDE 4 inhibitors can, when administered to mammals along with suboptimal doses of FSH, lead to an increase in the number of hCG-ovulatable oocytes. Methods and compositions for exploiting this finding have been described herein above.

All of the compositions and/or methods disclosed and claimed herein can be made and executed without undue experimentation in light of the present disclosure. While the compositions and methods of this invention have been described in terms of preferred embodiments, it will be apparent to those of skill in the art that variations may be applied to the compositions and/or methods and in the steps or in the sequence of steps of the method described herein without departing from the concept, spirit and scope of the invention. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of the invention as defined by the appended claims.

The references, patents and patent publications cited herein throughout, to the extent that they provide exemplary procedural or other details supplementary to those set forth herein, are all specifically incorporated herein by reference.

What is claimed is:

1. A method for stimulating ovarian follicular growth in a female, comprising administering to a female a medicament comprising a phosphodiesterase (PDE) inhibitor, whereby ovarian follicular growth is stimulated in said female.

2. A method according to claim 1, wherein the female is undergoing ovulation induction.

3. A method according to claim 1 or 2, wherein the female is undergoing controlled ovarian hyperstimulation.

4. A method according to claim 1 or 2, wherein the medicament is administered simultaneously, separately or sequentially with follicle stimulating hormone (FSH), or an agent having FSH activity, or an agent that stimulates endogenous FSH release.

5. A method according to claim 3, wherein the medicament is administered simultaneously, separately or sequentially with FSH, or an agent having FSH activity, or an agent that stimulates endogenous FSH release.

6. A method according to claim 4, wherein the medicament is administered with FSH, and wherein the dose of FSH is less than the dose required in the same patient in the absence of the PDE inhibitor, in order to achieve the same result in terms of follicular growth.

7. A method according to claim 5, wherein the medicament is administered with FSH, and wherein the dose of FSH is less than the dose required in the same patient in the absence of the PDE inhibitor, in order to achieve the same result in terms of follicular growth.

8. A method according to claim 1 or 2, wherein the medicament is administered starting at or about day 2 to 3 after menses.

9. A method according to claim 3, wherein the medicament is administered starting at or about day 2 to 3 after menses.

10. A method according to claim 1 or 2, wherein the medicament is administered daily followed by an ovulation-triggering dose of human chorionic gonadotropin (hCG).

11. A method according to claim 3, wherein the medicament is administered daily followed by an ovulation-triggering dose of hCG.

12. A method according to claim 10, wherein the ovulation-triggering dose of hCG is 5,000–10,000 IU.

13. A method according to claim 11, wherein the ovulation-triggering dose of hCG is 5,000–10,000 IU.

14. A method according to claim 1 or 2, wherein the PDE inhibitor is an inhibitor of at least one PDE type selected from the group consisting of 1, 5 and 6.

15. A method according to claim 3, wherein the PDE inhibitor is an inhibitor of at least one PDE type selected from the group consisting of 1, 5 and 6.

16. A method according to claim 1 or 2, wherein the PDE inhibitor is selected from: 5-[2-ethoxy-5-(4-methyl-1-piperazinylsulphonyl)phenyl]-1-methyl-3-n-propyl-1,6-dihydro-7H-pyrazolo[4,3-d]pyrimidin-7-one (sildenafil); Zaprinast; dipyridamole; 5-(2-ethoxy-5-morpholinoacetylphenyl)-1-methyl-3-n-propyl-1,6-dihydro-7H-20pyrazolo[4,3-d]pyrimidin-7-one; 3-ethyl-5-[5-(4-ethylpiperazin-1-ylsulphonyl)-2-n-propoxyphenyl]-2-(pyridin-2-yl)methyl-2,6-dihydro-7H-pyrazolo[4,3-d]pyrimidin-7-one; 3-ethyl-5-[5-(4-ethylpiperazin-1-ylsulphonyl)-2-(2-methoxyethoxy) pyridin-3-yl]-2-(pyridin-2-yl)methyl-2,6-dihydro-7H-pyrazolo[4,3-d]pyrimidin-7-one; (+)-3-ethyl-5-[5-(4-ethylpiperazin-1-ylsulphonyl)-2-(2-methoxy-1(R)-methylethoxy)pyridin-3-yl]-2-methyl-2,6-dihydro-7H-pyrazolo[4,3-d]pyrimidin-7-one; 5-[2-ethoxy-5-(4-ethylpiperazin-1-ylsulphonyl)pyridin-3-yl]-3-ethyl-2-[2-methoxyethyl]-2,6-dihydro-7H-pyrazolo[4,3-d]pyrimidin-7-one; 5-[2-iso-butoxy-5-(4-ethylpiperazin-1-ylsulphonyl) pyridin-3-yl]-3-ethyl-2-(1-methylpiperidin-4-yl)-2,6-dihydro-7H-pyrazolo[4,3-d]pyrimidin-7-one; 5-[2-ethoxy-5-(4-ethylpiperazin-1-ylsulphonyl)pyridin-3-yl]-3-ethyl-2-phenyl-2,6-dihydro-7H-pyrazolo[4,3-d]pyrimidin-7-one; 5-(5-acetyl-2-propoxy-3-pyridinyl)-3-ethyl-2-(1-isopropyl-3-azetidinyl)-2,6-dihydro-7H-pyrazolo[4,3-d]pyrimidin-7-one; 5-(5-acetyl-2-butoxy-3-pyridinyl)-3-ethyl-2-(1-ethyl- 3-azetidinyl)-2,6-dihydro-7H-pyrazolo[4,3-d]pyrimidin-7-one; (6R,12aR)-2,3,6,7,12,12a-hexahydro-2-methyl-6-(-3,4-methylenedioxyphenyl)pyrazino[2',1':6,1]pyrido[3,4-b]indole-1,4-dione (Tadalafil; IC-351); 2-[2-ethoxy-5-(4-ethyl-piperazin-1-yl-1-sulphonyl)-phenyl]-5-methyl-7-propyl-3H-imidazo[5,1-f][1,2,4]triazin-4-one (vardenafil); 4-bromo-5-(pyridylmethylamino)-6-[3-(4-chlorophenyl)-propoxy]-3(2H)pyridazinone; 1-[4-[(1,3-benzodioxol-5-yl-methyl)amiono]-6-chloro-2-quinozolinyl]-4-piperidine-carboxylic acid, monosodium salt; (+)-cis-5,6a,7,9,9,9a-hexahydro-2-[4-(trifluoromethyl)-phenylmethyl-5-methyl-cyclopent-[4,5]imidazo[2,1-b]purin-4(3H)one; furaziocillin; cis-2-hexyl-5-methyl-3,4,5,6a,7,8,9,9a-octahydrocyclopent[4,5]-imidazo[2-,1-b]purin-4-one; 3-acetyl-1-(2-chlorobenzyl)-2-propylindole-6-carboxylate; 3-acetyl-1-(2-chlorobenzyl)-2-propylindole-6-carboxylate; 4-bromo-5-(3-pyridylmethylamino)-6-(3-(4-chlorophenyl)propoxy)-3-(2H)pyridazinone; 1-methyl-5(5-morpholinoacetyl-2-n-propoxyphenyl)-3-n-propyl-1,6-dihydro-7H-pyrazolo(4,3-d)pyrimidin-7-one; 1-[4-[(1,3-benzodioxol-5-ylmethyl)amino]-6-chloro-2-quinazolinyl]-4-piperidinecarboxylic acid, monosodium salt; Pharmaprojects No. 4516; Pharmaprojects No. 5051; Pharmaprojects No. 5064; Pharmaprojects No. 5069; GF-196960; E-8010 and E-4010; Bay-38-3045 & Bay-38-9456; Vinpocetine; SCH-5 1866; SCH-59498; (6aR,9aS)-2-(Biphenylylmethyl)-5,6a,7,8,9,9a-hexahydro-5-methyl-3(phenylmethyl)cyclopent[4,5]imidazo-[2,1-b]purin-4(3H)-one; 5'-Methyl-2'(biphenylylmethyl)-3'-(phenylmethyl) spiro[cyclopentane-1,7'(8'H)-[3H]imidazo[2,1-b]purin]-4(5'H)-one; (6aR,9aS)-5,6a,7,8,9,9a-Hexahydro-5-methyl-2-(phenylethynyl)-3-(phenylmethyl)cyclopent[4,5]imidazo[2,1-b]-purin-4(3H)-one; dipyridamole, AWD-12-171 and AWD-12-217; BMS-341400; UK-343,664; 5E-3623, 5E-3569, 5E-3657, E4021; KS-505a; YC-1; IDDB reference number 323951; WIN-61691; FR226807; IDDB references 461317, 462503, 461321, 461324, 466146; pyridine-4-ylmethyl 3-(1,3-benzodioxol-5-yl)-9-oxo-1,3,4,9 tetrahydro-2H-pyrrolo[3,4-b]quinoline-2-carboxylate:

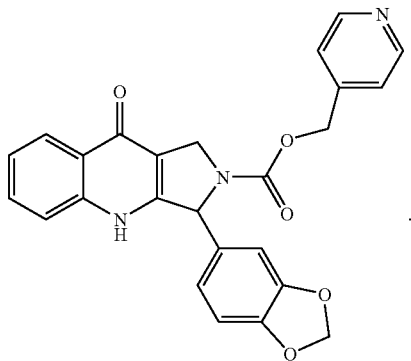

17. A method according to claim 3, wherein the PDE inhibitor is selected from: 5-[2-ethoxy-5-(4-methyl-1-piperazinylsulphonyl)phenyl]-1-methyl-3-n-propyl-1,6-dihydro-7H-pyrazolo[4,3-d]pyrimidin-7-one (sildenafil); Zaprinast; dipyridamole; 5-(2-ethoxy-5-morpholinoacetylphenyl)-1-methyl-3-n-propyl-1,6-dihydro-7H-20pyrazolo[4,3-d]pyrimidin-7-one; 3-ethyl-5-[5-(4-ethylpiperazin-1-ylsulphonyl)-2-n-propoxyphenyl]-2-(pyr-idin-2-yl)methyl-2,6-dihydro-7H-pyrazolo[4,3-d]pyrimidin-7-one; 3-ethyl-5-[5-(4-ethylpiperazin-1-ylsulphonyl)-2-(2-methoxyethoxy)pyridi-n-3-yl]-2-(pyridin-2-yl)methyl-2,6-dihydro-7H-pyrazolo[4,3-d]pyrimidin-7-one; (+)-3-ethyl-5-[5-(4-ethylpiperazin-1-ylsulphonyl)-2-(2-methoxy-1(R)-methylethoxy)pyridin-3-yl]-2-methyl-2,6-dihydro-7H-pyrazolo[4,3-d]pyrimidin-7-one; 5-[2-ethoxy-5-(4-ethylpiperazin-1-ylsulphonyl)pyridin-3-yl]-3-ethyl-2-[2-methoxyethyl]-2,6-dihydro-7H-pyrazolo[4,3-d]pyrimidin-7-one; 5-[2-iso-butoxy-5-(4-ethylpiperazin-1-ylsulphonyl)pyridin-3-yl]-3-ethyl-2-(1-methylpiperidin-4-yl)-2,6-dihydro-7H-pyrazolo[4,3-d]pyrimidin-7-one; 5-[2-ethoxy-5-(4-ethylpiperazin-1-ylsulphonyl)pyridin-3-yl]-3-ethyl-2-phenyl-2,6-dihydro-7H-pyrazolo[4,3-d]pyrimidin-7-one; 5-(5-acetyl-2-propoxy-3-pyridinyl)-3-ethyl-2-(1-isopropyl-3-azetidinyl)-2,6-dihydro-7H-pyrazolo[4,3-d]pyrimidin-7-one; 5-(5-acetyl-2-butoxy-3-pyridinyl)-3-ethyl-2-(1-ethyl-3-azetidinyl)-2,6-dihydro-7H-pyrazolo[4,3-d]pyrimidin-7-one; (6R,12aR)-2,3,6,7,12,12a-hexahydro-2-methyl-6-(-3,4-methylenedioxyphenyl)pyrazino[2',1':6,1]pyrido[3,4-b]indole-1,4-dione (Tadalafil; IC-351); 2-[2-ethoxy-5-(4-ethyl-piperazin-1-yl-1-sulphonyl)-phenyl]-5-methyl-7-propyl-3H-imidazo[5,1-f][1,2,4]triazin-4-one (vardenafil); 4-bromo-5-(pyridylmethylamino)-6-[3-(4-chlorophenyl)-propoxy]-3(2H)pyridazinone; 1-[4-[(1,3-benzodioxol-5-yl-methyl)amiono]-6-chloro-2-quinozolinyl]-4-piperidine-carboxylic acid, monosodium salt; (+)-cis-5,6a,7,9,9,9a-hexahydro-2-[4-(trifluoromethyl)-phenylmethyl-5-methyl-cyclopent-[4,5]imidazo[2,1-b]purin-4(3H)one; furaziocillin; cis-2-hexyl-5-methyl-3,4,5,6a,7,8,9,9a-octahydrocyclopent[4,5]-imidazo[2-,1-b]purin-4-one; 3-acetyl-1-(2-chlorobenzyl)-2-propylindole-6-carboxylate; 3-acetyl-1-(2-chlorobenzyl)-2-propylindole-6-carboxylate; 4-bromo-5-(3-pyridylmethylamino)-6-(3-(4-chlorophenyl)propoxy)-3-(2H)pyridazinone; 1-methyl-5(5-morpholinoacetyl-2-n-propoxyphenyl)-3-n-propyl-1,6-dihydro-7H-pyrazolo(4,3-d)pyrimidin-7-one; 1-[4-[(1,3-benzodioxol-5-yl methyl)amino]-6-chloro-2-quinazolinyl]-4-piperidinecarboxylic acid, monosodium salt; Pharmaprojects No. 4516; Pharmaprojects No. 5051; Pharmaprojects No. 5064; Pharmaprojects No. 5069; GF-196960; E-8010 and E-4010; Bay-38-3045 & Bay-38-9456; Vinpocetine; SCH-5 1866; SCH-59498; (6aR,9aS)-2-(Biphenylylmethyl)-5,6a,7,8,9,9a-hexahydro-5-methyl-3(phenylmethyl)cyclopent[4,5]imidazo-[2,1-b]purin-4(3H)-one; 5'-Methyl-2'(biphenylylmethyl)-3'-(phenylmethyl) spiro[cyclopentane-1,7'(8'H)-[3H]imidazo[2,1-b]purin]-4(5'H)-one; (6aR,9aS)-5,6a,7,8,9,9a-Hexahydro-5-methyl-2-(phenylethynyl)-3-(phenylmethyl)cyclopent[4,5]imidazo[2,1-b]-purin-4(3H)-one; dipyridamole, AWD-12-171 and AWD-12-217; BMS-341400; UK-343,664; 5E-3623, 5E-3569, 5E-3657, E4021; KS-505a; YC-1; IDDB reference number 323951; WIN-61691; FR226807; IDDB references 461317, 462503, 461321, 461324, 466146; pyridine-4-ylmethyl 3-(1,3-benzodioxol-5-yl)-9-oxo-1,3,4,9tetrahydro-2H-pyrrolo[3,4-b]quinoline-2-carboxylate:

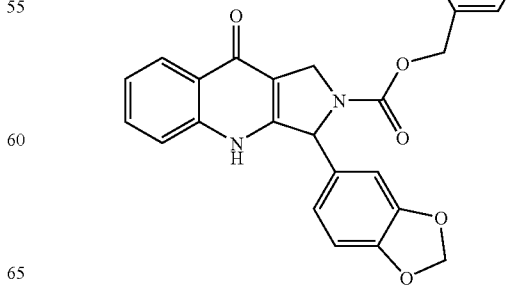

18. A method according to claim 1 or 2, wherein the PDE inhibitor is selected from Sildenafil; Zaprinast; Dipyridamole; (6aR,9aS)-2-(Biphenylylmethyl)-5,6a,7,8,9,9a-hexahydro-5-methyl-3(phenylmethyl)cyclopent[4,5]imidazo-[2,1-b]purin-4(3H)-one; and 5'-Methyl-2' (biphenylylmethyl)-3'-(phenylmethyl)spiro[cyclopentane-1, 7'(8'H)-[3H]imidazo[2,1-b]purin]-4(5'H)-one.

19. A method according to claim 3, wherein the PDE inhibitor is selected from Sildenafil; Zaprinast; Dipyridamole; (6aR,9aS)-2-(Biphenylylmethyl)-5,6a,7,8,9,9a-hexahydro-5-methyl-3(phenylmethyl)cyclopent[4,5]imidazo-[2,1-b]purin-4(3H)-one; and 5'-Methyl-2' (biphenylylmethyl)-3'-(phenylmethyl)spiro[cyclopentane-1, 7'(8'H)-[3H]imidazo[2,1-b]purin]-4(5'H)-one.

20. A method according to claim 1 or 2, wherein the PDE inhibitor is Zaprinast.

21. A method according to claim 3, wherein the PDE inhibitor is Zaprinast.

22. A method according to claim 1 or 2, wherein the PDE inhibitor is Sildenafil.

23. A method according to claim 3, wherein the PDE inhibitor is Sildenafil.

24. A method according to claim 1 or 2, wherein the PDE inhibitor is Tadalafil.

25. A method according to claim 3, wherein the PDE inhibitor is Tadalafil.

26. A method according to claim 1 or 2, wherein the PDE inhibitor is a selective inhibitor of PDE 1 and PDE 5.

27. A method according to claim 3, wherein the PDE inhibitor is a selective inhibitor of PDE 1 and PDE 5.

28. A method according to claim 1 or 2, wherein the PDE inhibitor is a selective PDE 1 inhibitor.

29. A method according to claim 3, wherein the PDE inhibitor is a selective PDE 1 inhibitor.

30. A method according to claim 1 or 2, wherein the PDE inhibitor is a selective inhibitor of PDE 5.

31. A method according to claim 3, wherein the PDE inhibitor is a selective inhibitor of PDE 5.

32. A method of increasing follicle maturation comprising treating a female with a composition comprising a phosphodiesterase (PDE) inhibitor in an amount effective to stimulate follicular maturation.

33. A method according to claim 32, wherein the composition comprises at least one PDE 4 inhibitor.

34. A method according to claim 32, wherein the composition comprises at least one PDE 4 inhibitor selected from the group consisting of Piclamilast, Roflumilast, Cilomilast, Filaminast, Mesopram, D4418, Arofylline, and CL1044.

35. A method according to claim 32, wherein the composition comprises at least one PDE 4 inhibitor and one other PDE inhibitor selected from the group consisting of a PDE 1 inhibitor, a PDE 7 inhibitor, a PDE 9 inhibitor, a PDE 10 inhibitor, and a PDE 11 inhibitor.

36. A method according to claim 32, wherein the method further comprises treatment with at least one gonadotropin selected from the group consisting of FSH, luteinizing hormone, and chorionic gonadotropin.

37. A method according to claim 33, wherein the method further comprises treatment with at least one gonadotropin selected from the group consisting of FSH, luteinizing hormone, and chorionic gonadotropin.

38. A method according to claim 34, wherein the method further comprises treatment with at least one gonadotropin selected from the group consisting of FSH, luteinizing hormone, and chorionic gonadotropin.

39. A method according to claim 35, wherein the method further comprises treatment with at least one gonadotropin selected from the group consisting of FSH, luteinizing hormone, and chorionic gonadotropin.

40. A method according to claim 32, wherein the method further comprises treatment with FSH.

41. A method according to claim 32, wherein the method further comprises administering FSH and at least one non-FSH gonadotropin hormone.

42. A method according to claim 41, wherein the non-FSH gonadotropin hormone is luteinizing hormone.

43. A method according to claim 41, wherein the non-FSH gonadotropin hormone is chorionic gonadotropin.

44. A method according to claim 32, wherein the method comprises administering a stimulator, agonist or adjuvant of FSH alone in combination with a PDE 4 inhibitor.

45. A method according to claim 44, wherein the stimulator of FSH is selected from the group consisting of Letrozole, Anastrozole, and Vorozole.

46. A method according to claim 36, wherein the PDE inhibitor and the gonadotropin hormone are administered concurrently.

47. A method according to claim 36, wherein the PDE 4 inhibitor and FSH are contained in a single vial as a mixture.

48. A method according to claim 36, wherein the PDE inhibitor is administered prior to the gonadotropin hormone treatment.

49. A method according to claim 36, wherein the PDE inhibitor is administered after the gonadotropin hormone treatment.

50. A method according to claim 36, wherein the FSH is administered at a dosage range of about 5 to 450 IU/day.

51. A method according to claim 36, wherein the ESH is administered at a dosage range of about 5 to 75 IU/day.

52. A method according to claim 32, wherein the method comprises administering to the female a composition comprising at least one PDE 4 inhibitor and an exogenous FSH hormone.

53. A method according to claim 52, wherein the exogenous FSH hormone is a recombinant FSH hormone.

54. A method according to claim 52, wherein the exogenous FSH hormone is urinary FSH hormone.

55. A method according to claim 52, wherein the PDE 4 inhibitor is administered in a dose of about 0.05 mg/day to about 5 mg/day.

56. A method according to claim 52, wherein the PDE 4 inhibitor is administered in a dose of about 10 mg/day to about 200 mg/day.

57. A method according to claim 52, wherein the FSH is administered in a dosage range of 5 IU FSH/day to 75 IU FSH/day.

58. A method according to claim 52, wherein the FSH is administered in a dosage of 150 IU FSH per day.

59. A method according to claim 52, wherein the FSH is administered in a single dose.

60. A method according to claim 52, wherein the FSH is administered in multiple doses.

61. A method according to claim 52, wherein the FSH is administered intramuscularly or subcutaneously.

62. A method according to claim 52, wherein the FSH is administered between day 2 and day 14 of the menstrual cycle of the female.

63. A method according to claim 52, wherein the FSH is administered for 7 to 12 consecutive days.

64. A method according to claim 52, wherein the method further comprises suppression of endogenous FSH and LH production in the female prior to administration of the PDE 4 inhibitor and the FSH hormone.

65. A method according to claim 64, wherein suppression of endogenous FSH and LH production is effected by the administration of GnRH or an analog thereof to the female.

66. A method according to claim 64, wherein GnRH, or an analog thereof, is administered to the female for 30 days prior to the administration of the at least one PDE 4 inhibitor and the exogenous FSH hormone.

67. A method according to claim 65, wherein GnRH, or an analog thereof, is administered in a dosage range of from about 0.25 mg to about 3 mg GnRH on a daily basis.

68. A method according to claim 52, wherein the female produces 4 or more oocytes that are harvestable.

69. A method according to claim 68, further comprising the step of harvesting the oocytes 12 days after the PDE 4 inhibitor and the FSH were first administered.

70. A method according to claim 69, further comprising the step of fertilizing the harvested oocytes in vitro, culturing the harvested, fertilized oocytes to the 4–8 cell stage, and transferring the 4–8 cell stage fertilized oocytes to the uterus of a mammal.

* * * * *